(12) United States Patent
Marks et al.

(10) Patent No.: US 11,504,150 B2
(45) Date of Patent: Nov. 22, 2022

(54) INTRAVASCULAR THROMBOEMBOLECTOMY DEVICES AND METHODS

(71) Applicant: ThrombX Medical, Inc., Hillsborough, CA (US)

(72) Inventors: Michael P. Marks, Hillsborough, CA (US); Like Que, Livermore, CA (US); Timothy John Konkol, Santa Clara, CA (US)

(73) Assignee: ThrombX Medical, Inc., Hillsborough, CA (US)

( * ) Notice: Subject to any disclaimer, the term of this patent is extended or adjusted under 35 U.S.C. 154(b) by 73 days.

(21) Appl. No.: 16/810,518

(22) Filed: Mar. 5, 2020

(65) Prior Publication Data
US 2020/0297376 A1 Sep. 24, 2020

Related U.S. Application Data

(63) Continuation of application No. PCT/US2018/050289, filed on Sep. 10, 2018.
(Continued)

(51) Int. Cl.
*A61B 17/3207* (2006.01)
*A61B 17/00* (2006.01)
*A61B 17/22* (2006.01)

(52) U.S. Cl.
CPC ........ *A61B 17/320725* (2013.01); *A61B 17/00234* (2013.01); *A61B 2017/00336* (2013.01);
(Continued)

(58) Field of Classification Search
CPC ...... A61B 17/320725; A61B 17/00234; A61B 2017/00336; A61B 2017/00358;
(Continued)

(56) References Cited

U.S. PATENT DOCUMENTS 5,011,488 A  4/1991  Ginsbrug
5,846,251 A  12/1998  Hart
(Continued)

FOREIGN PATENT DOCUMENTS

CN  1308508 A  8/2001
CN  102036611 A  4/2011
(Continued)

OTHER PUBLICATIONS

Invitation to Pay Additional Search Fees in corresponding International Patent Application No. PCT/US2018/050289, dated Nov. 13, 2018.
(Continued)

*Primary Examiner* — Ashley L Fishback
(74) *Attorney, Agent, or Firm* — Knobbe, Martens, Olson & Bear LLP

(57) ABSTRACT

Devices and methods for increasing or restoring a flow in a body lumen. The devices and the methods may treat conditions like stroke by removing a clot from a blood vessel and/or reopen the vessel. The device may include a plurality of engaging elements, a central wire, and proximal control element. The device may include a linking structure between engaging elements. The linking structure may include segments configured to respond differently upon the application of longitudinal loads. The positions of the engaging elements and the distance therebetween can be adjusted simultaneously or sequentially to promote the engagement of the clot or occlusion. The device may include be configured to inhibit or prevent the proximal engaging element from being pulled back into a microcatheter when pulling the central wire to pull the distal engaging element proximally and/or during retraction of the device holding a clot.

24 Claims, 32 Drawing Sheets

Related U.S. Application Data

(60) Provisional application No. 62/556,627, filed on Sep. 11, 2017, provisional application No. 62/556,658, filed on Sep. 11, 2017.

(52) U.S. Cl.
CPC .......... *A61B 2017/00358* (2013.01); *A61B 2017/22047* (2013.01); *A61B 2017/320716* (2013.01)

(58) Field of Classification Search
CPC ......... A61B 2017/22047; A61B 2017/320716; A61F 2/01; A61F 2/013; A61F 2/0105; A61F 2/011; A61F 2/012
See application file for complete search history.

(56) References Cited

U.S. PATENT DOCUMENTS

| | | | |
|---|---|---|---|
| 5,972,019 | A | 10/1999 | Engelson et al. |
| 5,984,957 | A | 11/1999 | Laptewicz, Jr. et al. |
| 6,001,118 | A | 12/1999 | Daniel et al. |
| 6,096,053 | A | 8/2000 | Bates |
| 6,248,128 | B1 | 6/2001 | Berry et al. |
| 6,458,139 | B1 | 10/2002 | Palmer et al. |
| 6,544,279 | B1 * | 4/2003 | Hopkins ............... A61F 2/012 606/200 |
| 6,692,504 | B2 | 2/2004 | Kurz et al. |
| 7,029,488 | B2 | 4/2006 | Schonbolz et al. |
| 8,545,526 | B2 | 10/2013 | Martin et al. |
| 8,777,976 | B2 | 7/2014 | Brady et al. |
| 8,858,497 | B2 | 10/2014 | Di Palma et al. |
| 9,149,609 | B2 | 10/2015 | Ansel et al. |
| 9,204,887 | B2 | 12/2015 | Cully et al. |
| 9,433,429 | B2 | 9/2016 | Vale et al. |
| 9,445,829 | B2 | 9/2016 | Brady et al. |
| 9,452,047 | B2 | 9/2016 | Duffy |
| 9,801,643 | B2 | 10/2017 | Hansen et al. |
| 10,271,863 | B2 | 4/2019 | Marks et al. |
| 10,517,708 | B2 | 12/2019 | Gorochow |
| 10,617,435 | B2 | 4/2020 | Vale et al. |
| 10,772,649 | B2 | 9/2020 | Hansen et al. |
| 10,792,055 | B2 | 10/2020 | Brady et al. |
| 10,881,419 | B2 | 1/2021 | Marks et al. |
| 11,026,708 | B2 | 6/2021 | Marks et al. |
| 2002/0091407 | A1 | 7/2002 | Zadno-Azizi et al. |
| 2002/0123765 | A1 | 9/2002 | Sepetka |
| 2003/0078614 | A1 | 4/2003 | Salahieh et al. |
| 2003/0163158 | A1 | 8/2003 | White |
| 2003/0176886 | A1 | 9/2003 | Wholey et al. |
| 2004/0260333 | A1 | 12/2004 | Dubrul |
| 2005/0113862 | A1 | 5/2005 | Besselink et al. |
| 2006/0155305 | A1 | 7/2006 | Freudenthal et al. |
| 2007/0100422 | A1 | 5/2007 | Shumer et al. |
| 2007/0179513 | A1 | 8/2007 | Deutsch |
| 2008/0045881 | A1 | 2/2008 | Teitelbaum et al. |
| 2008/0097401 | A1 | 4/2008 | Trapp et al. |
| 2008/0114439 | A1 | 5/2008 | Ramaiah et al. |
| 2008/0262487 | A1 | 10/2008 | Wensel et al. |
| 2009/0198269 | A1 | 1/2009 | Hannes et al. |
| 2009/0054918 | A1 | 2/2009 | Henson |
| 2009/0105722 | A1 | 4/2009 | Fulkerson et al. |
| 2009/0105737 | A1 | 4/2009 | Fulkerson et al. |
| 2009/0192485 | A1 | 7/2009 | Heuser |
| 2009/0221967 | A1 | 9/2009 | Thommen et al. |
| 2009/0292297 | A1 | 11/2009 | Ferrere |
| 2009/0299393 | A1 | 12/2009 | Martin et al. |
| 2010/0004726 | A1 | 1/2010 | Hancock et al. |
| 2010/0023034 | A1 | 1/2010 | Linder et al. |
| 2010/0114017 | A1 | 5/2010 | Lenker et al. |
| 2010/0268265 | A1 | 10/2010 | Krolik et al. |
| 2011/0060212 | A1 | 3/2011 | Slee et al. |
| 2011/0202088 | A1 | 8/2011 | Eckhouse et al. |
| 2012/0059309 | A1 | 3/2012 | Di Palma et al. |
| 2012/0059356 | A1 | 3/2012 | Di Palma et al. |
| 2012/0076577 | A1 * | 3/2012 | Yanagihara ........ A61B 1/00105 403/375 |
| 2012/0165859 | A1 | 6/2012 | Eckhouse |
| 2013/0030460 | A1 | 1/2013 | Marks et al. |
| 2013/0030461 | A1 | 1/2013 | Marks et al. |
| 2013/0345739 | A1 | 12/2013 | Brady et al. |
| 2014/0046359 | A1 | 2/2014 | Bowman et al. |
| 2014/0052161 | A1 | 2/2014 | Cully et al. |
| 2015/0250497 | A1 | 9/2015 | Marks et al. |
| 2016/0317168 | A1 | 11/2016 | Brady et al. |
| 2018/0132876 | A1 | 5/2018 | Zaidat |
| 2021/0113225 | A1 | 4/2021 | Marks et al. |

FOREIGN PATENT DOCUMENTS

| | | |
|---|---|---|
| EP | 1 054 635 B1 | 1/2010 |
| EP | 1 629 784 B1 | 1/2010 |
| EP | 1 667 588 B1 | 1/2010 |
| JP | 2003-033359 A | 2/2003 |
| JP | 2005-160648 A | 6/2005 |
| WO | WO 02/055146 A1 | 7/2002 |
| WO | WO 2007/004221 A1 | 1/2007 |
| WO | WO 2009/076482 A1 | 6/2009 |
| WO | WO 2011/006013 A1 | 1/2011 |
| WO | WO 2012/162437 A1 | 11/2012 |
| WO | WO 2015/057796 A1 | 4/2015 |
| WO | WO 2019/051425 A1 | 3/2019 |

OTHER PUBLICATIONS

International Search Report and Written Opinion in corresponding International Patent Application No. PCT/US2018/050289, dated Feb. 7, 2019.

International Preliminary Report on Patentability in corresponding International Patent Application No. PCT/US2018/050289, dated Mar. 26, 2020.

Ju-Yu Chueh et al., "Quantitative Characterization of Recanalization and Distal Emboli with a Novel Thrombectomy Device," Cardiovasc Intervent Radiol, vol. 44, published Nov. 11, 2020, pp. 318-324.

Colin J. Przybylowski et al., "Evolution of endovascular mechanical thrombectomy for acute ischemic stroke," World Journal of Clinical Cases, vol. 2, Issue 11, Nov. 16, 2014, pp. 614-622.

Extended Search Report in corresponding European Patent Application No. 18853758.3, dated Apr. 16, 2021.

Examination Report in corresponding European Patent Application No. 18853758.3, dated May 4, 2022, in 6 pages.

\* cited by examiner

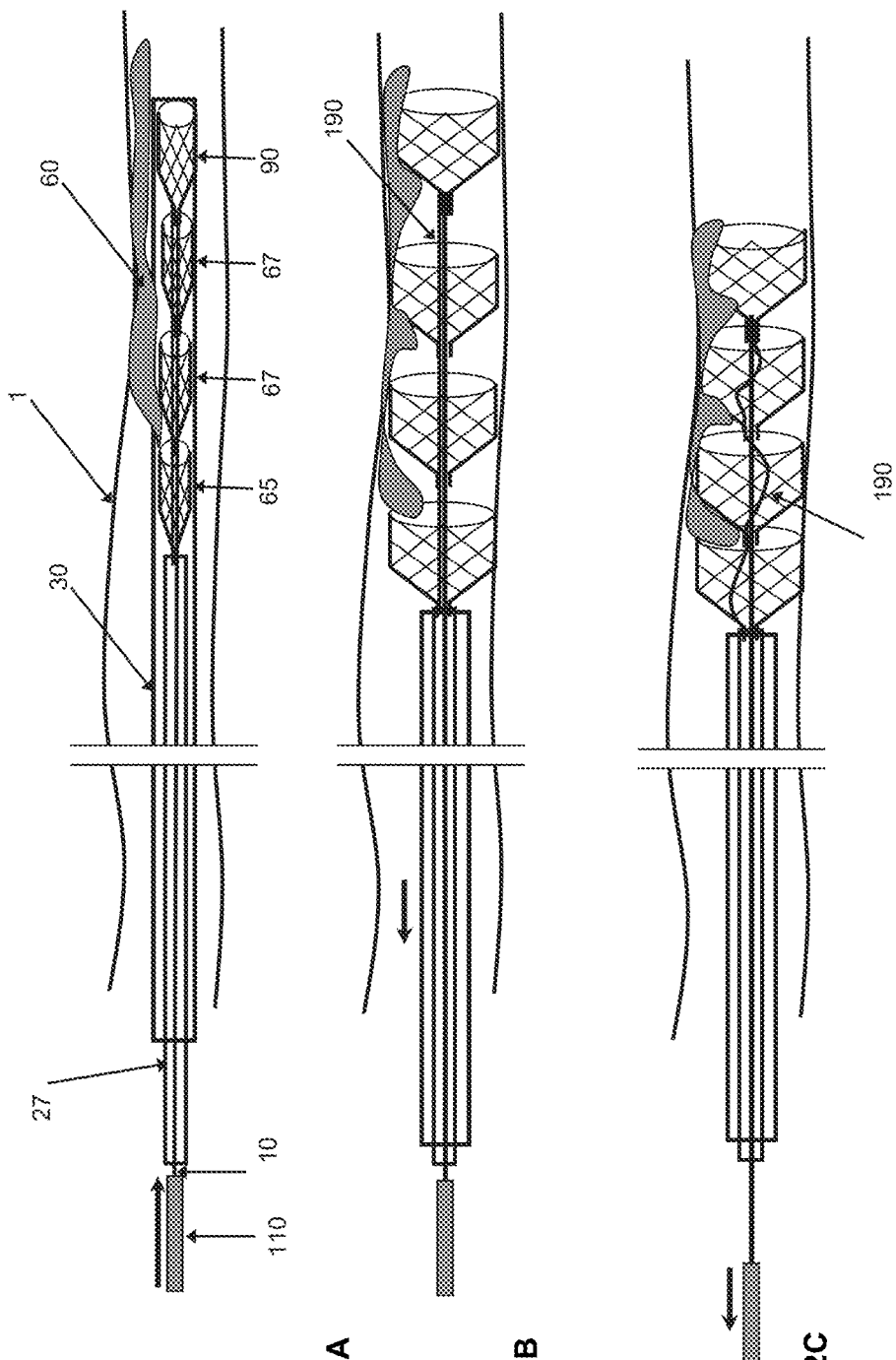

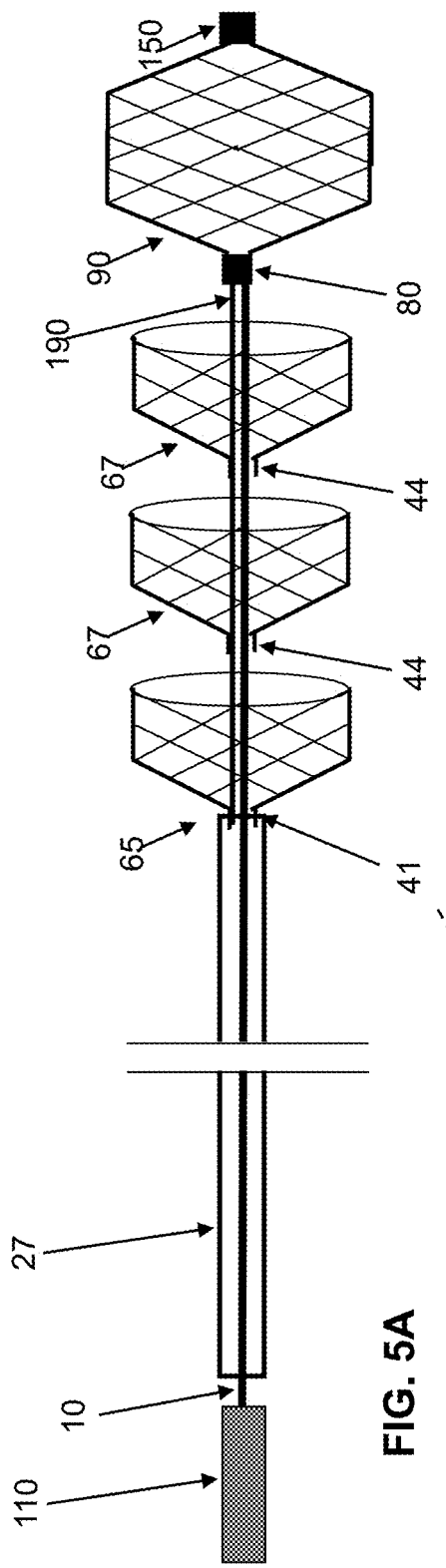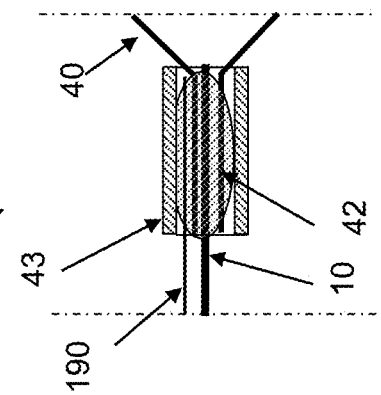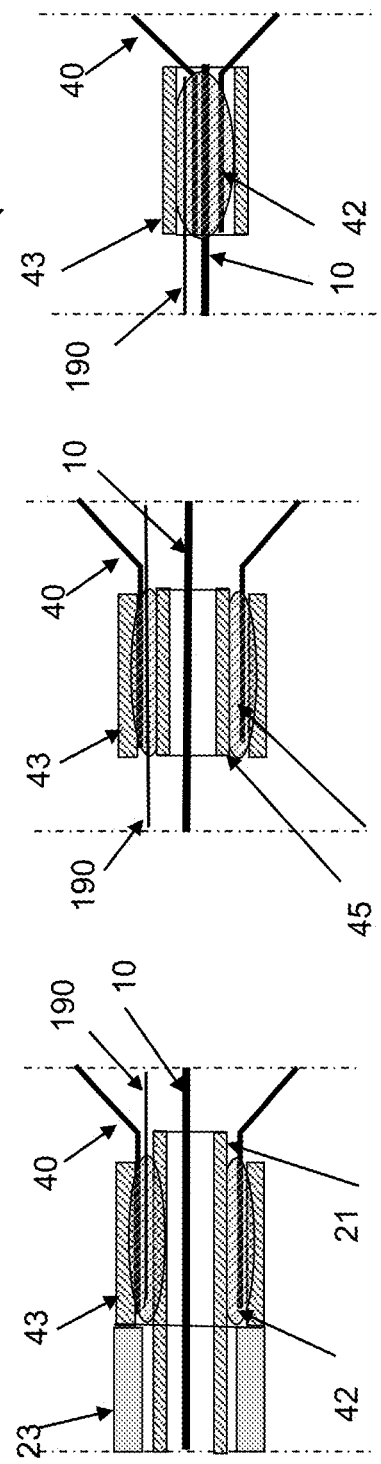

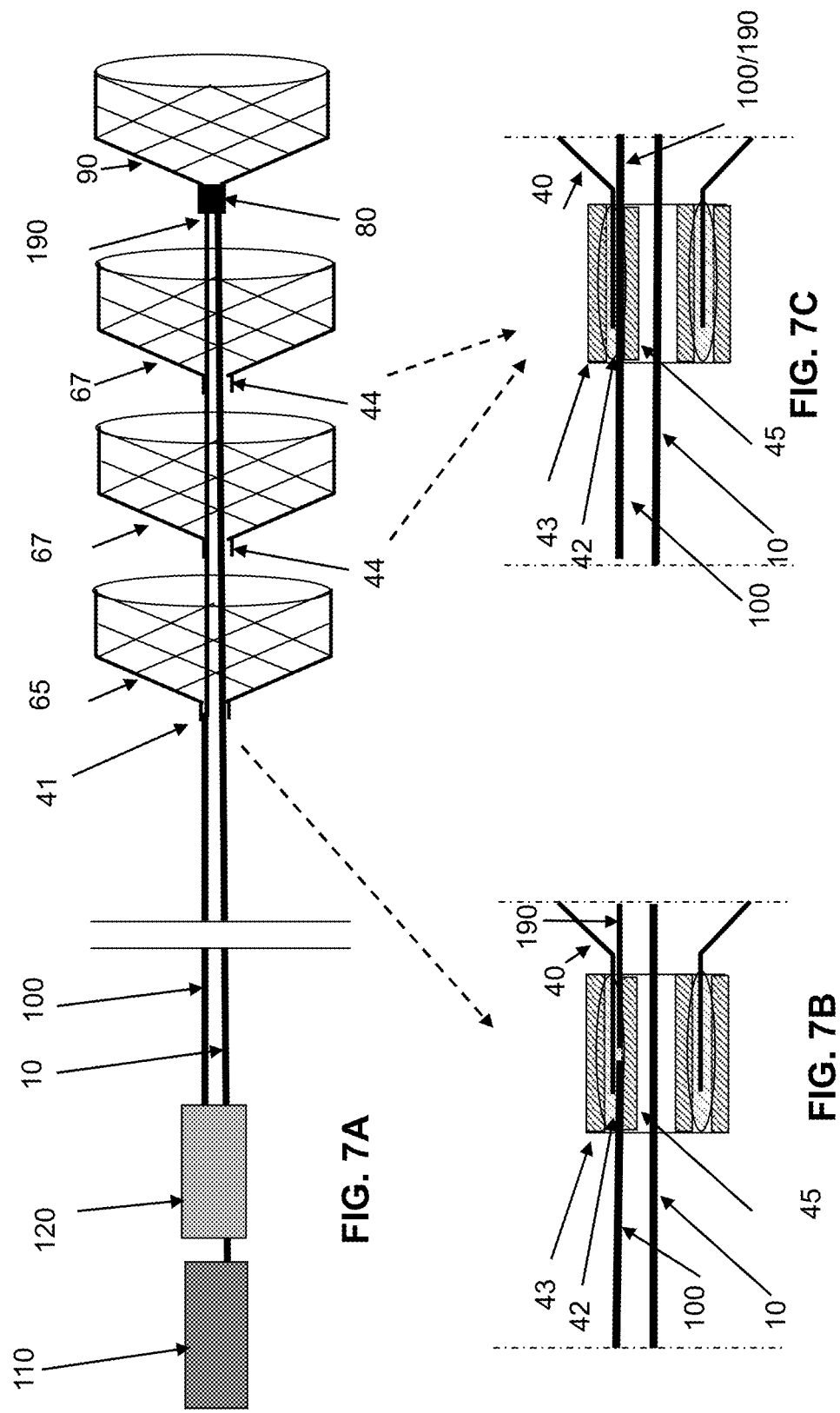

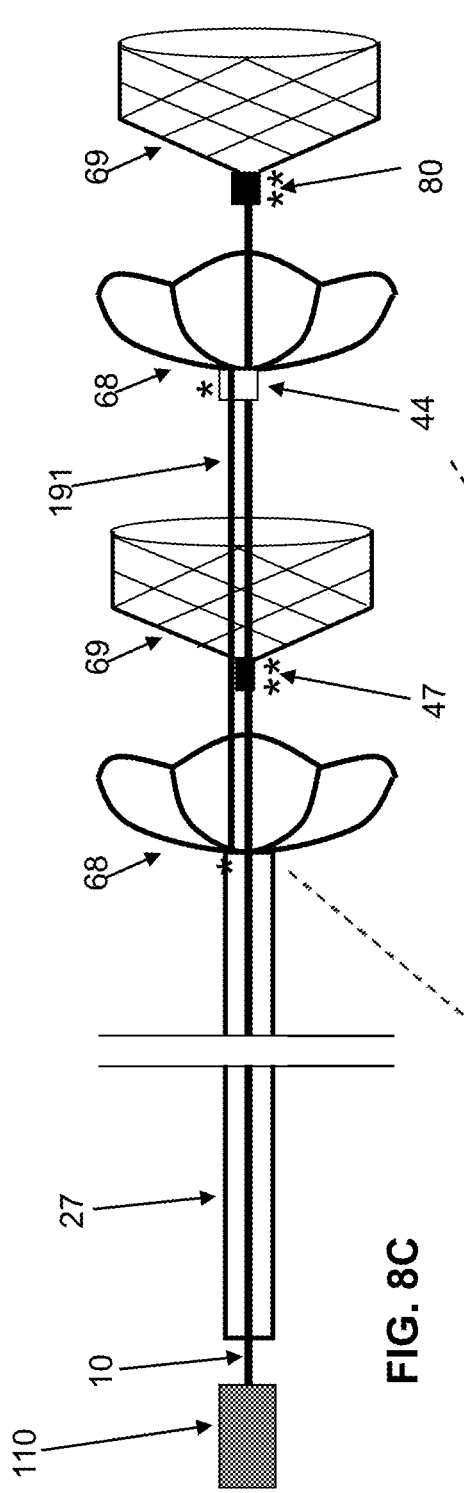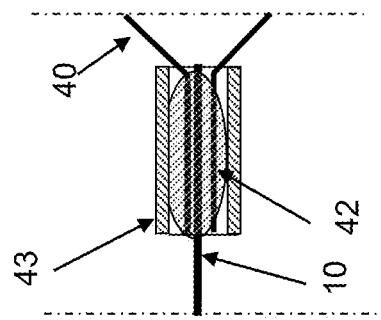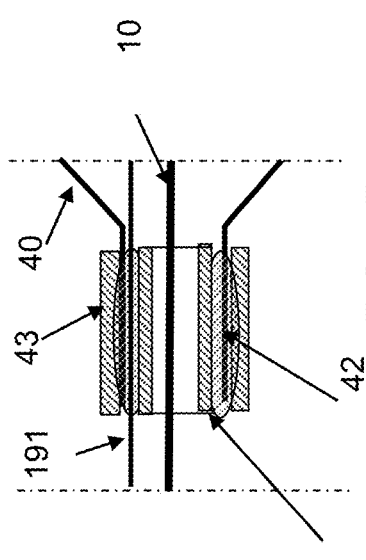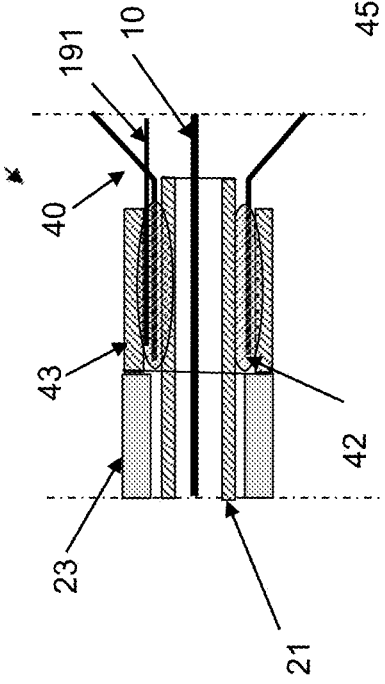

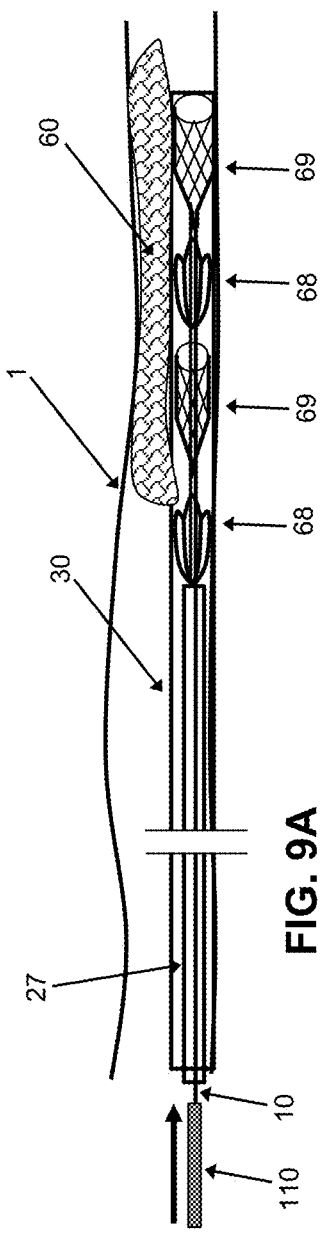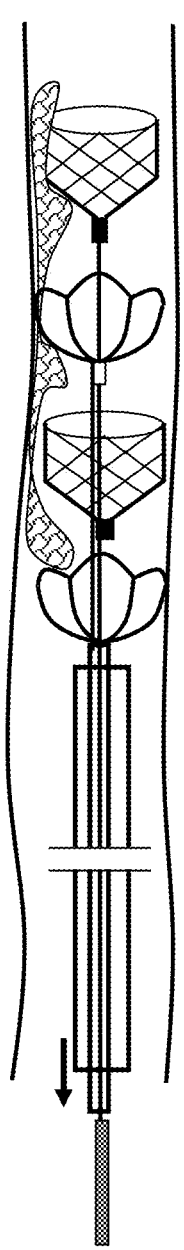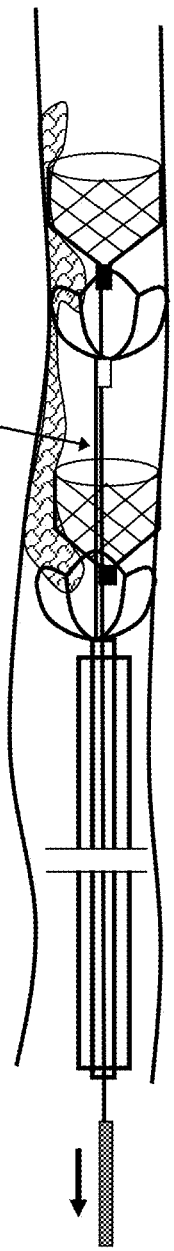

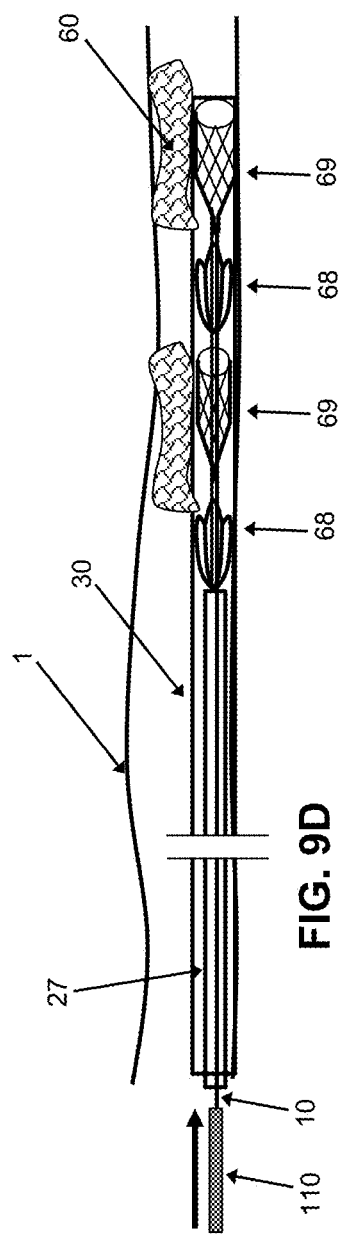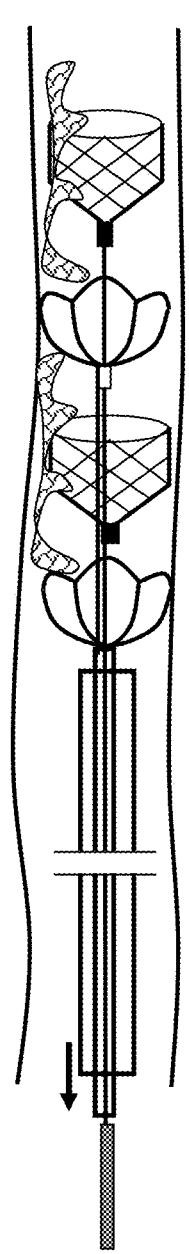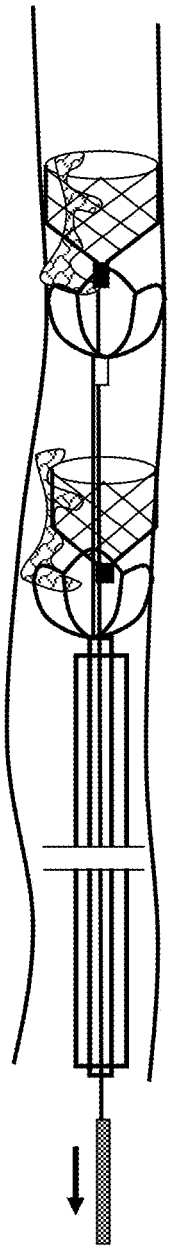

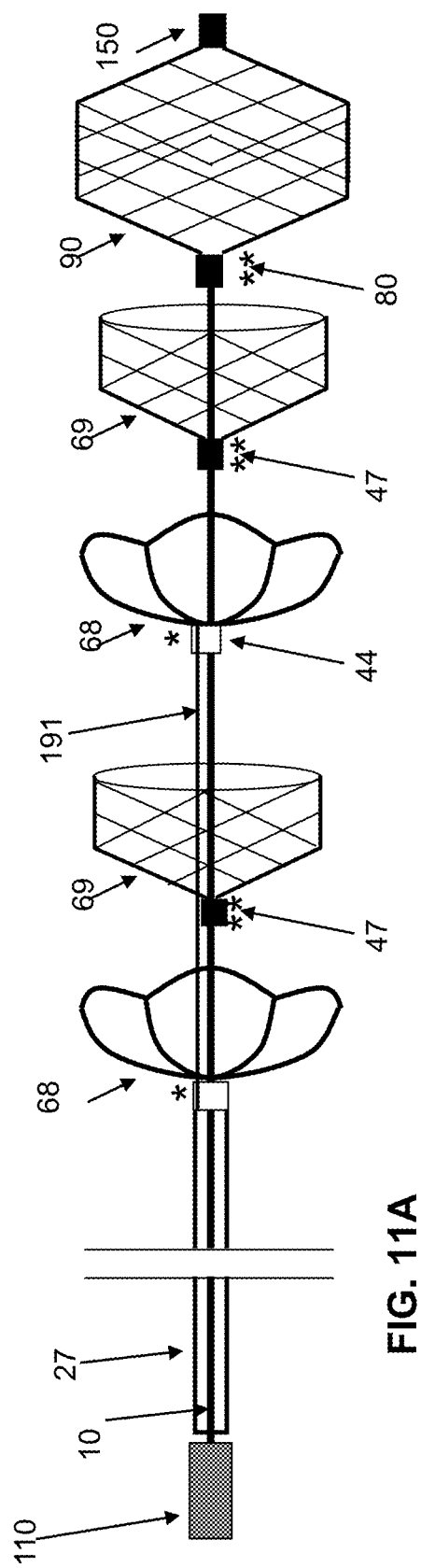
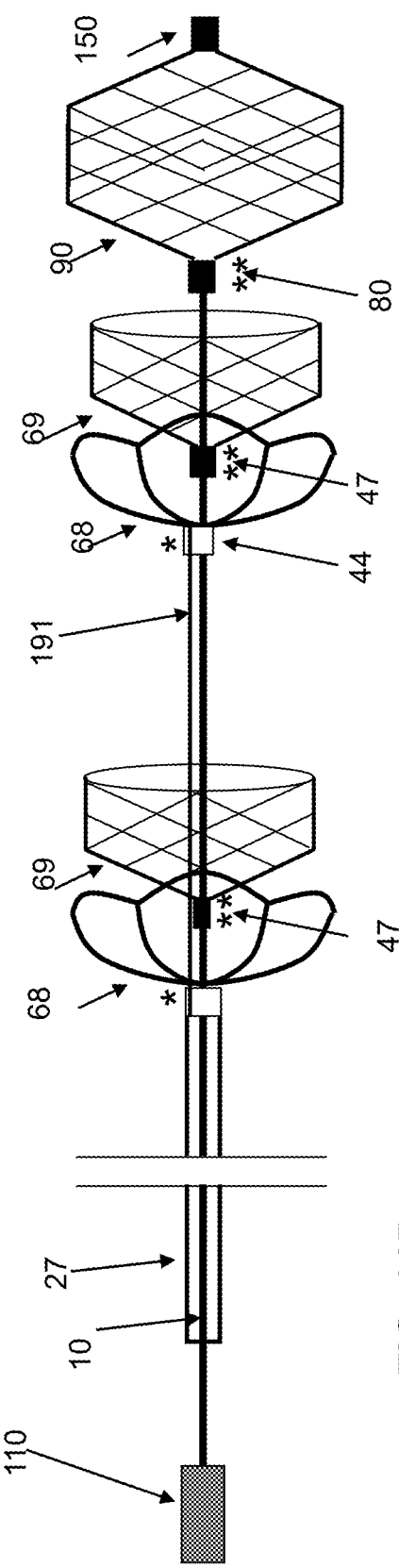
FIG. 11A
FIG. 11B

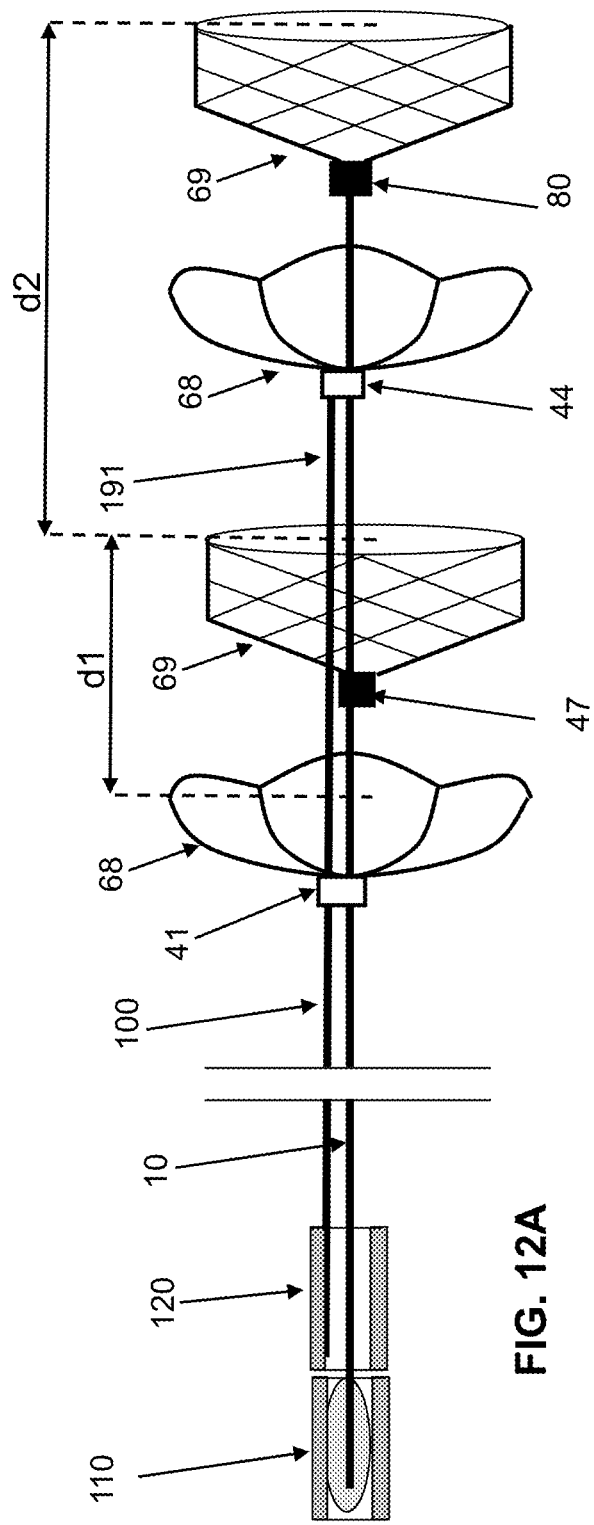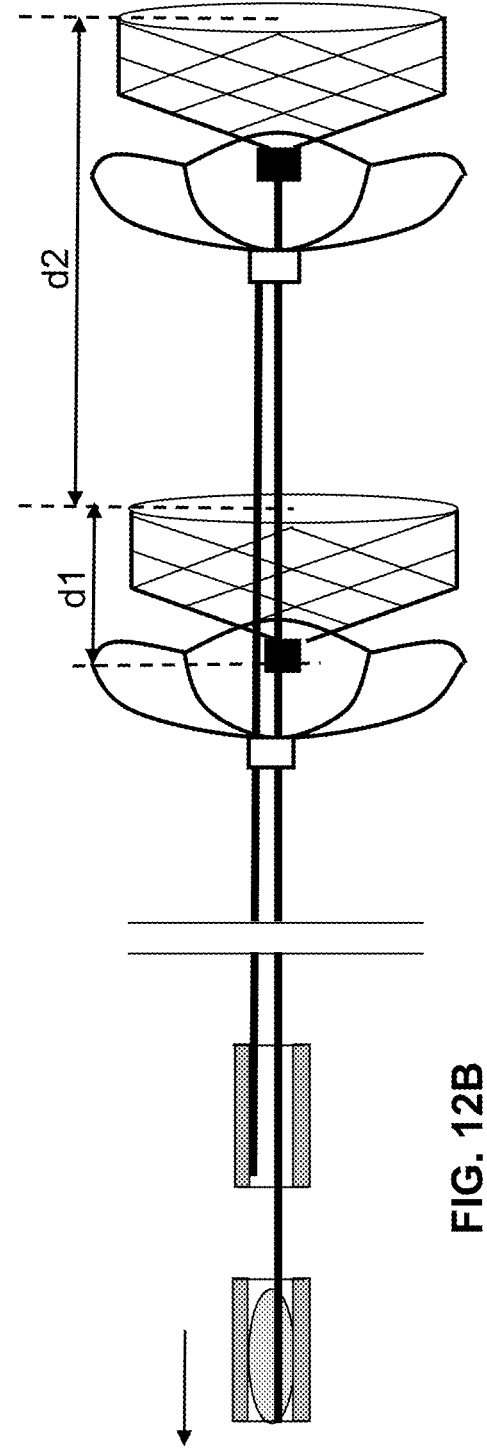

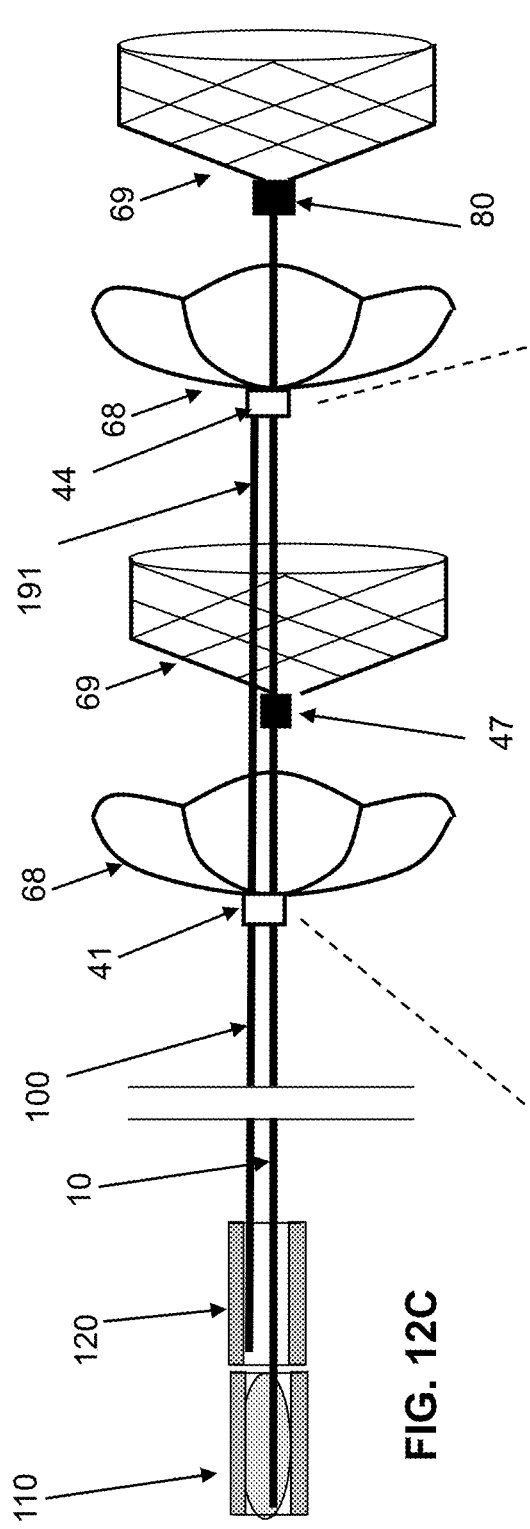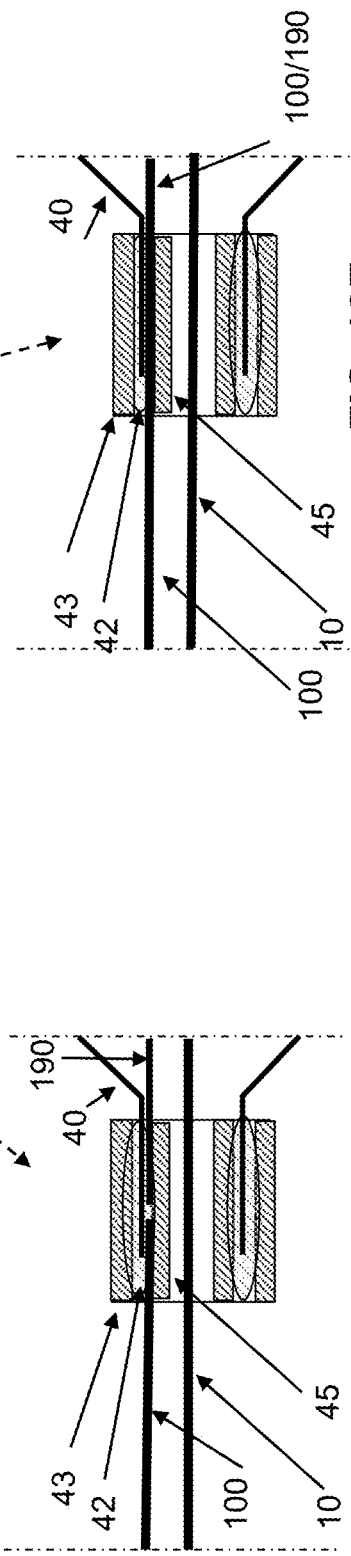

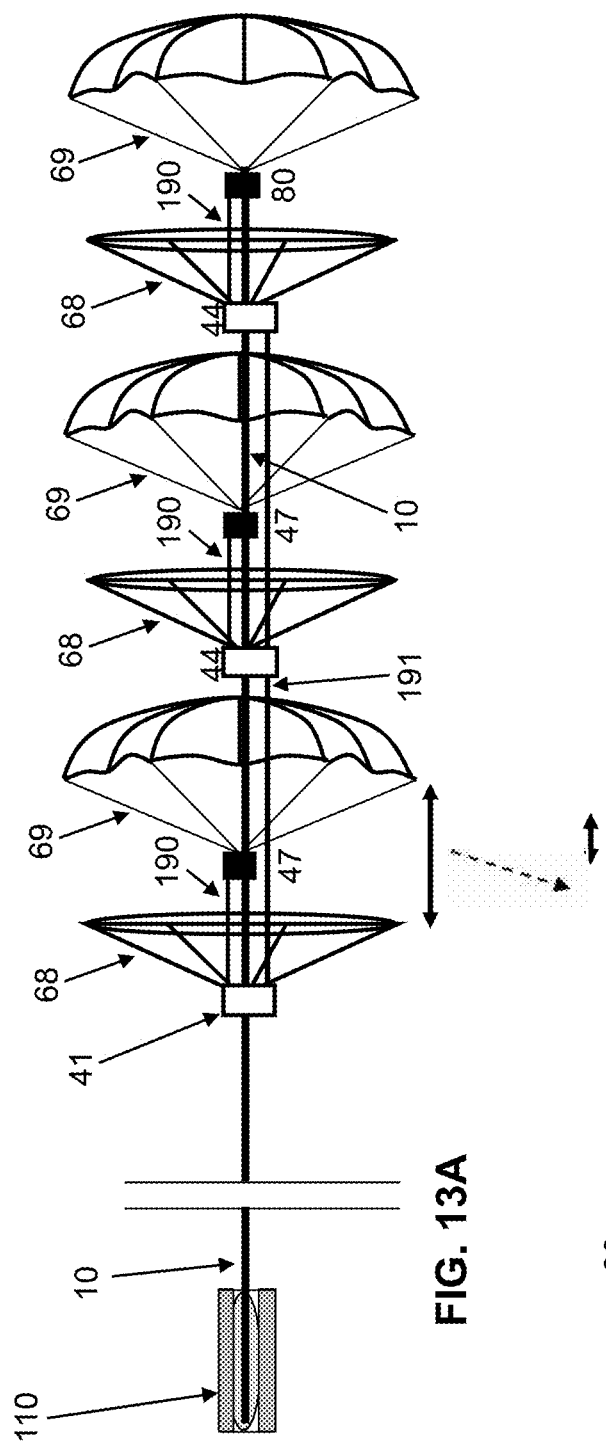
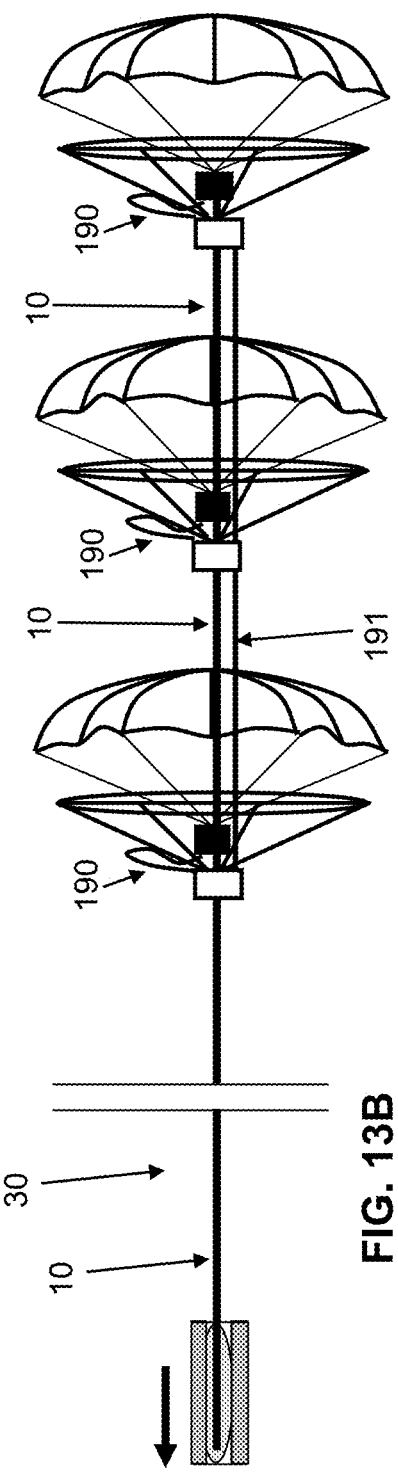
FIG. 13A
FIG. 13B

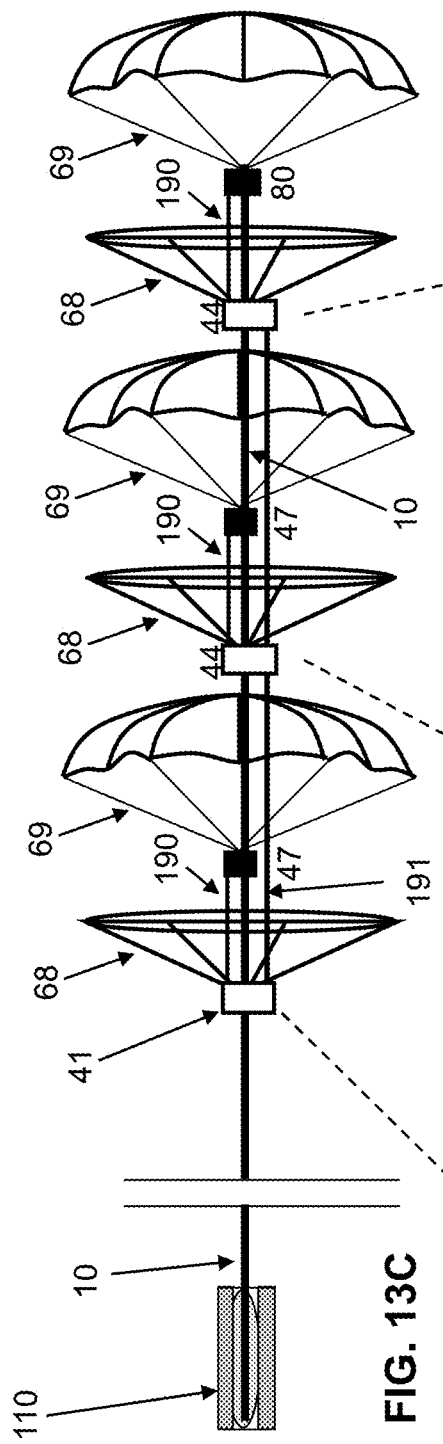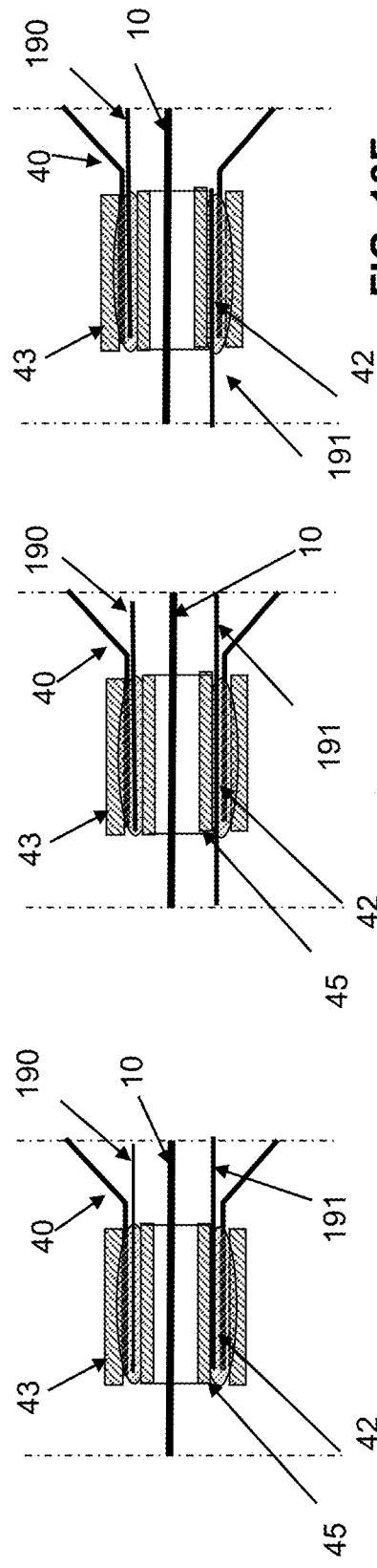
FIG. 13C
FIG. 13D
FIG. 13E
FIG. 13F

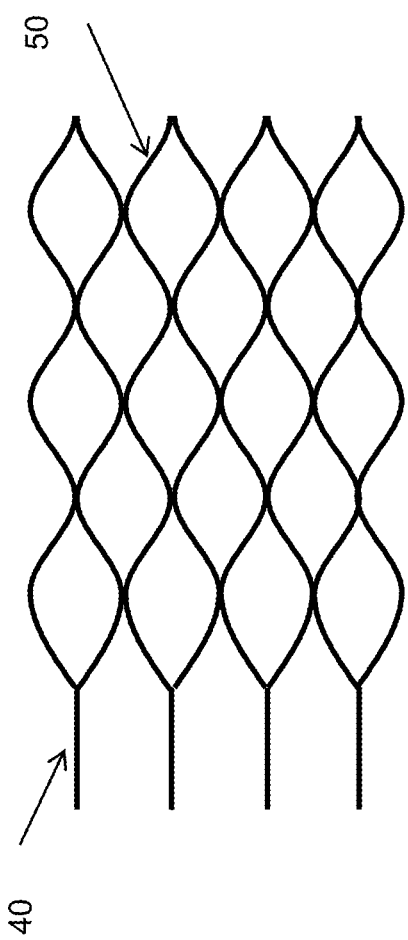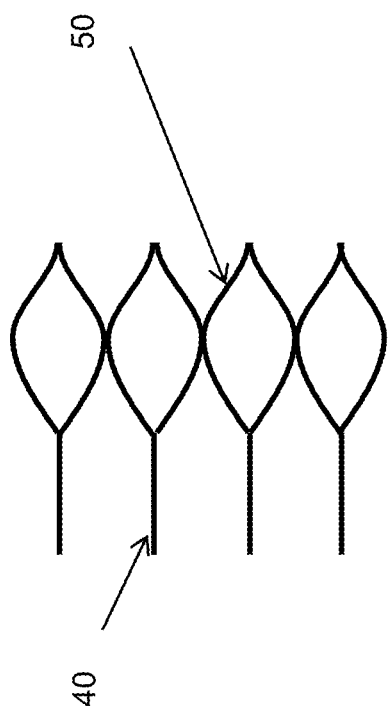

INTRAVASCULAR THROMBOEMBOLECTOMY DEVICES AND METHODS

INCORPORATION BY REFERENCE

This application is a continuation of International Patent Application No. PCT/US2018/050289, filed Sep. 10, 2018, which claims the priority benefit of U.S. Provisional Application No. 62/556,658, filed Sep. 11, 2017, and U.S. Provisional Application No. 62/556,627, filed Sep. 11, 2017, the entirety of each of which is incorporated herein by reference in their entirety for all purposes. The disclosures of each of U.S. patent application Ser. No. 13/191,306, filed Jul. 26, 2011, U.S. patent application Ser. No. 13/543,657, filed Jul. 6, 2012, and U.S. patent application Ser. No. 14/638,994, filed Mar. 4, 2015, are also incorporated herein by reference in their entirety for all purposes.

BACKGROUND

Field

The present disclosures are generally related to a device used in a body lumen such as a blood vessel and a method of using the same.

Description of the Related Art

A variety of disease conditions can be caused, at least in part, by blockage or, occlusions or clots of blood vessels. A well-known example of such conditions includes, but is not limited to stroke. Other such conditions include a myocardial infarction, limb ischemia, occlusions or clots of vascular grafts and bypasses, and venous thromboses.

A stroke is often referred as a "brain attack." It often results in rapid and significant loss of brain function due to disturbance in the blood supply to the brain. As a result, inabilities in movement, use of language, vision and many other biological functions may be temporarily or irreversibly impaired. Strokes are either hemorrhagic (due to bleeding) or ischemic (due to inadequate blood supply). The majority of strokes are ischemic. It is estimated that about 700,000 ischemic strokes occur in the United States annually. The major causes of an ischemic stroke include thrombosis (clotting) in a blood vessel supplying the brain or an embolus from another source such as the heart going to a blood vessel supplying the brain. Sometimes a thrombosis occurs where there is a pre-existing stenosis of blood vessels in the brain, usually from atherosclerotic disease.

Treatments for acute ischemic stroke are concentrated on re-establishing blood flow to the brain as quickly as possible. They include the use of a drug such as tissue plasminogen activator (tPA), a thrombolytic agent (clot-busting drug). More recently devices such as stent retriever devices (Trevo, Stryker, Fremont, Calif.; Solitaire, Covidien, Irvine, Calif.) and suction thrombectomy catheters (Penumbra, Inc., Alameda, Calif.) have been approved by the Food and Drug Administration for thrombectomy in acute stroke. These devices do not always achieve complete recanalization or reperfusion. Sometimes they fail to open the vessel at all or may only partially open the vessel. They also may take some time to work, with multiple passes of the devices into the intracranial circulation needed before the vessel is reopened. In addition, they may fragment the clot and allow some portion of the clot to go out more distally in the cerebral circulation. There is a need for devices with high rates of complete recanalization, with complete or partial clot capture, performed in a more rapid manner.

SUMMARY

The present disclosure relates to devices and methods for removing an obstruction from a body lumen.

In some examples, a device for removing an obstruction from a body lumen may comprise an engaging element and a microcatheter at least partially containing the engaging element. The engaging element, when expanded upon unsheathing from the microcatheter, may be configured to inhibit re-sheathing of the engaging element in the microcatheter upon application of at least one of a proximal force to the engaging element or a distal force to the microcatheter.

In some examples, a device for removing an obstruction from a body lumen may comprise a central wire comprising a proximal end and a distal end, an engaging element at or near the distal end of the central wire, and a microcatheter at least partially containing the engaging element during introduction into the body lumen. The engaging element, when expanded upon unsheathing from the microcatheter, may be configured to inhibit re-sheathing of the engaging element in the microcatheter upon application of at least one of a proximal force to the engaging element or a distal force to the microcatheter.

A proximal end of the engaging element may comprise a stopper configured to expand radially upon unsheathing the engaging element from the microcatheter. The stopper may comprise loops configured to bend radially outward upon unsheathing the engaging element from the microcatheter. The stopper may comprise a spiral spring wire configured to expand radially outward upon unsheathing the engaging element from the microcatheter. The engaging element may comprise legs having a thickness configured to inhibit re-sheathing of the engaging element in the microcatheter when the legs are expanded. Legs of the engaging element may be at an angle of between 30° and 90° with respect to a longitudinal axis of the microcatheter when the legs are expanded. The engaging element may comprise wires or struts. The engaging element may be self-expandable upon unsheathing the microcatheter. The engaging element may be configured to inhibit re-sheathing of the microcatheter upon application of a proximal force of 50 grams to 450 grams. The device may further comprise a second engaging element located distal to the engaging element. The second engaging element may be fixedly attached to the distal end of the central wire. The engaging element may be slidable on the central wire. The device may comprise a linking connector coupled to the engaging element and the second engaging element, the linking connector spacing the engaging element and the second engaging element at a distance. The linking connector may be a wire, a hypotube with slits, or a braid. The device may comprise a third engaging element located between the engaging element and the second engaging element.

In some examples, a method of removing at least part of an occlusion from a body lumen may comprise introducing into the body lumen a device for removing an obstruction from a body lumen. The device may comprise a central wire comprising a proximal end and a distal end, an engaging element at or near the distal end of the central wire, and a microcatheter at least partially containing the engaging element during introduction into the body lumen. The engaging element, when expanded upon unsheathing from the microcatheter, may be configured to inhibit re-sheathing of the engaging element in the microcatheter upon application of at least one of a proximal force to the engaging element or a distal force to the microcatheter. The introducing may include the engaging element at least partially contained in the microcatheter, until the engaging element is proximate the occlusion. The method may further comprise deploying the engaging element from the microcatheter so that a distal tip of the microcatheter is proximal to the engaging element; engaging at least part of the occlusion with the engaging element; abutting the distal tip of the microcatheter with the proximal end of the engaging element; and removing the engaged occlusion from the body lumen. During the removing, the engaging element may inhibit re-sheathing of the microcatheter over the engaging element.

The proximal end of the engaging element may comprise a stopper configured to expand radially upon unsheathing the microcatheter. Legs of the engaging element may have a thickness configured to inhibit re-sheathing of the microcatheter when the legs are expanded. Legs of the engaging element may be at an angle of between 30° and 90° with respect to a longitudinal axis of the microcatheter when the legs are expanded. Abutting the distal tip of the microcatheter with the proximal end of the engaging element may comprise proximally retracting the engaging element. Abutting the distal tip of the microcatheter with the proximal end of the engaging element may comprise distally advancing the microcatheter. Distally advancing the microcatheter may comprise the engaging at least part of the occlusion with the engaging element. Removing the engaged occlusion from the body lumen may comprise proximally retracting the engaging element. Removing the engaged occlusion from the body lumen may comprise proximally retracting the microcatheter. Abutting the distal tip of the microcatheter with the proximal end of the engaging element may comprise proximally retracting the engaging element and distally advancing the microcatheter. Abutting the distal tip of the microcatheter with the proximal end of the engaging element may comprise at least one of proximally retracting the engaging element or distally advancing the microcatheter. The device may comprise a second engaging element, wherein the positioning may comprise locating the engaging element proximal of the occlusion and the second engaging element distal of a proximal end of the occlusion. The second engaging element may be distal to a distal end of the occlusion. The method may further comprise adjusting positions of the engaging element and the second engaging element by at least one of: holding the microcatheter while pulling the central wire to engage the occlusion between the engaging element and the second engaging element, or holding the central wire while pushing the microcatheter to engage the occlusion between the engaging element and the second engaging element. The device may further comprise a linking connector between the engaging element and the second engaging element, wherein the linking connector engages the occlusion.

In some examples, a device for removing an obstruction from a body lumen may comprise a central wire comprising a proximal end and a distal end, a plurality of engaging elements comprising a distal engaging element, a proximal engaging element, and a middle engaging element between the distal and proximal engaging elements, and a linking connector comprising a first segment coupled to the proximal engaging element and the middle engaging element and a second segment coupled to the middle engaging element and the distal engaging element. The distal engaging element may be fixedly attached to the distal end of the central wire. The proximal engaging element and the middle engaging element may be slidable relative to the central wire. The first and second segments may be configured to collapse simultaneously.

In some examples, a device for removing an obstruction from a body lumen may comprise a central wire comprising a proximal end and a distal end, a plurality of engaging elements comprising a distal engaging element, a proximal engaging element, and a middle engaging element between the distal and proximal engaging elements, and a linking connector comprising a first segment coupled to the proximal engaging element and the middle engaging element and a second segment coupled to the middle engaging element and the distal engaging element. The distal engaging element may be fixedly attached to the distal end of the central wire. The proximal engaging element and the middle engaging element may be slidable relative to the central wire. The first and second segments may be configured to collapse sequentially.

In some examples, a device for removing an obstruction from a body lumen may comprise a central wire comprising a proximal end and a distal end, a plurality of engaging elements comprising a distal engaging element, a proximal engaging element, and a middle engaging element between the distal and proximal engaging elements, and a linking connector comprising a first segment coupled to the proximal engaging element and the middle engaging element and a second segment coupled to the middle engaging element and the distal engaging element. The distal engaging element may be fixedly attached to the distal end of the central wire. The proximal engaging element and the middle engaging element may be slidable relative to the central wire. The linking connector may be configured to space the engaging elements apart at a distance. The first segment may be configured to withstand an axial loading different than the second segment such that upon application of a longitudinal axial load to the linking connector, the first and second segments may be configured to collapse sequentially.

The linking structure may comprises a flexible wire, the flexible wire configured to buckle upon application of the longitudinal axial load. The first segment may comprise a different stiffness than the second segment. The first segment may be thicker than the second segment. The linking connector may comprise a tubing including slits. The tubing may be configured to foreshorten upon application of the longitudinal axial load. The slits may be parallel to a longitudinal axis of the tubing. The slits may be at an angle to a longitudinal axis of the tubing. The slits may comprise helical slits along a longitudinal axis of the tubing. The helical slits may have different pitches in the first and second segments. The slits in the first and second segments may differ by one or more of patterns or density. The linking connector may comprise a braid, the braid configured to foreshorten when the central wire is pulled proximally. The braids in the first and second segments may differ by one or more of a braid angle or a braid density. The proximal engaging element may be configured to inhibit re-sheathing of the microcatheter over the proximal engaging element upon application of a proximal force. Upon application of a longitudinal axial load to the linking connector, the second segment may collapse before the collapsing of the first segment. Upon application of a longitudinal axial load to the linking connector, the first segment may collapse before the collapsing of the second segment.

In some examples, a method of removing at least part of an occlusion from a first location in a body lumen may comprise introducing into the body lumen a device for removing an obstruction from a body lumen. The device may comprise a central wire comprising a proximal end and a distal end, a plurality of engaging elements comprising a distal engaging element, a proximal engaging element, and a middle engaging element between the distal and proximal engaging elements, and a linking connector comprising a first segment coupled to the proximal engaging element and the middle engaging element and a second segment coupled to the middle engaging element and the distal engaging element. The distal engaging element may be fixedly attached to the distal end of the central wire. The proximal engaging element and the middle engaging element may be slidable relative to the central wire. The linking connector may be configured to space the engaging elements apart at a distance. The first segment may be configured to withstand an axial loading different than the second segment such that upon application of a longitudinal axial load to the linking connector, the first and second segments may be configured to collapse sequentially. The introducing may be until the proximal engaging element is proximal to the occlusion and the distal engaging element is distal to a proximal end of the occlusion. The method may further comprise adjusting positions of the plurality of engaging elements by application of a proximal force so as to reduce a distance between the distal and middle engaging elements first to engage at least part of the occlusion between the distal end middle engaging elements and reduce a distance between the middle and proximal engaging elements to engage at least another part of the occlusion between the middle and proximal engaging elements; and removing the engaged occlusion from the first location.

The method may further comprise capturing the occlusion between an inner wall of the body lumen and a lateral surface of at least one of the plurality of engaging elements.

BRIEF DESCRIPTION OF THE DRAWINGS

FIGS. 2A-C show another non-limiting, illustrative example of a device according to some embodiments of the invention, particularly when the device is located in a body lumen, and illustrates some non-limiting examples of a mechanism to remove an occlusion/clot from a blood vessel according to some embodiments of the invention.

FIG. 5A shows still another non-limiting, illustrative example of a device according to some embodiments of the invention where the device comprises a plurality of engaging elements.

FIGS. 5B-D show detailed locations and structures of connectors at the proximal end of proximal engaging element, middle engaging elements, and distal engaging element. FIGS. 5B-D also show the relationship among the connectors, control tubing apartment, central wire, and connection wire.

FIGS. 7A-C show still other non-limiting embodiments of a device according to the invention where the device comprises a plurality of engaging elements. The device may further comprise a control wire, an alternative to the tubing compartment. In the embodiments shown in FIG. 7A, the device comprises a connection wire and a control wire. The connection wire and the control wire may be joined at the proximal end of the proximal engaging element. The control wire may be operably connected to a control wire handle at the proximal end of the device. FIG. 7B shows certain, non-limiting embodiments of a proximal connector that may join the control wire, the connection wire and the legs of the proximal engaging element inside the proximal connector. Alternately, a separate connection wire may not be necessary in some of such embodiments. Therefore, as illustrated in FIG. 7C, the control wire and the connection wire can be from the same piece of wire, with the connection wire section/segment being small and flexible and the control wire segment being slightly larger and pushable. The control/connection wire and the legs of the proximal engaging element may be joined via a connector.

FIG. 8A shows the engaging units/pairs are open, FIGS. 8 C-F show the detailed connector structures and their relationship with the control tubing apartment, central wire, and spacing wire.

FIGS. 9A-F show still another non-limiting embodiment of a method according to the invention where the device illustrated in FIGS. 8A-F is used to treat or remove one or more occlusion(s) from a body lumen. FIGS. 9A-C shows an embodiment where a relatively large occlusion is removed by the device comprising a plurality of operation units/pairs. FIGS. 9D-F shows an embodiment where more than one occlusion are removed individually by multiple operation units/pairs.

FIGS. 11A-B show still another non-limiting embodiment of a device according to the invention where the device comprises a plurality of engaging elements, some of which may function as a receiving element whereas some other of which may function as a capturing element. In certain embodiments, a separate distal engaging element may be added at the tip of the central wire to catch the clot debris which may be closed at its distal end. Further, in some embodiments, the distal engaging element may be larger in size and diameter than the other engaging elements. However, the stiffness of the distal engaging element can be less than that of the other engaging elements.

FIGS. 12A-E show still another non-limiting embodiment of a device according to the invention where the device comprises a plurality of engaging elements, some of which may function as receiving elements whereas some other of which may function as a capturing/cinching element. In addition, the device may further comprise a control wire. The control wire, in some embodiments, may be operably connected to a handle at the proximal end of the device with which an operator can manipulate the control wire, e.g. pushing or pulling the control wire. All the receiving elements are fixed to the spacing wire with designed spacing in between and they can move freely along the central wire. All the capturing elements are fixed to the central wire. By controlling one or both of the control wire and the central wire, the space between the engaging elements can be adjusted so as to maximize the engagement and containment of an occlusion by the device. FIGS. 12A and 12B show the adjustment of the space between the engaging elements. FIGS. 12D-E show views of certain, non-limiting embodiments of a proximal connector.

FIGS. 13A-F show still alternative non-limiting embodiments of a device according to the invention where the device comprises a plurality of engaging elements. In certain embodiments, two engaging elements, one being a receiving element and the other being a capturing element, form an individual operation unit/pair. The device can comprise multiple engaging operation units/pairs. The receiving elements in different operation units/pairs can be associated with or connected to a connection wire. In addition, in certain embodiments, the engaging elements in a same unit/pair (e.g. at least one receiving element and one capturing element) may be connected to or associated with a spacing wire. FIG. 13B shows the device where the spaces between the engaging elements are reduced. FIGS. 13D-F show the relationship of the connectors with the engagements elements, connection wires, spacing wires and central wire at various locations of the engagement compartment.

FIGS. 15A-B show still another alternative, non-limiting illustrative embodiments of structures that an engaging element can be made from.

DETAILED DESCRIPTION

Figure 1A:
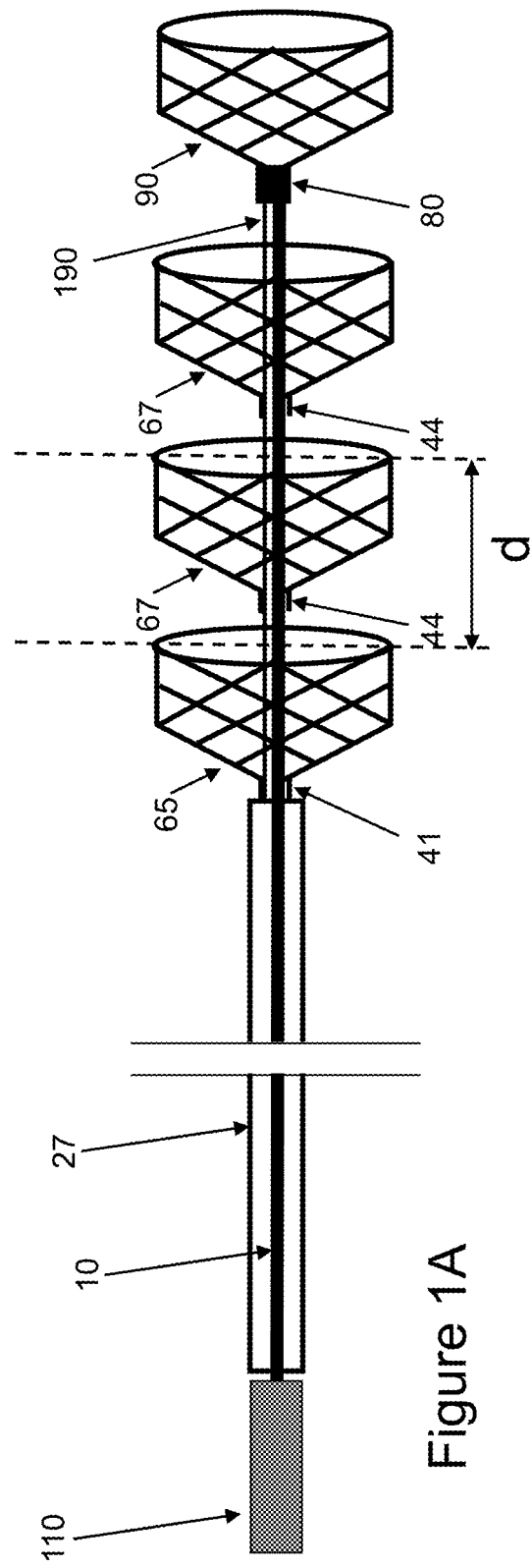
FIGS. 1A-B show a non-limiting, illustrative example of a device according to some embodiments of the invention.

The present disclosure is generally related to a device used in a body lumen, such as a blood vessel, and a method of using the same. In some embodiments, the device may be positioned in the body lumen to remove occluding substances such as a blood clot, or foreign body from the lumen. Some aspects of the present invention provide a device and method that are configured to treat conditions in blood vessels which include, but are not limited to, a stroke. In some embodiments, the device and method are configured to treat conditions related to an ischemic stroke by removing an occlusion/clot from a blood vessel and/or reopen a blood vessel and resume blood flow therein. Non-limiting examples of blood vessels may include: an artery, a vein or a surgically implanted graft and bypass serving as a component of the circulatory system.

The term "occlusion" or "clot" generally includes any matter partially or completely obstructing a lumen of the blood vessel. The occlusion/clot slows or obstructs a flow (e.g., a stream of blood or any other biological fluid) running through the lumen. Examples of the occlusion/clot may include blood occlusions/clots and atherosclerotic plaques present in the vessel as well as fat or foreign bodies.

The term "stroke" generally includes a condition(s) that is in part caused due to disturbance in blood supply to a brain. The disturbance can be caused by blockage (e.g. ischemic stroke) and/or hemorrhage (e.g. hemorrhagic stroke). In particular, an ischemic stroke can be caused due to partial or substantial occlusion of a blood vessel. Treatment of the ischemic conditions can be applied to blood vessels present in the brain as well as in other tissues such as the heart. Accordingly, the device and method disclosed in this application are not limited to use in any particular organs but can be applied to any blood vessel of the body that would benefit from removal of an occlusion/clot to restore blood flow. In addition, the device and method according to the present invention can be used to treat venous occlusions/clot which may result in other conditions besides ischemia.

The device can be introduced into the blood vessel through a catheter or microcatheter. The "catheter" or "microcatheter" generally includes a tubular structure that can be inserted into a body lumen, thereby allowing administration of a device and/or chemicals to a body area that needs treatment.

Furthermore, many different modifications and alternations, which should be obvious to a person with ordinary skill in the art based on the disclosure herein, can also be done without affecting the scope of the invention to properly serve the specific treatment conditions. Therefore, not only the examples disclosed in this application but also such an obvious modification and alteration based on the disclosure herein should also be included in the scope of the invention.

One aspect of the present invention is related to a device for use in a blood vessel comprising multiple engaging elements (for example, two, three, four, or more), a control tubing compartment, a central wire, and or a control wire. The engaging elements can form a self-expanding compartment.

Another aspect of the present invention is related to a device for use in a blood vessel comprising a microcatheter, a central wire, a tubing component, and an engaging compartment. The engaging compartment may comprise a distal engaging element, optional middle engaging element(s), and a proximal engaging element. The engaging element can be linked with connection wire and/or spacing wire via connectors. In some embodiments, the distal engaging element may be associated with the central wire. The space(s) between the engaging elements may be adjustable. The space between adjacent elements can be adjusted approximately from 0 to 50 mm in at least some embodiments. In certain embodiments, the distance between the engaging elements may be adjusted approximately 0 mm, 5 mm, 10 mm, 15 mm, 20 mm, 25 mm, 30 mm, 35 mm, 40 mm, 45 mm, and 50 mm, and any range there between. In alternative embodiments, the space between the engaging elements may be adjusted to be more than 50 mm.

In some embodiments, the device can be introduced into a blood vessel. The sizes of blood vessels vary enormously, from a diameter of about 0.03 inch (about 1 mm) in smaller arteries and veins to 1.0 inch (about 25 mm) in larger arteries, and to 1.2 inches (about 30 mm) in the aorta. Accordingly, in some embodiments, the diameter of the device may range from approximately 0.01 inch (about 0.25 mm) to 1.0 inch (about 25 mm), and to 1.2 inches (about 30 mm) when the device is an in an expanded state. Also, the diameter of a single device may vary during the operation as the engaging compartment gets opened (or expanded) or closed (or collapsed). In some other embodiments, the diameter of the device in a collapsed state may range from approximately 0.01 inch, approximately 0.02 inch, approximately 0.03 inch, approximately 0.04 inch, approximately 0.05 inch, approximately 0.06 inch, approximately 0.07 inch, approximately 0.07 inch, approximately 0.08 inch, approximately 0.09 inch, approximately 0.10 inch, approximately 0.12 inch, approximately 0.14 inch, approximately 0.16 inch, approximately 0.18 inch, approximately 0.20 inch, approximately 0.30 inch, approximately 0.40 inch, approximately 0.50 inch, approximately 0.60 inch, approximately 0.70 inch, or any range between the above-listed values.

In some embodiments, the device further comprises a central wire. The central wire may pass through the tubing component and move freely there through. In certain embodiments, the central wire is associated with the engaging compartment. More particularly, the central wire may be associated with the distal engaging element, the optional middle element(s), and the proximal engaging element. Association generally refers to any type of connection between two objects. Association includes fixation in that when two objects are associated, movement of one object would be hindered by another object. In other words, once the two objects are associated in a way of fixation, movement of two objects can be synchronized. However, association does not necessarily indicate fixation of one object to another. Accordingly, when two objects are associated but not in a state of fixation, movement of one object with respect to the other object may not be hindered. Therefore, the middle element(s) and the proximal engaging element may be associated with the central wire (for example, they may pass along the central wire), but they may move freely along the central wire, in at least some embodiments.

According to certain embodiments, the central wire is fixed or joined with the distal engaging element. In some occasions, the proximal end or the distal end of the distal engaging element may be joined to the distal end of the central wire. The association (i.e. connection) between the central wire and the distal engaging element may be done via various ways such as welding, gluing, or clipping on to connectors. In some embodiments, the joint between the central wire and the distal engaging element is covered by a distal element connector. Alternatively, a connecter may consist of a short outer connector tube and a short inner connector tube with the component to be fixed between the walls of tubing and filled with joint media.

In some embodiments, the central wire may comprise or in be in the form of a wire, braid, or cable. The wire may have a uniform diameter or tapered diameter, which varies from distal to proximal ends. Various materials can be used to manufacture the central wire, which may include metal and non-metal materials. Some non-limiting examples of metal materials for the central wire may comprise nickel, titanium, stainless steel, cobalt, chrome and any alloys of the foregoing such as Nitinol (NiTi), or Cobalt Chromium alloys. In addition, any polymers or plastics which have desired properties of being the central wire can be used for production of the same. Polymers include, but are not limited to, Polyimide, PEEK (Polyether ether ketone), Nylon, PTFE (polytetrafluoroethylene), PET (Polyethylene terephthalate), Polypropylene, etc. Polymer coated metal including but not limited to, PTFE coated Stainless Steel, or PTFE coated NiTi can also be used as a central wire. Also a hydrophilic coating would be applicable. Such coating can be applicable in part to reduce friction between the central wire and the tubing compartment(s). The central wire can also be made of composite materials, such as PTFE or FEP (Fluorinated ethylene propylene) tubing over NiTi wire, or PTFE or FEP tubing over Stainless Steel etc. The diameter of the central wire may range approximately from 0.001 inch to 0.1 inch. In certain embodiments, the diameter of the central wire may be about 0.001, 0.002, 0.003, 0.004, 0.005, 0.006, 0.007, 0.008, 0.009, 0.01 inch. Alternatively, the diameter of the central wire may be more than 0.01 inch.

The term "engaging compartment" generally includes elastic structure(s) that can be compressed into small profile/diameter and inserted into a body lumen through a microcatheter, and, upon being released from the microcatheter, expands to a larger diameter to engage and remove at least part of clot/occlusion in order to recanalize the blocked lumen or vessel. The engaging compartment may comprise a distal engaging element, optional middle engaging element(s), and a proximal engaging element. In some embodiments, the engaging element may comprise a plurality of wires. Engaging elements can be formed into a mesh or a braid structure in at least some embodiments. In some other embodiments, the engaging element may comprise struts made from tubing or sheet materials. The struts can be made through laser cut hypo-tubes or sheet material, or photo etched sheet materials. Heat treatment may be needed to set the struts into the desired shape, e.g. cone shapes or cylinder shapes, followed by chemical etching or electro-polishing in order to smooth the surface of the element.

The engaging elements can be made of elastic materials. Some non-limiting examples of such metal materials for engaging elements include nickel-titanium (NiTi) alloy, stainless steel, titanium and its alloys, and cobalt chrome (CoCr) alloys. Alternatively, any polymers or plastics which have desired properties for a distal engaging element can be used. In further alternative examples, the engaging elements can be constructed using two or more different materials, such as polymer coated metal materials.

In some embodiments, an overall diameter of the engaging elements may vary from approximately 1 mm to 8 mm at its expanded state. In certain embodiments, the diameter of the distal engaging elements at their expanded state may be approximately 1 mm, 2 mm, 3 mm, 4 mm, 5 mm, 6 mm, 7 mm, and 8 mm or any range there between. In some other embodiments, a length of each engaging element may vary from approximately 2 mm to 40 mm. In certain some embodiments, the length of each engaging element may be approximately 2 mm, 3 mm, 4 mm, 5 mm, 6 mm, 8 mm, 10 mm, 15 mm, 20 mm, 25 mm, 30 mm, 35 mm, and 40 mm or any range there between. Further, in alternative embodiments, the length of each engaging element may be more than 40 mm.

In some embodiments, markers (such as markers 1770 in FIG. 17A) may be added to the device. Such markers may include radiopaque materials which help monitor the position and or movement of the device in the body. Some non-limiting examples of radiopaque markers may comprise gold, gold alloys, CoCr alloy, platinum, or platinum alloys. Marker(s) can also be in form of radiopaque coating. The markers may be added anywhere in the device. In some embodiments, one or more markers may be added at the distal engaging element so that a location of the distal engaging element in the body can be determined. In some other embodiments, one or more markers may be added at the proximal engaging element so that a location of the proximal engaging element in the body would be determined. In still some other embodiments, any or all engaging elements may contain markers. Alternatively, one or more markers may be added to the central wire and/or the tubing compartment. In some embodiments, the markers may be approximately 0.10 to 4 mm long, and the diameter is approximately 0.001 to 0.030 inch. However, any variations in any dimensions (e.g. length, diameter, size, and mass) and in shapes of markers are suitable.

In some embodiments, the device may comprise one or more tubing compartments. Control tubing compartments may comprise a plurality of tubing elements. Such tubing elements may include a pusher tubing and a connecting tubing. The pusher tubing may further comprise an inner pusher tubing, an outer pusher tubing, and/or a proximal pusher tubing, and distal pusher tubing in at least some embodiments. These pusher tubing components may be attached or fixed to each other. Various materials can be used to manufacture the tubing elements, which may include metal and non-metal materials. In some embodiments, the distal pusher tubing and/or an outer pusher tubing can be made from lubricious and flexible polymers such as PTFE or PET. Relatively smaller Polyimide or PEEK tubing may be utilized when stretch resistance is required. The proximal pusher tubing can be made from Nitinol super-elastic material, stainless steels, CoCr alloys, titanium alloys, or polymers (such as Polyimide, PEEK, etc.). To reduce friction between the pusher tubing and the inner lumen of the microcatheter, one or more of the tubing elements can also be coated with lubricious material, such as PTFE coating, hydrophilic coating etc. The tubing elements can also be made of composite materials, such as PTFE or FEP (Fluorinated ethylene propylene) tubing over metal (Nitinol, stainless etc.) coil for pushability and flexibility.

The central wire, control wire, spacing wire, and connection wire can be in the form of a wire, braid, or cable. Some non-limiting examples of metal materials for the central wire may comprise nickel, titanium, stainless steel, cobalt, chrome and any alloys of the foregoing such as Nitinol (NiTi), Titanium alloys, or Cobalt Chromium alloys. In addition, any polymers or plastics which have desired properties of being the central wire can be used for production of the same. Polymers include, but not limited to, Polyimide, PEEK (Polyether ether ketone), Nylon, PTFE (polytetrafluoroethylene), PET (Polyethylene terephthalate), Polypropylene, etc. Polymer coated metal including but not limited to, PTFE coated Stainless Steel, or PTFE coated NiTi can also be used as a central wire. Also a hydrophilic coating can be applied to reduce friction between the wire and the inner lumen of pusher tubing.

In some embodiments, the outer diameter of the pusher tubing components may be approximately 0.001 inch (approx. 0.025 mm) to 0.050 inch (approx. 1.3 mm). In other embodiments, the diameter of the pusher tubing components may be smaller than 0.001 inch (approx. 0.025 mm) or over 0.050 inch (approx. 1.3 mm).

In some embodiments, the device may comprise a plurality of engaging elements such as two, three, four, five, six or more engaging elements. Therefore, in embodiments where three or more engaging elements are present in a device, there can be a distal engaging element that is located most distally among all engaging elements, a proximal engaging element that is located most proximally, and one or more middle engaging elements that are located between the distal and proximal engaging elements.

Figure 14A:
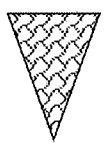
FIGS. 14A-E show still alternative, non-limiting and illustrative embodiments alternative structures of engaging elements.
Figure 14B:
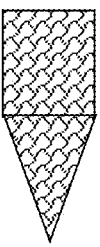
Figure 14C:
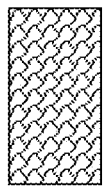
Figure 14D:
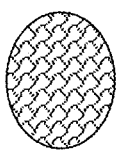
Figure 14E:

The shape, size, and structure/configuration of the engaging element are not limited and can be varied to a degree compatible with a blood vessel and suitable for treatment. In certain embodiments, the engaging element can be shaped generally in a conical or pyramid form (as shown in FIG. 14A), a cylindrical or tubular form (FIG. 14C), an ellipsoid (FIG. 14 D), or spherical form (FIG. 14D), or an umbrella (or parachute) form (FIG. 14E) etc., and combination of any of the form/shape described above. One example is shown in FIG. 14B. The engaging elements may be open or closed at either end when in a cylindrical or tubular form. Individual engaging elements present in a same device can vary from each other, e.g. in size, structure, material, and/or function. Alternatively, some or all of the engaging elements present in a same device can share one or more common features among, e.g. size, structure, material, and function.

In addition, in some embodiments, there is a connection wire that associates with two or more of the engaging elements of a device. In some embodiments, the connection wire may connect or associate with certain or some (not all) of a plurality of the engaging elements. In some other embodiments, the connection wire may associate or connect with all of the engaging elements present in the device. The association or connection between the connection wire and individual engaging elements may be fixed at a position of the connection wire. When multiple engaging elements are associated with (or connected to) a connection wire, the types of association/connection of an individual engaging element with the connection wire may vary within a single device, e.g. fixation or non-fixation manner. Thus, in some embodiments, some (not all) of the engaging elements that are associated or connected with a same connection wire may be fixed at their respective positions of the connection wire. The connection wire can be flexible, or floppy, which allows the space between engaging elements to be shortened when it is desired to bring the engaging elements closer together. In those circumstances the connection wire may be stretch resistant under tension so that the maximum distance between the engaging elements is also limited by the connection wire.

The association (including connection) between the connection wire and the engaging element, especially the fixation (or joint) there between, may be done via various ways such as welding, gluing, or clipping. There can be an additional element such as a tubing or connector where the engaging element and the connection wire are fixed thereto. The association (including connection) between the connection wire and the engaging element, especially where the engaging element can move along the central wire, can be done via various ways including a connector. For example, the engaging element may contain or be attached to a short inner element connector tubing and an outer element connector tubing. The connection wire may be attached between the walls of two tubing and the central wire may pass through (inside) the inner element connector tubing. Therefore, the engaging elements can move (slide) along the central wire without being fixed at a certain position.

In some designs, a spacing wire may also be present. Engaging elements can be fixed to the spacing wire. The spacing wire is stiffer than the connection wire and therefore does not buckle or become slack. Thus the spacing wire maintains a fixed space or distance between the engaging elements.

A connection wire and/or a spacing wire can be in the form of a round or flat wire, cable, or have a braid structure. The connection wire, in some embodiments, is flexible yet stretch-resistant. Some non-limiting examples of metal materials for the connection wire may comprise nickel, titanium, stainless steel, cobalt, chrome and any alloys of the foregoing such as Nitinol (NiTi), Titanium alloys, or Cobalt Chromium alloys. In addition, any polymers or plastics which have desired properties of being the connection wire can be used for production of the same. Polymers include, but not limited to, Polyimide, PEEK (Polyether ether ketone), Nylon, PTFE (polytetrafluoroethylene), PET (Polyethylene terephthalate), Polypropylene, etc. Polymer coated metal including but not limited to, PTFE coated Stainless Steel, or PTFE coated NiTi can also be used as a connection wire. Also a hydrophilic coating can be applied.

In certain embodiments, there can be more than one connection wire. In some of such embodiments, a connection wire may associate or connect with all of the engaging elements present in a device. Alternatively, a connection wire may associate or connect with a pair of engaging elements, such as a receiving engaging element and a capturing engaging element. In certain embodiments, there can be two, three, four, five, six or more connection wires present in a single device. In some other embodiments, a device can have seven or more connection wires.

In some embodiments, a device may comprise a proximal end control element that can associate with the most proximally located engaging element and be able to control the position of the associated engaging element(s). In certain embodiments, the proximal end control element can be a form of tubing compartment or a wire. The proximal end control element can set a boundary of the most proximal end of the engaging elements. In certain embodiments, the proximal end control element may be operably linked to a handle that can control the movement of the proximal end control element.

In some embodiments where a device comprises a plurality of engaging elements, the device may further comprise a tubing compartment that associates with (or connects to) a proximal engaging element of the device. In some embodiments, other engaging elements, besides the proximal engaging element, can be associated with (or connected to) the tubing through either a connection wire or spacing wire (both of which may help maintain a desired space between the proximal engaging elements and other engaging elements). In some embodiments, the proximal engaging element can be fixed at about the distal end of the tubing compartment via its proximal end connector. Therefore, in such embodiments, the movements of the proximal engaging element and other elements fixed to the connection wire or spacing wire are controlled by the tubing compartment.

In alternative embodiments, a device may comprise a plurality of engaging elements and also a control wire that associates with (or connects to) one or more engaging elements of the device. In some embodiments, the control wire may associate with a proximal engaging element of the device. The association (or connection) between the control wire and the proximal engaging element(s) may comprise a fixation or joint that the engaging element is fixed at a position of the control wire. Therefore, the movement of the proximal engaging element is controlled by pushing or pulling the control wire.

In certain embodiments where more than one engaging elements are associated with a control wire, each of the associated engaging elements can be fixed at its respective position on the control wire. In some embodiments where multiple engaging elements (receiving elements) are associated with the control wire, some (not all) of the associated engaging elements are fixed at their respective position on the control wire, or spacing wire via engaging element connector tubing. Those engaging elements can move along the central wire to change the spaces between the receiving elements and the capture elements.

In some embodiments, a control wire is operably linked or connected to a handle at the proximal end of the device such that an operator (e.g. a medical practitioner) can control (or mobilize) the control wire via the handle, e.g. pushing or pulling the control wire. This control operation, which controls the movement of the control wire, can result in controlling the movement of engaging elements that are associated with the control wire and the spacing wire.

A control wire can be in the form of a wire, cable, braid, or tubing. Some non-limiting examples of metal materials for the connection wire may comprise nickel, titanium, stainless steel, cobalt, chrome and any alloys of the foregoing such as Nitinol (NiTi), Titanium alloys, or Cobalt Chromium alloys. In addition, any polymers or plastics which have desired properties of being the control wire can be used for production of the same. Polymers include, but not limited to, Polyimide, PEEK (Polyether ether ketone), Nylon, PTFE (polytetrafluoroethylene), PET (Polyethylene terephthalate), Polypropylene, etc. Polymer coated metal including but not limited to, PTFE coated Stainless Steel, or PTFE coated NiTi can also be used as a control wire. Also a hydrophilic coating can be applied.

In some embodiments, individual engaging elements can be associated with (or connected to) one or more of the wires selected from the group consisting of a control wire, a connection wire, a spacing wire, and a central wire. In addition, when an individual engaging element is associated with (or connected to) at least two of the wires, the engaging element can be fixed at a position with respect to at least one of the associated/connected wire(s) while movable along the other associated/connected wire(s). Thus, for example, if an engaging element is associated with a control wire or a spacing wire or fixed to the control wire or a spacing wire, the engaging element can still be movable on the other wire.

When individual engaging element(s) are associated with (or connected to) one or more wires (e.g. a control wire, a connection wire, a spacing wire, and a central wire), by controlling one or more of such wires, the position of individual engaging element can be controlled. In addition, the space or distance between the engaging element(s) can also be adjusted via the control of their respectively associated/connected wire(s). Accordingly, while attempting to engage and contain an occlusion with the device so as to remove or treat the occlusion from a body lumen, an operator can mobilize a single engaging element or two or more engaging elements as an operation unit/pair. This complex and fine mode of operation significantly enhances the efficiency of the treatment while minimizing a risk of damaging the body lumen.

A control wire (or tubing compartment) may be separate from and not attached to a central wire and therefore move independently. In some embodiments, there are separate proximal handles that are configured to control the control wire or tubing compartment, and the central wire. The handles can act as a controller. By operating those handles and controlling the central wire and the control wire or tubing compartment, individual engaging elements of a device can be positioned in a desired location, and also the space/distance between two or more of the engaging elements can be adjusted so as to maximize the grabbing/capturing/removal of an occlusion from the body lumen. Alternatively, or in combination with a control wire or tubing compartment, and a central wire, the connection wire and, or spacing wire in certain embodiments is also able to control a space or distance between two or more engaging elements. For example, the connection wire may be separate from the central wire and control wire and move independently. Therefore it may allow the space/distance between one or more engaging elements to be shortened. When the central wire is pulled proximally or the control wire or tubing compartment is pushed distally, the space between the receiving elements and the capturing elements can be shortened so as to cinch or hold a clot. While pulling the control wire or tubing compartment proximally and holding the central wire, the distance between the capturing elements and the receiving elements increase until the connection wire is under tension. The tensioning of the connection wire allows the components of the engagement compartment to be withdrawn back into the microcatheter without elements being overlapped with each other.

In some embodiments, a device may comprise two or more engagement units/pairs in which four or more engaging elements operate together to capture/cinch an occlusion and remove it from a body lumen. In certain embodiments, the engaging unit/pair may comprise two engaging elements, one functions as a receiving element and the other functions as a capturing element. In some embodiments, a capturing element can be located distally whereas a receiving element can be located proximally in an engagement unit/pair. The capturing element may be formed in a manner that can engage (e.g. capture, or grab,) an occlusion. The capturing element can engage the occlusion directly with its proximal ends of the element body or by its wire/strut structure along any parts of the struts that come into contact with the occlusion. Alternatively, the occlusion can be frictionally engaged between a body lumen and the capturing element. Still alternatively, the occlusion can be captured, cinched or held between the capturing element and the receiving element. All of these mechanisms for capturing, engaging, cinching or holding of the occlusion may be working simultaneously to engage and remove the occlusion, e.g., part of the occlusion may be frictionally engaged with (between) the capturing element and the body lumen and some other part of the occlusion may be engaged with the receiving element. There can be various modes of capturing or engagement of an occlusion using the plurality of engaging elements and the body lumen and any of such variations are encompassed within the scope of the method and device disclosed herein.

In certain embodiments, the distal engaging element may comprise a plurality of wire or struts forming a web such that it can capture the occlusion on its own or in combination with another proximally located engaging element or receiving element and/or the body lumen. The more proximal engaging element or receiving element, although it can also be able to engage directly with the occlusion if desired or necessary via its wires or struts, can also function to ensure or strengthen the engagement of the occlusion by the more distal engaging or capturing element. For example, in certain cases where an occlusion is relative large or extends a distance along the body lumen, multiple engaging elements or multiple capturing and receiving elements (and often along with a frictional engagement with a body lumen) can act to engage the occlusion at more than one location to ensure more complete engagement of the clot. See, e.g. a non-limiting and illustrative embodiment shown in FIGS. 2B and FIGS. 9A-C. Alternatively, an individual engagement (or operation) unit/pair separately operates to remove a separate occlusion. See, e.g. a non-limiting and illustrative embodiment shown in FIGS. 9D-F. Also, alternatively or in combination with at least one of the foregoing modes, the receiving element or more proximal engaging element can move closer to the capturing element or more distal engaging element holding or cinching the clot between the two adjacent elements, which may result in a more complete or stronger capture of the occlusion. In certain embodiments, the proximal engaging elements or receiving elements may be shaped in a manner that it can conform to a proximal portion of the more distal engaging element or capturing element. In other words, the proximal portion of the distal engaging element or capturing element may fit within the distal portion of the more proximal engaging element or receiving element. Therefore, the containment of the occlusion between the two elements can be further secured during the treatment procedure and also during the removal of the device from the lumen.

In some embodiments, a device can comprise more than two operation units/pairs. Therefore, in certain embodiments, the device may comprise three, four, five, six or more operation units/pairs. In certain embodiments, the distal engaging element or the distal end of the device may not fully pass beyond an occlusion in a body lumen. Rather, the device may proceed into only part of the proximal end of the occlusion, e.g. as seen in FIG. 9A-F, and engage only part of the occlusion. For example it may be difficult or impossible to visualize how long the blockage (occlusion) extends in the lumen i.e. where the distal end of the occlusion is. In these situations it may be safer to advance the device by or within only part of the occlusion and also engage only the part of the occlusion. However, in some other occasions the device may be advanced beyond the distal end of the occlusion when it is determined that this advancement may be a safe maneuver.

In some embodiments, the position of an individual engaging element or the position of an operation unit/pair can be adjusted via movement of at least one selected from the group consisting of a central wire, a control tubing/wire compartment(s), a connection wire(s), a spacing wire(s), and a control wire(s). Generally, all the engaging elements in a device may be associated with (or connected to) a central wire. In some embodiments, only some (not all) of the engaging elements may be fixed at their respective position on the central wire whereas some other engaging elements may still be movable along the control wire. In certain embodiments, all the capturing elements of the device (from different operation units/pairs) may be fixed at their respective position in the central wire whereas all the receiving elements may be movable along the central wire For the purpose of illustration, some non-limiting and illustrative examples of the device according to the invention are provided in the following figures. While only few exemplary applications are described herein for the purpose of illustration, many different modifications and alternations, which should be obvious to a person with ordinary skill in the art based on the disclosure herein, can also be done without affecting the scope of the invention. Therefore, not only the examples disclosed in this application but also such obvious modifications and alterations should also be included in the scope of the invention.

Figure 1B:
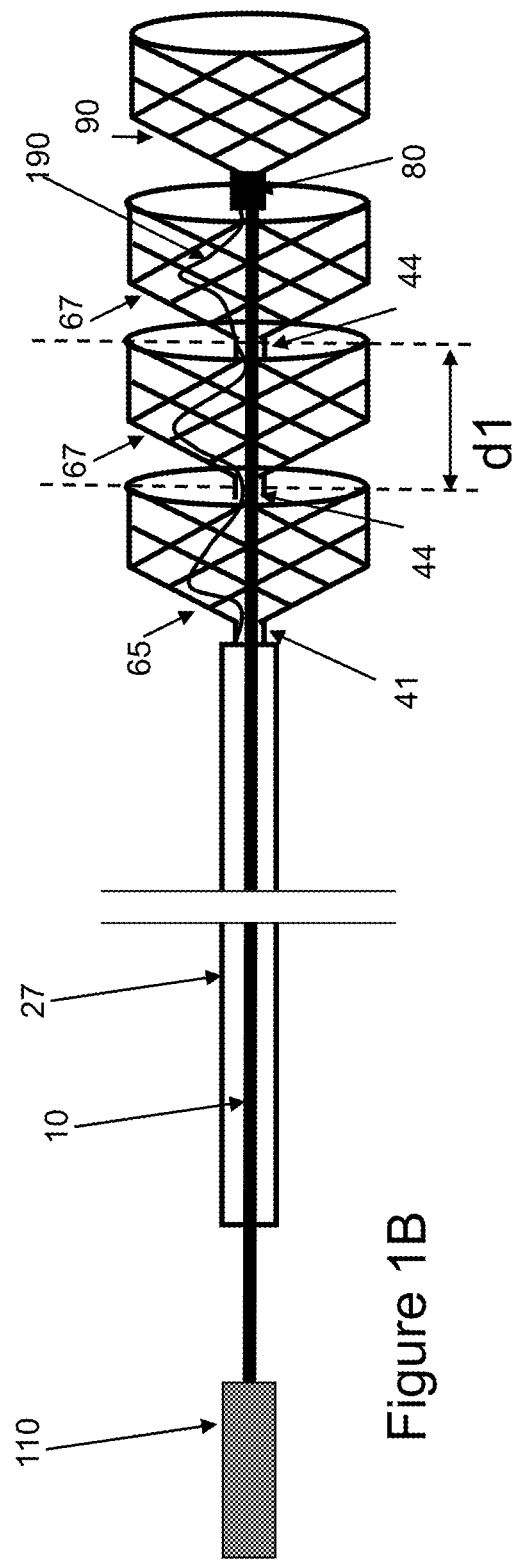

FIG. 1 illustrates one embodiment of a device where the device may comprise a plurality of engaging elements. In some embodiments, the device may comprise three or more engaging elements. In some embodiments, the device may comprise a central wire (10), a tubing compartment (27), three or more engaging elements (65, 67, 90), a connection wire (190). This figure shows four engaging elements, including a distal engaging element (90), a proximal engaging element (65), and two middle engaging elements (67). In this example the most distal engaging element (90) functions as a capturing element and all the engaging elements proximal to this may function as either capturing elements and/or receiving elements. The individual engaging element may vary from 3-25 mm in length when extended. FIG. 1A is the in its open state, with spaces between each adjacent engaging element being fully open, the length of the space being marked as "d". FIG. 1B is at its closed state, with the spaces between each engaging elements being shortened (from "d" to "d1") for the purpose of holding, cinching or grabbing the occlusion or clot.

In some embodiments, all the multiple engaging elements (65, 67, and 90) are associated with (or connected to) the central wire (10). Of these engaging elements, the proximal end of the distal engaging element (90) can be fixed to the distal end (or tip) of the central wire (10) whereas the other three engaging elements (65 and 67) can freely slide on the central wire. Also, all the multiple engaging elements can be associated with the connection wire (190). In some embodiments, the flexible connection wire (190) can link proximal ends of all engaging elements at pre-set or equal space there between. In such embodiments, the engaging elements are fixed at their respective positions on the connection wire and maintain that distance with certain maneuvers. In addition, in some embodiments, the proximal end of the proximal engaging element (65) can be fixed to the distal end of the tubing compartment (27). The central wire can freely slide inside the tubing compartment. In certain embodiments, the device may further comprise or operably link to a handle (110) at the proximal end of the device, so that it can control (e.g. push or pull) the central wire.

FIGS. 2A-2C illustrate another embodiment of a method where a device comprising a plurality of engaging element such as that illustrated in FIG. 1 is used to remove or treat an occlusion/clot in a body lumen.

In some embodiments, the device can be introduced into blood vessel through a microcatheter (30). Upon arrival at the occluded site in the body lumen, and when pushing the device through the microcatheter (30), the distal engaging element (90) may first be pushed forward with the central wire (10). Continued pushing force on the central wire (10) can maintain the connection wire(s) under tension, and pull each engaging element that is associated with the connection wire (190) forward along the microcatheter lumen. In addition, continued forward pushing force while retracting the microcatheter (30) would allow the operator to unsheathe the device and maintain a set distance between the engaging elements. Because the connection wire (190) may be flexible, but is generally not stretchable, it allows the engaging elements to move closer to each other when the connection wire (190) is slack, but prevents the engaging elements from being separated more than a preset distance when the connection wire (190) is under tension. The engaging elements, upon being unsheathed from the microcatheter (30), can be positioned with the pre-set distance there between.

Upon unsheathing the microcatheter (30), the central wire (10) may be held stable so that the distal engaging element (90), which is fixed at the distal end of the central wire (90), can be stabilized. The friction between the inner lumen of the microcatheter (30) and the surface of the engaging elements (65 and 67) can cause the freely sliding engaging elements to move backward; however, because the connection wire (190) is not stretchable, the connection wire (190) holds the pre-set space between each element. After unsheathing the microcatheter (30), the engaging elements may self-expand. An operator can adjust the spaces between the engaging elements as described below. To engage or hold the clot, an operator may shorten the space between the engaging elements (i) by pulling the central wire (10) backward (proximally) while holding the tubing compartment (27) stable, (ii) by pushing the tubing compartment (27) forward (distally) while holding the central wire (10) stable, or (iii) by pulling the central wire (10) backward (proximally) and pushing the tubing compartment (27) forward (distally). This adjustment of the position of the engaging elements and the space there between can allow at least part of the clot to be compressed/cinched or caught in the space gap. See, e.g. FIGS. 2B-2C. Alternatively or in combination, the occlusion can be immobilized via the frictional engagement with the body lumen and one or more engaging element(s). The occlusion can also be directly engaged with the wires or struts of the engaging elements. Also, the occlusion can be immobilized and captured between one or more engaging element(s) and the body lumen. See, also, e.g. FIGS. 2B-2C. In some embodiments, the engagement (capture) and containment of the occlusion may involve more than one mode. Therefore, for example, at least part of the occlusion may be captured by direct engagement with one or more engaging elements and also at least some other part of the occlusion may be captured between the space(s) of two or more engaging elements. Also, alternatively or in combination, some part of the occlusion can be frictionally captured and immobilized by the body lumen and the engaging element(s).

In some embodiments, during the treatment procedure, while holding the tubing compartment (27), the central wire can be pulled proximally. The distal engaging element then may move backward and cinch or hold the clot with the adjacent engaging element(s). The proximal and/or its adjacent engaging elements are then pushed backward (proximally) by the compressed clot, which can in turn compress and cinch the occlusion. The operator can shorten the distance between the engaging elements until the occlusion is securely cinched/grabbed by the device. The modes of securely cinching/grabbing the occlusion may include one or more of the following: (1) the occlusion may be cinched or held between the engaging elements, (2) the occlusion may be directly engaged with the wires or struts of one or more engaging elements, (3) the occlusion may be frictionally contained between the body lumen and one or more of the engaging elements, and/or (4) the occlusion may be frictionally contained between the body lumen and the space(s) between the engaging elements, Once the occlusion is believed to be securely grabbed or cinched by the device, the device can then be pulled out of the body lumen. In some embodiments, such as shown in FIG. 1B and FIG. 2C, the connection wire (10) may be thin and flexible and thus can bend, curl or bow once when the distance between the engaging elements is shortened.

Figure 3:
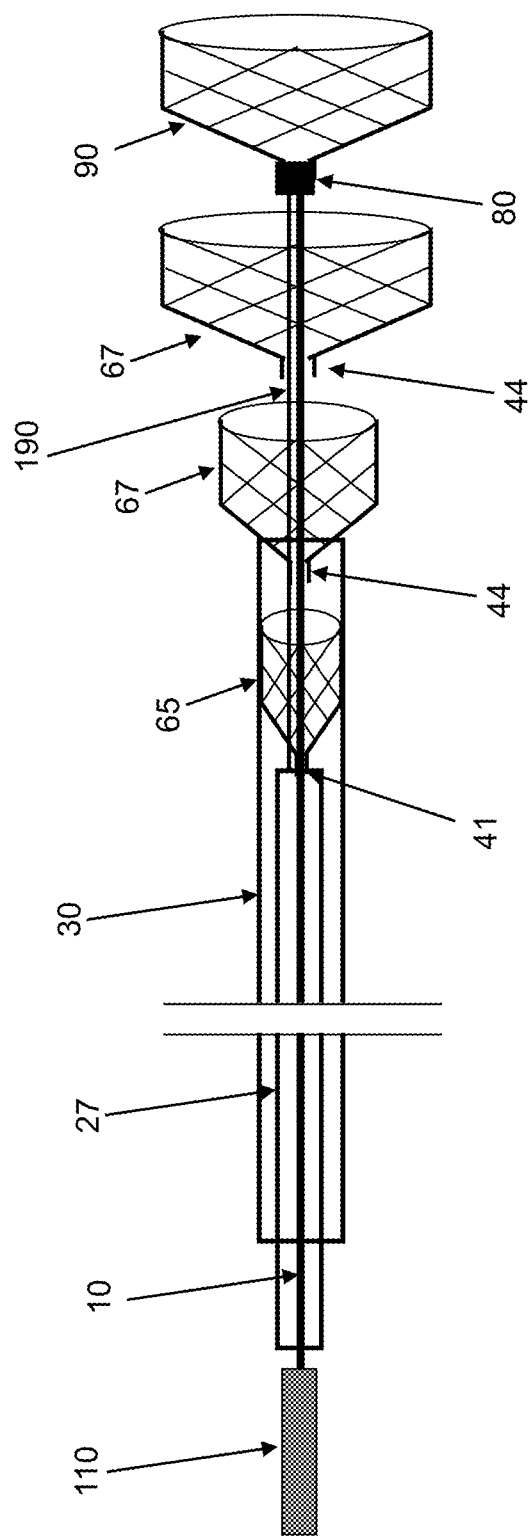
FIG. 3 shows still another non-limiting, illustrative example of a device according to some embodiments of the invention where the device comprises a plurality of engaging elements and a connection wire connecting the engaging elements. The device may be delivered through a microcatheter into the body lumen. This figure also shows that the device can be configured to be retrieved back to the microcatheter without elements overlapping each other.

FIG. 3 illustrates another embodiment of a device where the device may comprise a plurality of engaging elements. In some embodiments, when the device needs to be withdrawn into a microcatheter (30) during a retrieval procedure, the tubing compartment (27) can be pulled backward. The proximal engaging element (65) which is fixed to the tubing compartment can be pulled into the microcatheter (30). When the connection wire (190) is maintained under tension, it pulls the engaging elements that are connected to the connection wire into the microcatheter one by one. This retrieval mechanism allows the connection wire to extend to the pre-set distance between the engaging elements and prevents the plurality of engaging elements from stacking up on each other so that they can be pulled back into the microcatheter. The stacked up engaging elements may have too large a diameter to fit in the microcatheter and they may also be damaged when pulled into a position in which they are stacked up.

Figure 4:
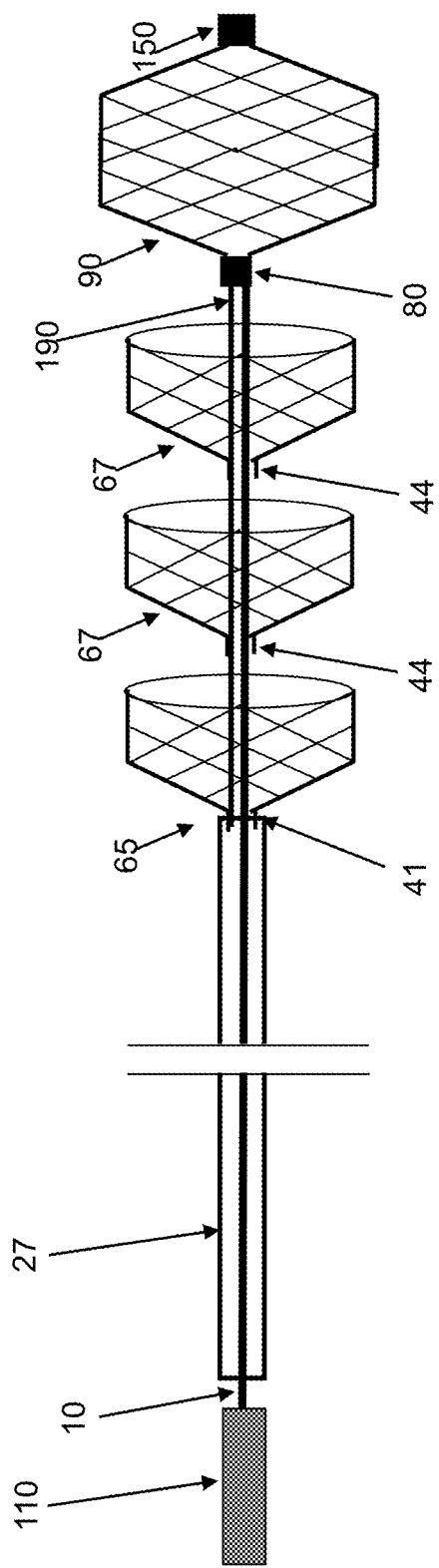
FIG. 4 shows still another non-limiting, illustrative example of a device according to some embodiments of the invention where the device comprises a plurality of engaging elements. In this particular embodiment, the distal engaging element of the device may have a closed end at its distal end. In addition, the distal engaging element may be larger in size (length and diameter) than the other engaging elements. However, the stiffness of the distal engaging element can be less than that of the other engaging elements to avoid vessel damage.

FIG. 4 illustrates still another embodiment of a device where the device may comprise a plurality of engaging elements. In some embodiments, the device may further comprise a distal engaging element (90) that also may function as distal filter. In certain embodiments, the distal end (or tip) of the distal engaging element can be closed by the distal connector (150). In some embodiments, the profile of the distal engaging element (90) can be larger in size (length and diameter) than that of other engaging elements and is less stiff than the other engaging elements. This can minimize radial force of the distal engaging element against the vessel wall. This distal engaging element, especially in a distal filter form, can prevent clot debris from going downstream. If the clot (or occlusion) fragments during the treatment procedure, and generates debris, the debris can be caught (collected or contained) by this distal filter element (90). Since the profile of the distal engaging (filter) element is large, preferably slightly larger than the diameter of the vessel in the retrieval pass, the debris may not be able to escape between the engaging element and the wall of the vessel. In this embodiment the distal engaging element can also function to cinch or hold clot with the more proximal adjacent engaging element.

In addition, in certain embodiments, the proximal end or the distal end of the distal engaging element can be fixed to the central wire (10). Also, there can be a flexible connection wire (190) that links (associates or connects) the other engaging elements. In some of such embodiments, all the engaging elements are fixed at their respective positions on the connection wire (190), thereby setting spaces between each engaging element. In some embodiments, the proximal engaging element (65) can be fixed at about the distal end of the tubing compartment (27). With this configuration, when the tubing compartment (27) is pushed or pulled, the position of the proximal engaging element can also be adjusted. When the connection wire is under tension, the middle engaging elements can be pulled proximally by the tubing compartment, and pushed distally by the central wire).

In some other embodiments, all the engaging elements are associated with (or connected to) the central wire (10). In certain embodiments, only some (not all) engaging elements are fixed to the central wire whereas some others are able to move freely on the central wire. Therefore, for example, the distal engaging element (90) of FIG. 4 can be fixed at a position of the central wire whereas the proximal engaging element (65) and the middle/intermediate engaging elements (67) can freely slide on the central wire. With this configuration, the distal engaging element can be further controlled upon pushing or pulling the central wire via a handle (110) by an operator, and this can position the most distal extent of the device. Once the distal engaging element is positioned, the operator can further adjust the position of other engaging elements and the distance/space between the engaging elements by controlling the connection wire (190) via controlling the tubing compartment (27).

FIGS. 5A-D show detailed structure, especially the connectors of the device according to some embodiments of the invention. FIG. 5B shows that the proximal engaging element is fixed to the distal end of the tubing compartment by a connector (41) which consists of an outer connector tubing (43) and an inner pusher tubing (21). The connection wire (190) and legs of the proximal engaging element (40) are fixed/bonded in between the wall of the two portions of tubing with joint media (42). Similarly, FIG. 5C shows the middle engaging element connector (44). The connection wire (190) and the legs of the middle engaging element (40) are fixed/bonded in between the wall of the two connector tubing portions with joint media (42). FIG. 5D shows the distal connector (80) joins the distal tip of the central wire (10), the connection wire (190), and the legs (40) of the distal engaging element (90) with a short outer v. (43) filled with joint media (42). The central wire (10) passes the hollow space of the inner connectors (21 and 45), allowing the proximal and middle engaging elements (65, 67) sliding freely over the central wire.

Figure 6:
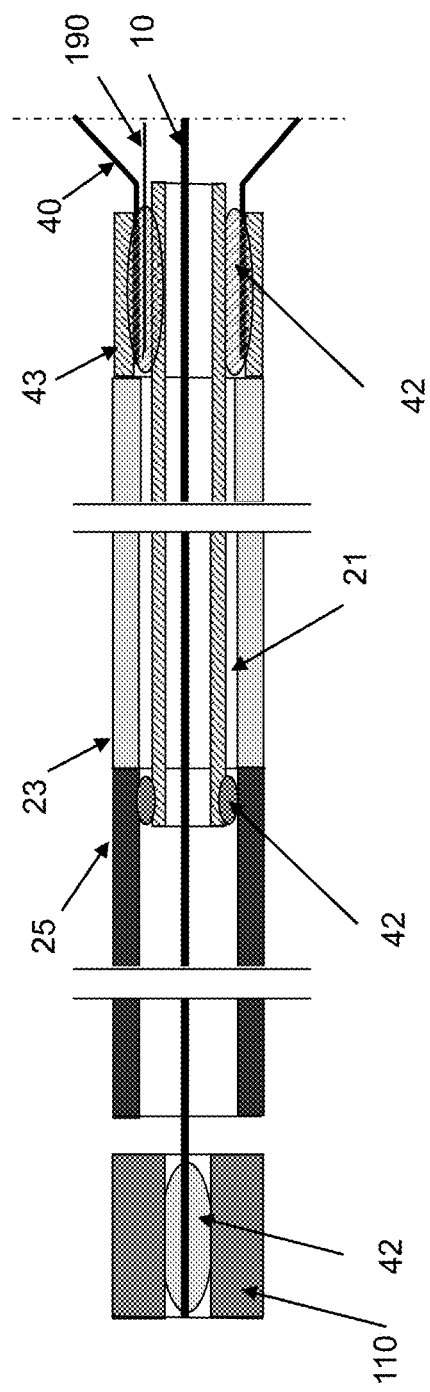
FIG. 6 shows still another non-limiting, illustrative example embodiment of a device according to some embodiments of the invention where the device comprises a plurality of engaging elements. A non-limiting structure and components of a tubing compartment, central wire handle, and connections among components are illustrated in this figure.

FIG. 6 shows a non-limiting, illustrative structure of a tubing compartment according to some embodiments of the invention. The tubing compartment may comprise or consist of three major components, the inner distal pusher tubing (21), the outer distal pusher tubing (23) and the proximal pusher tubing (25). All are bonded/connected by joint media (42). This figure also shows that the proximal end of the central wire is jointed to a handle (110) by joint media (42). The distal pusher tubing (21, 23) is generally flexible so that the device can pass tortuous segment of a vessel. The proximal pusher tubing (25) is stiff to ensure the device can be pushed through microcatheter.

FIGS. 7A-C illustrate still another embodiment of a device where the device may comprise a plurality of engaging elements. In some embodiments, the device may comprise a central wire (10), a control wire (100), and a plurality of self-expandable engaging elements, each of which can be about 2 to about 25 mm long or longer longitudinally. The length of the individual engaging elements when expanded, which can be identical, similar or different from each other, can be about 1 mm, about 2 mm, about 4 mm, about 5 mm, about 6 mm, about 7 mm, about 8 mm, about 9 mm, about 11 mm, about 12 mm, about 13 mm, about 14 mm, about 15 mm, about 16 mm, about 17 mm, about 18 mm, about 19 mm, about 20 mm, 21 mm, 22 mm, 23 mm, 24 mm, and 25 mm, In some embodiments, the length of the individual engaging elements when expanded, which can be identical, similar or different from each other, can be about 25 mm or longer.

The proximal end of the distal engaging element (90) can be fixed at about the distal end of the central wire (10), the structure of the connection is the same as that already illustrated in FIG. 5D. The proximal end of the proximal engaging element (65) and the connection wire (190) can be fixed at about the distal end of the control wire (100) by the proximal end connector (41) consisting of an outer connection tubing (43), an inner connection tubing (45) and joint media (42) as shown in FIG. 7B. The middle/engaging elements are fixed to the connection wire (190) through connector 44 as shown in FIG. 7C, the structure of the connection is the same as and already described previously in FIG. 5C. The proximal connector (41) and the middle connector (44) can freely slide on the central wire (10). In some embodiments, a thin flexible connection wire (190) links the proximal ends of all engaging elements with a pre-set or equal space/distance between each adjacent element. In certain embodiments, the distal segment of the control wire can be tapered down into a thin more flexible section and serve as connection wire. In such case, the proximal end of the proximal engaging element can be directly joined to the control wire where the thin section starts, as shown in FIG. 7C (i.e. the connection wire 190 is a segment/part of the control wire 100). The control wire (100) may have a handle (120) attached at the proximal end of the device. The central wire can freely slide inside the handle tube and the connector at the tip of the control wire, as well as the middle connectors. In addition, the device can have a separate handle 110) that can control the movement of the central wire.

In some embodiments, all the engaging elements are fixed at their respective positions on the connection wire (100), thereby setting a pre-set space/distance there between. On the other hand, while all the engaging elements can be associated with (or connected to) the central wire (10), only the distal engaging element (90) may be fixed at the central wire (10) and the other engaging elements may be able to freely move along the central wire. In some of such embodiments, upon controlling one or both of the central wire and control wire, the position of each the distal and proximal engaging element and the space there between can be adjusted in order to securely cinch or grab an occlusion/clot.

Figure 8A:
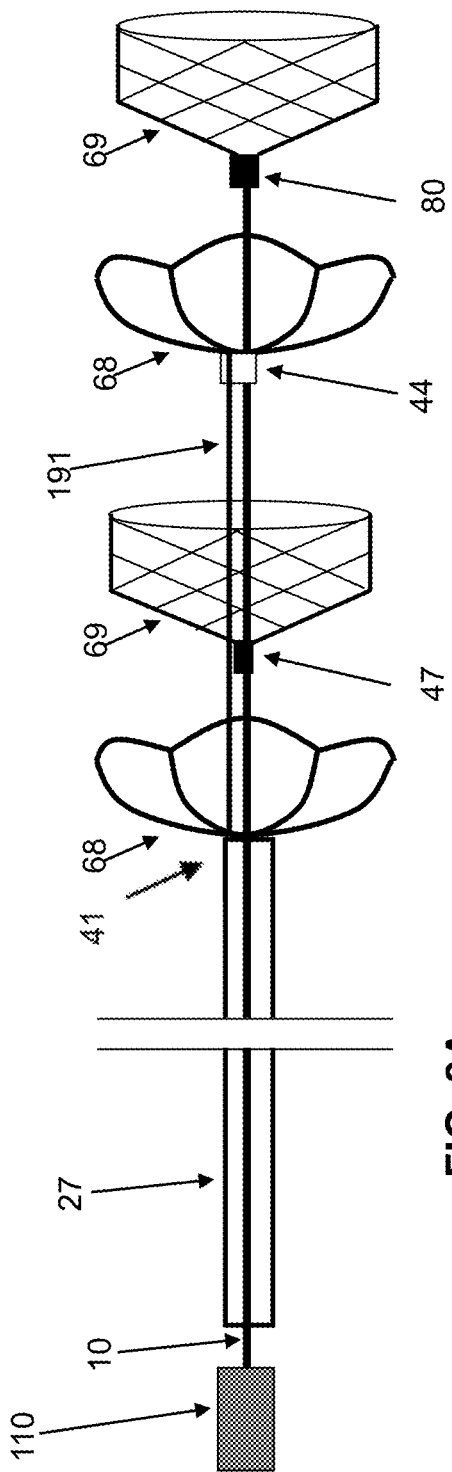
FIG. 8A shows still another non-limiting embodiment of a device according to the invention where the device comprises a plurality of engaging elements. Among the plurality of engaging elements, some of them are configured to function as a receiving element whereas some other are configured to function as a capturing/cinching element. Each receiving element and a capture element form an engaging unit/pair. In certain embodiments, the receiving elements may be associated with or connected to a spacing wire. The spacing wire and the proximal end of the proximal element are connected to a control tubing compartment. In some embodiments, a pair of a receiving element and a capturing element may function as an engaging unit/pair. In certain embodiments, the device may comprise a plurality of engaging units/pairs.
Figure 8B:
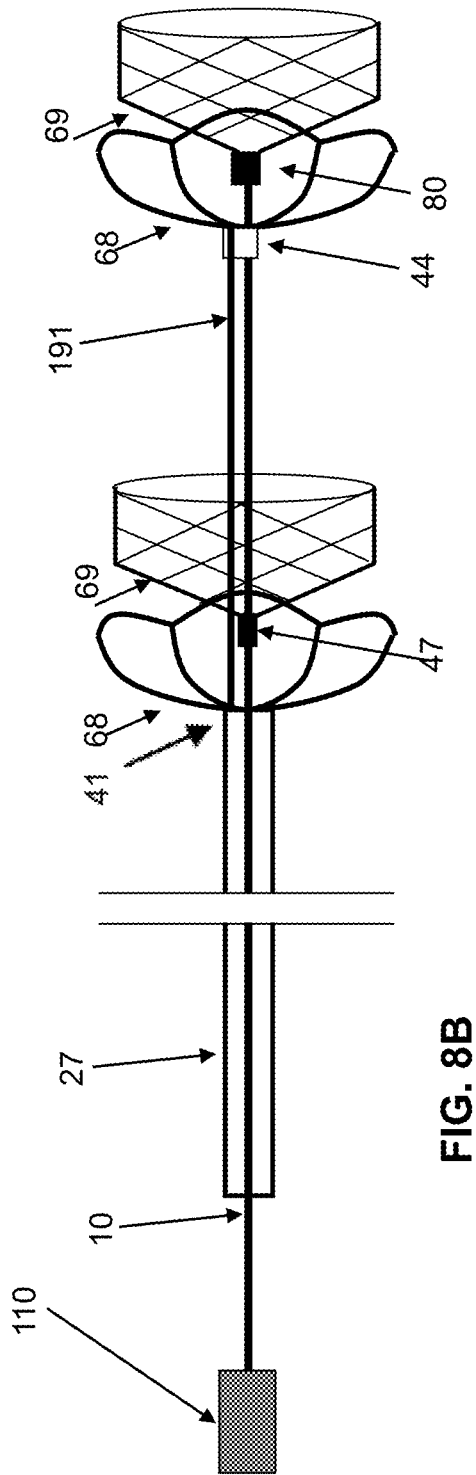
FIG. 8B shows the engagement units/pairs are closed, i.e. the spacing between the capture engaging element and receiving engaging elements are shortened.

FIGS. 8A-F illustrate still another embodiment of a device where the device may comprise a plurality of engaging elements. In some embodiments, the device may comprise a plurality of engaging elements some of which may form an engaging (or operation) unit/pair. The receiving element is connected with the spacing wire (191), which may be stiffer than the connection wire (190) describe previously. The spacing wire will not be as flexible or soft so that it cannot fold/bend under compression and therefore remains elongated. FIG. 8A shows the distance in between the receiving and capturing engaging elements is being fully opened and FIG. 8B shows the space is shortened. FIGS. 8D, 8E, 8F show the detailed structure of the proximal receiving engaging element connector (41), the middle capturing engaging element connector (44), and the distal capturing engaging element connector (80), respectively. In some embodiments, the device may comprise a central wire (10), a tubing compartment (27), and a plurality of operation unit/pair. In some embodiments, the device may comprise two or more pairs of clot cinching self-expandable engaging elements (each pair comprising 68 and 69 is considered as one operation unit/pair). In each operation unit/pair, there can be at least two or more engaging elements, at least one being a receiving element (e.g. a proximal, receiving element and a middle receiving element (68)), and at least another being a capturing element (e.g. a middle, capturing element and a distal capturing element (69)).

In certain embodiments, the capturing element may comprise a plurality of wires or struts that can directly engage with an occlusion. Alternatively or in combination, the capturing element can cinch or grab the occlusion via the frictional engagement with a body lumen and/or within the space between the capturing element and the other engaging (receiving or capturing) element. The capturing element, in at least some embodiments, has a closed end at its proximal end. The open end of the catching elements can either face distal or proximal side of the device. In some embodiments, all of the capturing elements (from different operation units/pairs) can be fixed to the central wire (10) via connectors (47, 80) and the receiving elements are fixed to a spacing wire (191) via connectors (41, 44) while the capturing elements may not be connected to the spacing wire. The receiving element can be located proximal to the capturing element and may be shaped in a manner that conforms to the shape of the capturing element which is distal to it. Therefore, in some embodiments, the proximal portion of a capturing element can fit within the distal portion of its proximally located receiving element In certain embodiments, the most proximally located receiving element (68) may be fixed to the distal end of the tubing compartment (27). In addition, all receiving elements can also be fixed at their respective positions of the spacing wire (191). Thus, the spacing wire may connect all the receiving elements (68), keeping the distance between receiving elements. Therefore, in such a configuration, by controlling the tubing compartment, the positon of all the receiving elements can also be controlled while maintaining the distance there between due to the pre-set distance set by the association with the spacing wire.

In some embodiments, some or all of the capturing elements (from different operation units/pairs can be fixed to the central wire (10). The central wire can freely slide inside the tubing compartment (27) as well as inside the connectors of the receiving engaging elements. With this configuration, the position of all the capturing elements can be controlled via the movement of the central wire.

Accordingly, in some embodiments, the position of the engaging elements can be controlled by the movement of the central wire and/or the tubing compartment. For example, the spaces between the receiving elements and capturing elements can be controlled by sliding the central wire in the tubing compartment. Alternatively or in combination, the pushing or pulling of the tubing compartment can also result in lengthening or shortening the distance between the receiving elements and capturing elements.

FIGS. 9A-F illustrate still another non-limiting embodiment of a method according to the invention where the device illustrated in FIGS. 8A-F is used to treat or remove one or more occlusion(s) from a body lumen.

In some embodiments, the device may be introduced through a microcatheter (30), by pushing the central wire (10) and the tubing compartment (27). See FIGS. 9A and D. The spacing wire (191) can maintain spaces between the receiving elements (68). The catching elements (69) can all be fixed to the central wire (10). Upon unsheathing (see FIGS. 9B and E), the engaging elements may expand and foreshorten increasing the distance between the operation units/pairs and also between the individual engaging elements. The distance between engaging elements as well as different operation units/pairs will allow an occlusion (clot) to lodge in the space gaps. While holding the tubing compartment (27) stable and pulling the central wire proximally (see FIGS. 9C and F), the catching elements (69) are moved backward. The spaces between the catching and receiving elements are all shortened and part(s) of the occlusion lodged in the spaces between the engaging elements are cinched/grabbed or held. The device can then be pulled out from the body lumen (e.g. a blood vessel).

In certain embodiments, e.g. as shown in FIGS. 9A-C, a relatively large or long length of occlusion can be treated or removed by the device comprising a plurality of operation units/pairs. In some of such occasions, more than one operation unit/pair can involve cooperatively to cinch and grab the occlusion. Alternatively or in combination, more than one occlusion can be individually treated or removed by a separate operation unit/pair as illustrated in FIGS. 9D-F. Already explained elsewhere in the application, the mechanism of cinching or grabbing (engaging, capturing or containing) the occlusion by the device can be various, e.g. (1) the occlusion may be captured within the spaces between the engaging elements, (2) the occlusion may be directly engaged with the wires or struts of one or more engaging elements, (3) the occlusion may be frictionally contained between the body lumen and one or more of the engaging elements, and (4) the occlusion may be frictionally contained between the body lumen and the space(s) between the engaging elements.

Figure 10:
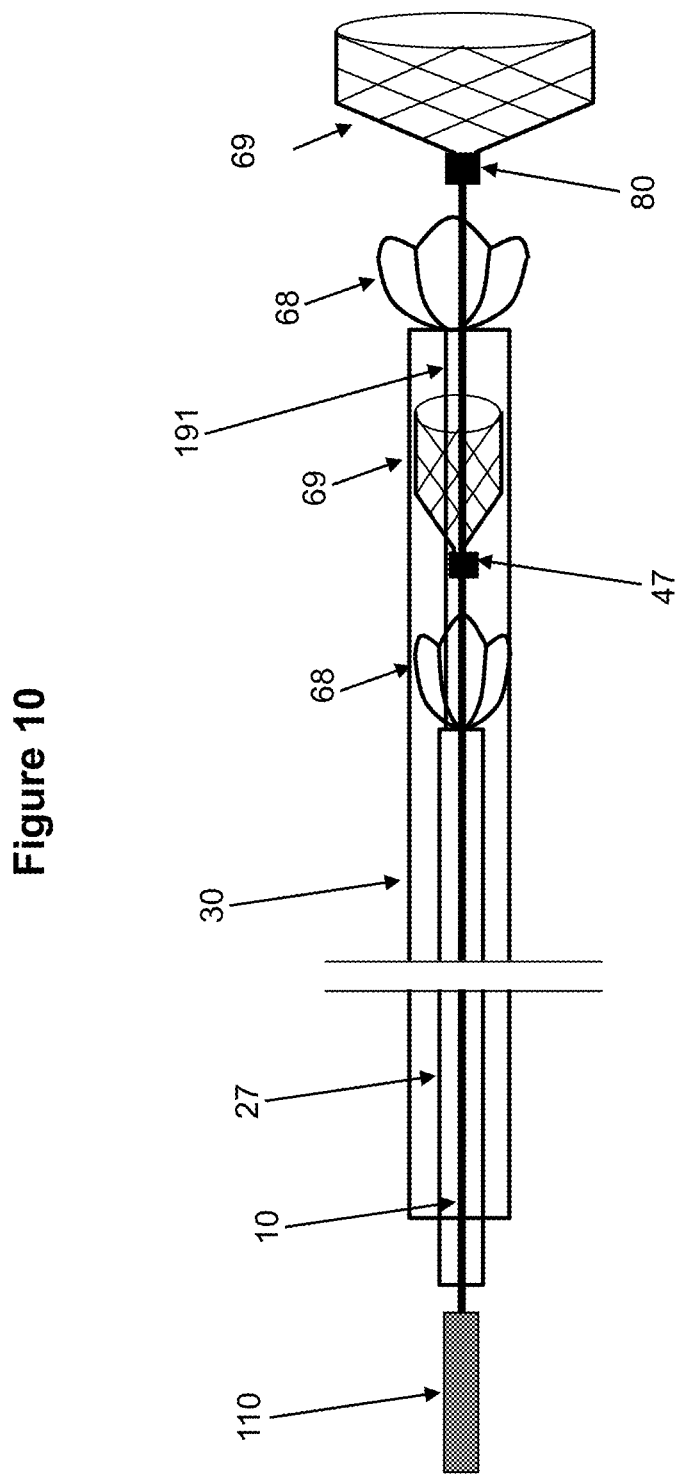
FIG. 10 shows still another non-limiting embodiment of a device according to the invention where the device comprises a plurality of engaging elements, some of which may function as a receiving element whereas some other of which may function as a capturing/cinching element. This figure shows the engaging elements are pulled back into a microcatheter when there is a need during operation.

FIG. 10 illustrates still another embodiment of a device where the device may comprise a plurality of engaging elements. In some embodiments, when the device needs to be withdrawn back into a microcatheter (30) during a retrieval procedure, the tubing compartment (27) can be pulled backward, allowing the spaces between receiving elements and catching elements to increase to prevent them from stacking up on top of each other. Thus all engaging elements can be pulled into the microcatheter.

FIGS. 11 A and B illustrate still another embodiment of a device where the device may comprise a plurality of engaging elements. As an alternative design of the device, in addition to a plurality of operation unit/pair, the device may further comprise an additional element (90) at the distal end of the device. This additional element may function as a distal filter. In certain embodiments, the distal end of the distal filter element can be closed by a distal connector (150) to more efficiently capture the clot debris. In some embodiments, the profile of the distal filter element (90) in size and diameter can be larger than that of other engaging elements and is less stiff than the other engaging elements. This can minimize radial force of the distal filter element against the vessel wall. This most distal engaging element (90) can serve to both cinch/grab the clot or occlusion and act to catch or filter clot debris. Therefore if the clot (or occlusion) breaks down during retrieval procedure, and generates a plurality of debris, the debris can be caught (collected or contained) in this distal filter element. Since the profile of the distal engaging (filter) element is large, preferably larger than the diameter of the vessel the debris may not be able to escape between the engaging element and the wall of the vessel. In FIGS. 11A-B, "*" represents where the capturing elements (69) may be fixed to the central wire (10) and "*" represents where the receiving elements (68) may be fixed to the spacing wire (191) in some embodiments.

FIGS. 12A-E illustrate still another embodiment of a device where the device may comprise a plurality of engaging elements. In some embodiments, the device may comprise a central wire (10), a control wire (100), and a plurality of operation unit/pair, e.g. each unit/pair comprising two, or more pairs of clot engagement elements. In each of the engagement operation unit/pair, at least one receiving element and one capturing element may be present, and generally the receiving element may be located proximal to the capturing elements. In some embodiments, some or all of the (proximal and intermediate) receiving elements (68) may be fixed to the control wire (100). In some other embodiments, the (distal and middle) capturing elements (69), can be fixed to the central wire (10) via connector (47, 80). In certain embodiments, the proximal and middle receiving element (68) can be associated with (or connected to) the central wire (10) but freely slide on the central wire.

FIG. 12 illustrates still another embodiment of a device where the device may comprise a plurality of engaging elements. In some embodiments, the device may comprise a central wire (10), a control wire (100), and a plurality of operation unit/pair, e.g. each unit/pair comprising two, or more pairs of clot engagement elements. In each of the engagement operation unit/pair, at least one receiving element and one capturing element may be present, and generally the receiving element may be located proximal to the capturing elements. In some embodiments, some or all of the (proximal and intermediate) receiving elements (68) may be fixed to the control wire (100). In some other embodiments, the (distal and middle) capturing elements (69), can be fixed to the central wire (10) via connector (47, 80). In certain embodiments, the proximal and middle receiving element (68) can be associated with (or connected to) the central wire (10) but freely slide on the central wire.

In certain embodiments, the control wire (100) may have a handle (120, e.g. a type of tube) attached at the proximal end of the control wire, and the central wire can freely slide inside the handle tube lumen. In addition, the central wire (10) may also be operably linked to a handle (110). Therefore, by controlling one or both of the control wire and the central wire, the space between the engaging elements can be adjusted so as to maximize the engagement and containment of an occlusion by the device.

FIGS. 12A and B show the adjustment of the distance between the engaging elements. For example, in the embodiment of FIG. 12B, while holding the control wire handle and pulling the central wire (10) proximally, the capturing elements (69) will move backward, shortening the distance between their receiving elements. When pulling the central wire back (i.e. proximally), the distance between the catching and receiving element will shorten, cinching or grabbing the clot at various points. As apparent from the illustration, e.g. conversely, by pushing the control wire distally, the receiving elements will move forward (distally), thereby the distance between the engaging elements will shorten. Therefore, by controlling the movements of the central wire (10) and/or the control wire (100), the position of both the capturing and receiving elements can be adjusted, thereby increasing or shortening the space between the engaging elements.

FIGS. 12C to E show certain, non-limiting embodiments of a connector such as (41) and (44) where the engaging element, especially a receiving element, is configured to move along the central wire but fixed to the control wire. In certain embodiments, a short outer connector tubing (43) and a short inner connection tubing (45), as well as joint media (42) can be used to join the control wire (100), the legs of the distal receiving element (40). The central wire can freely slide inside the inner connector tube (45). All capturing elements are fixed to the central wire via connector (47, 80)

The control wire and spacing wire can be from the same wire, which may be tapered down at the distal segment that serves as a spacing wire to ensure enough flexibility of the engagement compartment. Therefore, in some embodiments, as shown in FIG. 12E, the control wire (100) functions as a spacing wire (190) in the distal portion of the device.

FIGS. 13A-F illustrate still alternative embodiments of a device where the device may comprise a plurality of operation unit/pair. In some embodiments, all receiving elements (68) are free-sliding on the central wire (10) and all catching elements (69) are fixed to the central wire via connectors (47, 80), forming multiple pairs of cinching units/pairs. In each of the engaging operation units/pairs, at least one receiving element and one capturing elements may be present, and generally the receiving element may be located proximal to the capturing elements. In some embodiments, a relatively thick or more rigid, spacing wire (191) may connect all receiving elements (68) to maintain the space between them. Each unit/pair of capturing element (69) and receiving element (68) can be connected to a connection wire (190). All receiving elements can freely slide on the central wire (10). As shown in FIG. 13D, the proximal connector (41) connects a spacing wire (191), a connection wire (190) and the legs (40) of proximal engaging element in between an outer and inner connection tubes filled with joint media (42). FIG. 13E shows the detailed structure of the receiving engaging element connector (44). It connects a connection wire (190) and the legs (40) of a receiving engaging element in between an outer connection tube (43) and an inner connection tube (45) filled with joint media (42). FIG. 13F shows a similar structure of connector (44) connecting a spacing wire (191), a connection wire (190), and the legs of receiving engaging element in between an outer connector tube (43) and an inner connection tube (45) filled with joint media (42). The central wire can slide freely inside the inner connectors (45). In such embodiments, the capturing elements (69) may be fixed to the central wire via connectors (47 and 80) and the connection wire (190). All the receiving elements are fixed to the spacing wire via connectors (41 and 44).

In addition, the connection wires (191) link each pair of capturing and receiving elements in a same engaging/operation unit/pair to maintain the pre-set space between the paired engaging elements, especially when introducing device through a microcatheter (30). After unsheathing, and pulling the central wire backward, the distance between the receiving and capturing elements can be reduced and an occlusion (clot) can be cinched, grabbed or held in between the engaging elements. When pulling back the device into the microcatheter, the connection wires (190) buckle; elements of each pair may overlap, however, the profile, or the struts of the distal end of the catching element as well as the receiving element can be designed to be small. Therefore if the two engaging elements stack up, they will still be smaller than the diameter of the microcatheter. Thus the device can be retrieved back into the microcatheter. In certain embodiments, the microcatheter can serve as a stopper of all the receiving elements when catching the occlusion (clot) by pulling back the central wire and the catching elements. The advantage of this design is that there is only one handle at the proximal end of the device. An operator only needs to pull the central wire back to shorten the spaces between the receiving and catching elements to cinch a clot. The position of the engaging element will be self-adjusted and clot will be engaged and held.

FIGS. 14 A-E shows non-limiting structures of the engaging element. Alternatively the engagement can be in the form/shape of, but not limited to, conical (FIG. 14A), sphere (FIG. 14D), ellipsoid (FIG. 14D), parachute (FIG. 14E), cylinder (FIG. 14C), or any combination of above structures (e.g. as shown in FIG. 14B). The cylindrical form may also be closed or open at either the distal or proximal ends.

FIGS. 15A-B show alternative, non-limiting illustrative embodiments of structures that may form into engaging elements. The engaging elements may have proximal legs (40) and actual engaging element struts (50). The device according to some embodiments of the invention can be manufactured by a variety of techniques that are known in the art. For example, the engaging element/struts can be fabricated from a thin sheet by laser cutting or photo etching process. Alternatively, the engaging elements can also be fabricated from a piece of hypo tube material by laser-cutting. The struts shown in FIGS. 15A-B or laser cut hypo-tube may be heat set into a desired shape and size of the engaging element and further chemically polished or electro-polished. The component can be assembled into a retrieval device described in this article.

Figure 16A:
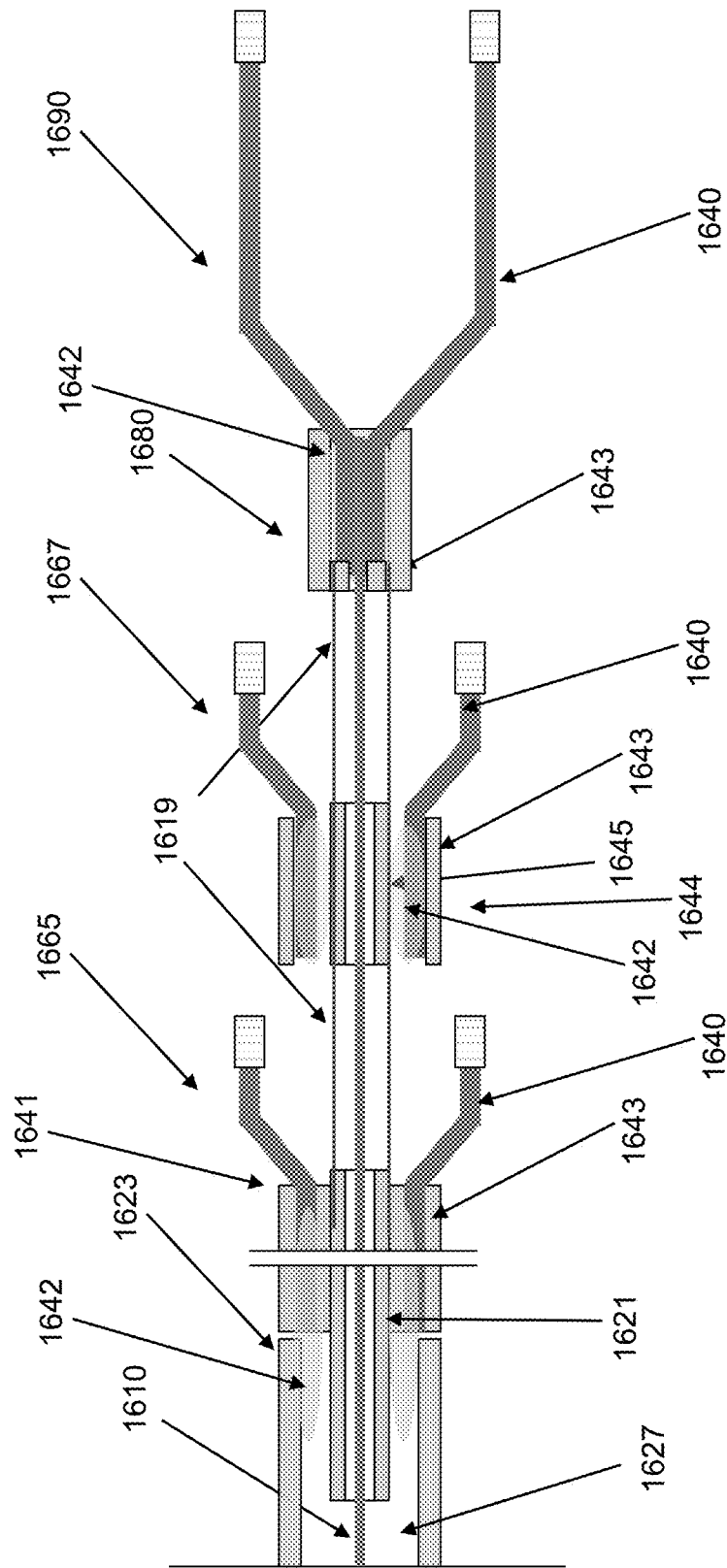
FIGS. 16A-16G show example devices having a plurality of clot engaging elements configured to collapse sequentially.

FIG. 16A illustrates an example device including a plurality of engaging elements that are configured to collapse toward one another sequentially. In some embodiments, the engaging elements can collapse toward one another simultaneously. The devices in FIGS. 16A-16E can have any of features of the devices described above. Unless specified otherwise, the devices in FIGS. 16B-16E can have any of the features of the device of FIG. 16A, for example only differing in the engaging element connection structure. In some embodiments, the device can include three or more engaging elements, such as a distal engaging element (1690), a proximal engaging element (1665), and an intermediate or "middle" engaging element (1667) between the distal engaging element (1690) and the proximal engaging element (1665). In some embodiments, the device can include more than three engaging elements, such as by having two or more middle engaging elements. In some embodiments, the device can include a central wire (1610), a tubing compartment (1627) defined by an outer pusher tubing (1623), and a connection wire (1619). The central wire (1610) can freely slide inside the tubing compartment (1627) relative to the outer pusher tubing 1623. In some embodiments, the devices can include an operable link to a handle (such as the handle (110) in FIGS. 1A-1B) at the proximal end of the device. The handle can control (e.g., push or pull) the central wire (1610).

In some embodiments, one or more engaging elements (1665, 1667, 1690) can be associated with (or connected to) the central wire (1610). As shown in FIG. 16A, the distal engaging element (1690) can be fixedly coupled to the central wire (1610), and the middle engaging element (1667) and the proximal engaging element (1665) can freely slide relative to the central wire (1610). One or more engaging elements (1665, 1667, 1690) can also be connected with the connection wire (1619). For example, as shown in FIG. 16A, the connection wire (1619) can link proximal ends of all the engaging elements (1665, 1667, 1690) at a predetermined distance in a first state. In some embodiments, the engaging elements (1665, 1667, 1690) can be pre-set with equal space there between in the first state. In some embodiments, the engaging elements (1665, 1667, 1690) can be pre-set with different distances there between in the first state. In some embodiments, such as shown in FIG. 16A, the device can include two connection wires 1619 located generally diametrically opposite each other.

The proximal engaging element (1665) can be fixed to a distal end of the outer pusher tubing (1623) by a proximal engaging element connector (1641). The proximal engaging element connector (1641) can include an outer connector tubing (1643) and/or an inner pusher tubing (1621). The connection wire (1619) and legs (1640) of the proximal engaging element (1665) can be fixed (such as being bonded) in between an inner wall of the outer connector tubing (1643) and an outer wall of the inner pusher tubing (1621), for example, with joining media, such as an adhesive, solder (1642), friction, welding, and/or the like.

The middle engaging element (1667) can be coupled to (such as being fixed or bonded) to the connection wire (1619) by a middle engaging element connector (1644). The middle engaging element connector (1644) can include an outer connector tubing (1643) and/or an inner connector tubing (1645). The connection wire (1619) and legs (1640) of the proximal engaging element (1667) can be fixed (such as being bonded) in between an inner wall of the outer connector tubing (1643) and an outer wall of the inner connector tubing (1645), such as with joining media, such as an adhesive, solder (1642), friction, welding, and/or the like. The central wire (1610) passes the hollow space of the inner connectors (1621, 1645). Accordingly, the proximal engaging element (1665) and the middle engaging element (1667) can move with the connection wire (1619), but can freely slide relative to the central wire (1610).

A proximal end of the distal engaging element (1690) can be fixed to a distal end (or tip) of the central wire (1610) via a distal engaging element connector (1680). The distal engaging element connector (1680) can join (such as secure, bond, and/or the like) the distal end of the central wire (1610), a distal tip of the connection wire (1619), and the legs (1640) of the distal engaging element (1690) with an outer connector tubing (1643), for example via joining media, such as an adhesive, solder (1642) filled within the outer connector tubing (1643), welding, friction, and/or the like.

The distal engaging element (1690) can function as a capturing element and the engaging elements (1665, 1667) proximal to the distal engaging element (1690) can function as capturing elements and/or receiving elements. The individual engaging elements may vary from about 3 mm to about 25 mm in length when in an extended configuration. FIG. 16A illustrates the device in its open state with the spaces between each adjacent engaging element (1665, 1667, 1690) being fully open and the connection wire (1619) in tension or substantially in tension. The connection wire (1619) can be flexible. The device can have a closed state, similar to the device shown in FIG. 16G, in which the spaces between each engaging elements (1665, 1667, 1690) are shortened for the purpose of holding, cinching and/or grabbing the occlusion or clot, with the connection wire (1619) buckled or folded.

The distance between the elements (1665, 1667, 1690) can be lengthened or maintained by a user pushing the central wire (1610) and stabilizing the outer pusher tubing (1623). Once the device has been advanced to a desired location, such as when the clot is between the proximal (1665) and distal (1690) engaging elements (e.g., the proximal end of the distal engaging element (1690) or the distal end of the distal engaging element (1690)), the spaces between the engaging elements (1665, 1667, 1690) can be reduced by the user pulling the central wire (1610) proximally and/or pushing the outer pusher tubing (1623) distally. The maneuver(s) can collapse the connection wire (1619), thereby bringing the engaging elements (1665, 1667, 1690) closer together to capture the clot there between. The connection wire (1619) can comprise one or more thin wires configured to be compressed axially by pulling on the central wire (1610) and/or pushing (or stabilizing) the outer pusher tubing (1623). The connection wire (1619) can include metal wires (Nitinol, stainless steels, and/or the like), plastic wires, and the like. The thin connection wires(s) can have an outer diameter range approximately from about 0.005 inch (approx. 0.13 mm) to about 0.02 inch (approx. 0.51 mm), such as about 0.005 inch (approx. 0.13 mm), about 0.006 inch (approx. 0.15 mm), about 0.007 inch (approx. 0.18 mm), about 0.008 inch (approx. 0.20 mm), about 0.009 inch (approx. 0.23 mm), about 0.01 inch (approx. 0.25 mm), about 0.012 inch (approx. 0.30 mm), about 0.014 inch (approx. 0.36 mm), about 0.016 inch (approx. 0.41 mm), about 0.018 inch (approx. 0.46 mm), or about 0.02 inch (approx. 0.51 mm). In some embodiments, the outer diameter of the connection wire(s) can vary along its length gradually or stepwise.

If the connection wire (1619) has a uniform stiffness along a length of the wire (1619), when the device is actuated to collapse the connection wire (1619), all the engaging elements (1665, 1667, 1690) may be brought closer together simultaneously or substantially simultaneously. The simultaneous collapsing of the connection wire (1619) between the proximal engaging element (1665) and the middle engaging element (1667) and between the middle engaging element (1667) and the distal engaging element (1690) may result in losing the clot. For example, if the clot has not been engaged first between the middle engaging element (1667) and the distal engaging element (1690), the clot may not be mobilized back in the blood vessel and the engaging elements (1665, 1667, 1690) may slide through the clot as the distal and middle engaging elements (1667, 1690) are pulled proximally and simultaneously toward the proximal engaging element (1665).

In some embodiments, the stiffness or axial compression force of the connection wire (1619) can be different along its length so that the clot engaging elements (1665, 1667, 1690) are brought closer together sequentially. For example, the differential axial compression force can allow a user to first bring together the distal engaging element (1690) and the middle engaging element (1667) before subsequently bringing together the middle engaging element (1667) and the proximal engaging element (1665).

In FIG. 16A, the stiffness of the connection wire (1619) from the proximal engaging element (1665) to the middle engaging element (1667) can be higher than the stiffness of the connection wire (1619) from the middle engaging element (1667) to the distal engaging element (1690). The difference in stiffness can be due to, for example, a thickness, a material of the connection wire (1690) in those different segments, shape setting if applicable, and/or the like. As shown in FIGS. 16F (device in a second state) and 16G (device in a third state), when a user pulls the connection wire (1610) proximally and/or pushes the outer pusher tubing (1623) distally, the gap between the middle and distal engaging elements (1667, 1690) can be closed in the second state before the gap between the middle and proximal engaging elements (1665, 1667) closes in the third state. This sequential collapsing of the connection wire (1619) can allow better capture of the clot during the retrieval procedure. The clot can be engaged between the middle and distal engaging elements (1667, 1690) first and then pulled back to be further engaged between the middle and proximal engaging elements (1665, 1667) subsequently.

In some embodiments, the connection wire (1619) can be stiffer between the middle and distal engaging elements (1667, 1690) than between the middle and proximal engaging elements (1665, 1667) so that the middle and proximal engaging elements (1665, 1667) are brought closer together first before the distal and middle engaging elements (1667, 1690) are brought closer together.

The device can be deployed to remove an occlusion or clot in a body lumen using methods such as shown in FIGS. 2A-C. To engage or hold the clot, an operator may shorten the space or gap between the engaging elements (1665, 1667, 1690) (i) by pulling the central wire (1610) backward (proximally) while holding the tubing compartment (1627) stable, (ii) by pushing the tubing compartment (1627) forward (distally) while holding the central wire (1610) stable, or (iii) by pulling the central wire (1610) backward (proximally) while pushing the tubing compartment (1627) forward (distally). This adjustment of the position of the engaging elements (1665, 1667, 1690) and the space there between can allow at least part of the clot to be compressed/cinched or caught in the space gap, such as shown in FIGS. 2B-2C. Alternatively or in combination, the occlusion can be immobilized via the frictional engagement with the body lumen and one or more engaging element(s) (1665, 1667, 1690). The occlusion can also be directly engaged with the wires or struts of the engaging elements (1665, 1667, 1690). In some embodiments, the engagement (capture) and containment of the occlusion may involve more than one mode disclosed herein. The modes of securely cinching/grabbing the occlusion may include one or more of the following: (1) the occlusion may be cinched or held between the engaging elements, (2) the occlusion may be directly engaged with the wires or struts of one or more engaging elements, (3) the occlusion may be frictionally contained between the body lumen and one or more of the engaging elements, and/or (4) the occlusion may be frictionally contained between the body lumen and the space(s) between the engaging elements.

In some embodiments, during the treatment procedure, the distal engaging element (1690) can be moved backward first and can cinch or hold the clot with the adjacent engaging element(s), such as the middle engaging element (1667). The adjacent engaging elements, such as one or more middle engaging elements can then pushed backward (proximally) toward the proximal engaging element (1690), simultaneously or sequentially, which can in turn further compress and/or cinch the occlusion. The user can shorten the distance between the engaging elements until the occlusion is securely cinched/grabbed by the device. Once the occlusion is believed to be securely grabbed or cinched by the device, the device can then be pulled proximally out of the body lumen.

Other types of linking or connecting structures can be used to connect the engaging elements (1665, 1667, 1690). In some embodiments, the linking structure can have different axial compression load along its length so that the engaging elements are brought closer to one another sequentially when pulling the central wire (1610) and/or pushing the outer pusher tubing (1623).

Figure 16B:
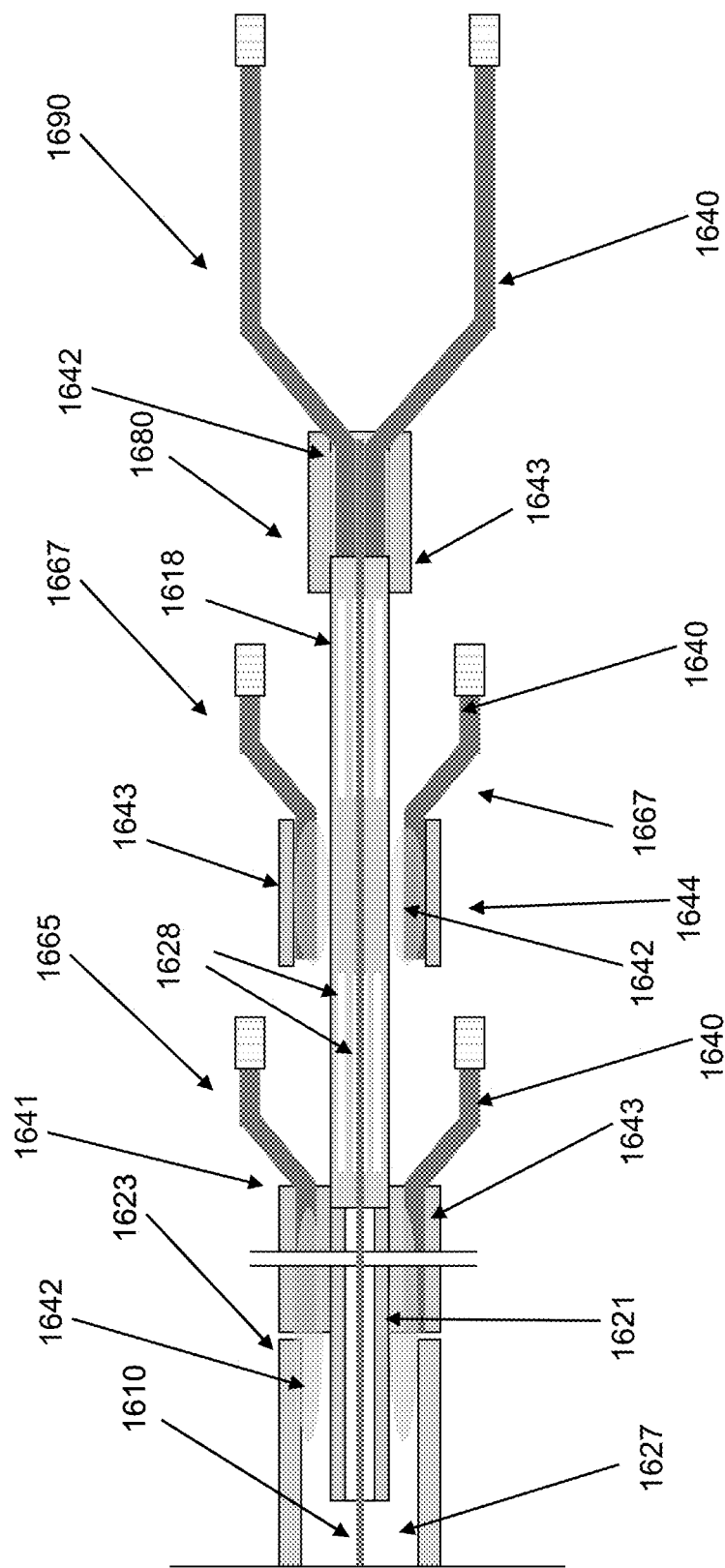
Figure 16C:
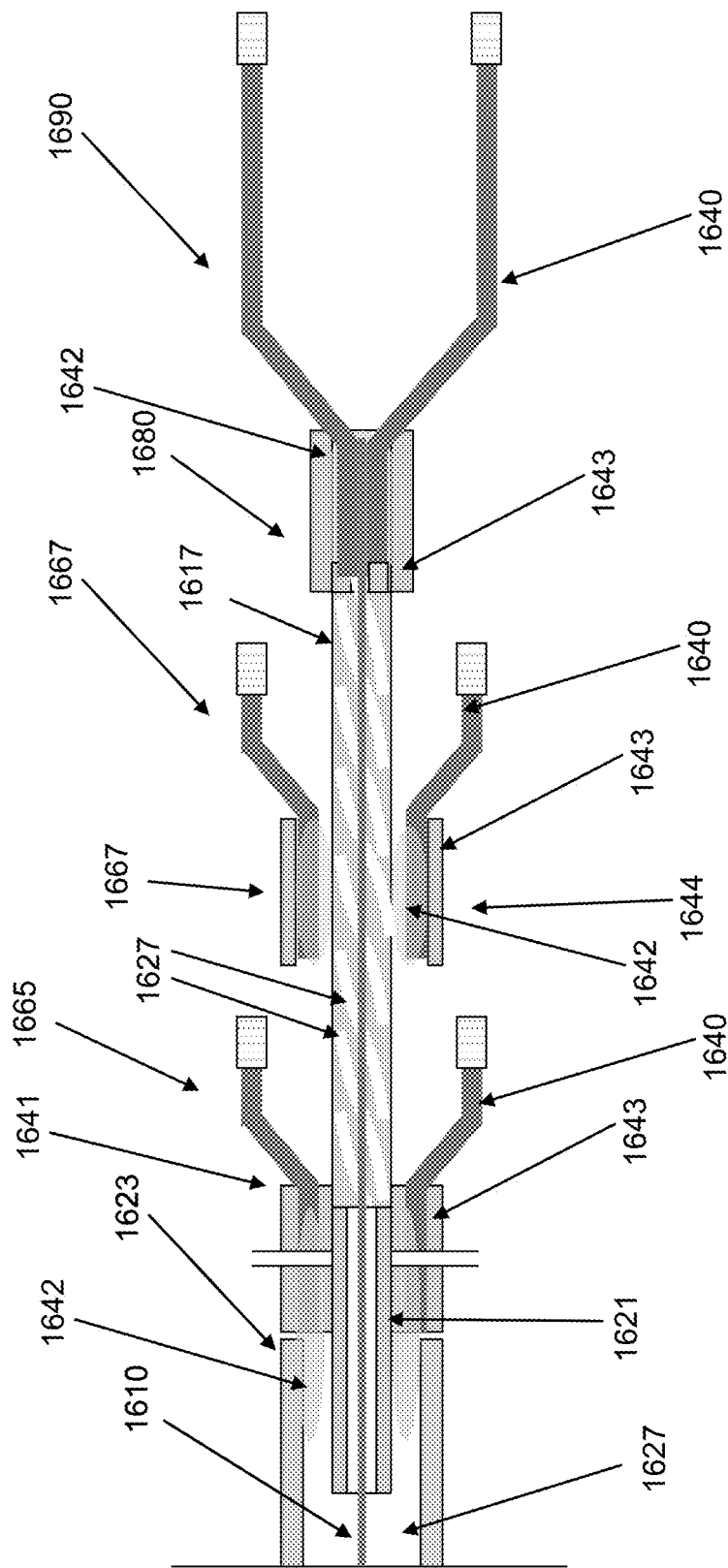
Figure 16D:
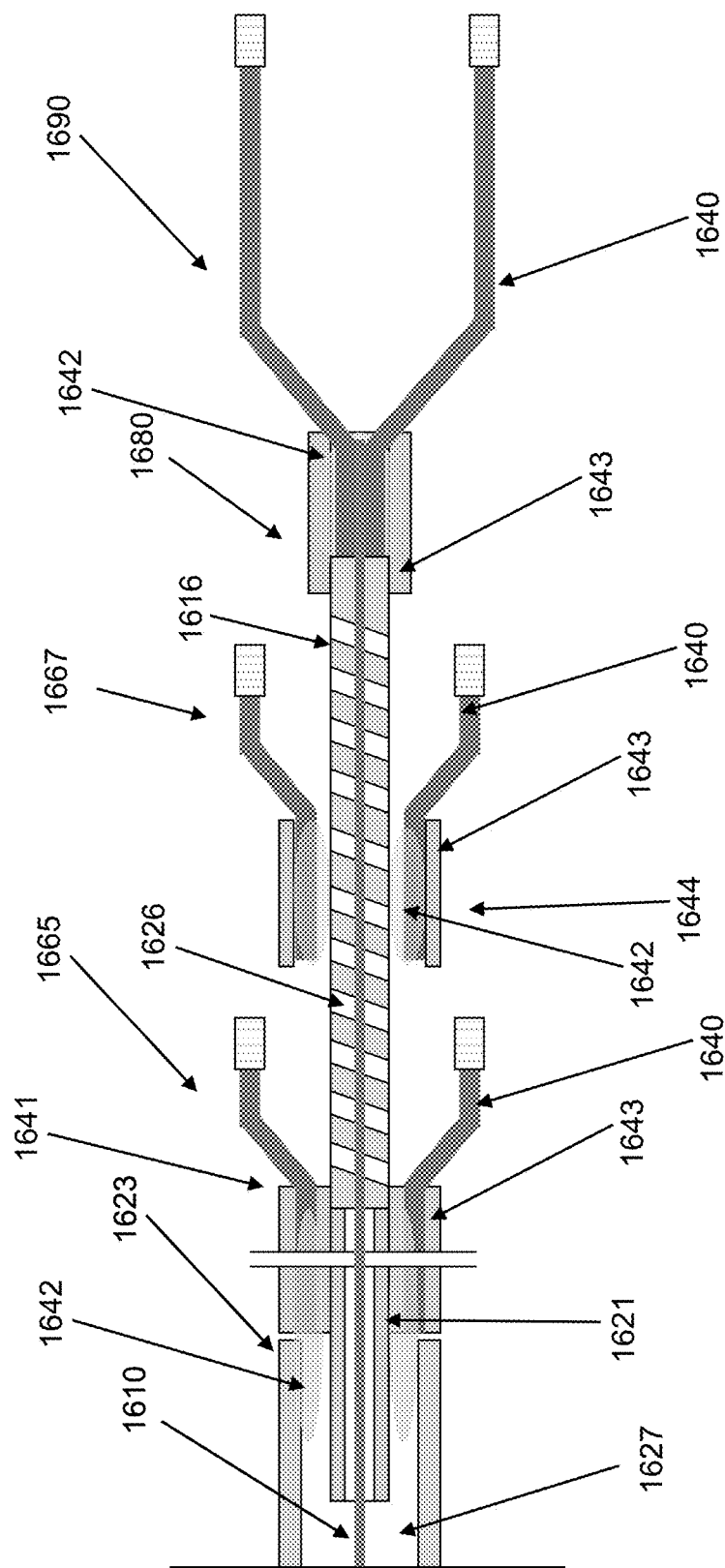

As shown in FIGS. 16B-16D, the linking structure can comprise or be made of a tubing which has slits along its length. Devices incorporating a tubing as the linking structure, which can have a greater rigidity than devices incorporating flexible wires as the linking structure, may advantageously omit an inner connector tube at the middle engaging element, thereby reducing the number of components for assembling the device. The tubing can comprise or be made of metal (such as Nitinol, stainless steels, and/or the like), plastic, and the like. The tubing can start as a sheet that is rolled into a tube (e.g., after cutting the slits). In some embodiments, the slits can be cut using laser. The patterns of the slits can vary, such as being vertical, horizontal, slanted, spiral, a combination thereof, and/or the like. In FIG. 16B, the tubing (1618) comprises slits (1628) oriented in directions substantially parallel to a longitudinal axis of the tubing (1628) and/or to the connection wire (1610). In FIG. 16C, the tubing (1617) comprises slits (1627) oriented at an angle relative to the longitudinal axis of the tubing (1628) and/or to the connection wire (1610). The angle can be, for example, between about 5° and about 85° relative to the longitudinal axis (e.g., about 5°, about 10°, about 15°, about 20°, about 25°, about 30°, about 35°, about 40°, about 45°, about 50°, about 55°, about 60°, about 65°, about 70°, about 75°, about 80°, about 85°, and ranges between such values). In FIG. 16D, the tubing (1616) can have spiral or helical slits 1626 along the longitudinal axis of the tubing (1628) and/or to the connection wire (1610). The angle of the spiral or helix slit can be, for example, between about 5° and about 85° relative to the longitudinal axis (e.g., about 5°, about 10°, about 15°, about 20°, about 25°, about 30°, about 35°, about 40°, about 45°, about 50°, about 55°, about 60°, about 65°, about 70°, about 75°, about 80°, about 85°, and ranges between such values).

The distance between the engaging elements (1665, 1667, 1690) can be shortened by pulling the central wire (1610) and/or stabilizing (or pushing) the outer pusher tubing (1623). The tubing (1618, 1617, 1616) can undergo an axial loading along its length when the user pulls the central wire (1610) and/or holds the outer pusher tubing (1623) steady and/or pushes the outer pusher tubing (1623). The compression can cause the tubing (1618, 1617, 1616) to deform at or near the slits (1628, 1627, 1626). In some embodiments, the tubing (1618, 1617, 1616) can foreshorten under the axial compressive load. The foreshortening can allow the position of the middle and/or distal engaging elements (1667, 1690) to change relative to the proximal engaging element (1665), with the distance between the elements (1665, 1667, 1690) being shortened. In some variants, the tubing (1618, 1617, 1616) can have a corrugated shape which can also foreshorten with axial loading. In addition to the capturing action of the engaging elements (1665, 1667, 1690), the radial expansion of the foreshortened tubing (1618, 1617, 1616) can help entrain and/or hold the clot against the blood vessel wall, and/or hold the clot more forcibly during withdrawal of the device, which can improve capture and/or removal of the clot.

The slits (1628, 1627, 1626) can vary between the proximal and middle engaging elements (1665, 1667) and between the middle and distal engaging elements (1667, 1690). The slits (1628, 1627, 1626) can vary in the cut pattern, pitch/angle, density, thickness, material, shape set if applicable, and/or the like. In some embodiments, the section of the tubing (1618, 1617, 1616) between the middle and distal engaging elements (1667, 1690) can withstand a lower compressive load before collapsing (such as foreshortening) than the section of the tubing (1618, 1617, 1616) between the middle and proximal engaging elements (1666, 1667). The gap between the middle and distal engaging elements (1667, 1690) can be reduced before the reduction of the gap between the middle and proximal engaging elements (1665, 1667) when pulling the central wire (1610) and/or pushing the outer pusher tubing (1623). In some embodiments, the section of the tubing (1618, 1617, 1616) between the middle and proximal engaging elements (1665, 1667) can withstand a lower axial compressive loading before collapsing (such as foreshortening) than the section of the tubing (1618, 1617, 1616) between the middle and distal engaging elements (1667, 1690). In some embodiments, the tubing (1618, 1617, 1616) allows simultaneous collapsing.

Figure 16E:
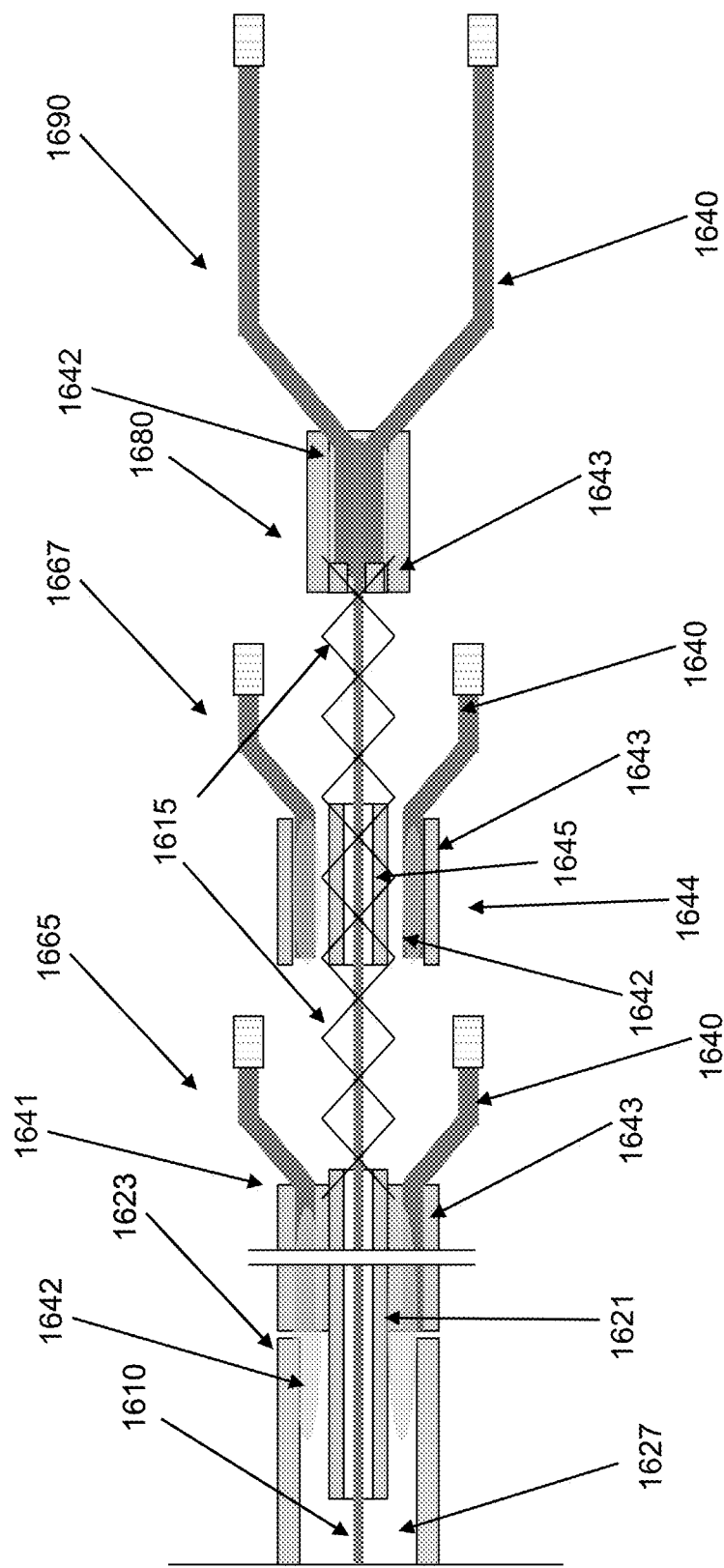
Figure 16F:
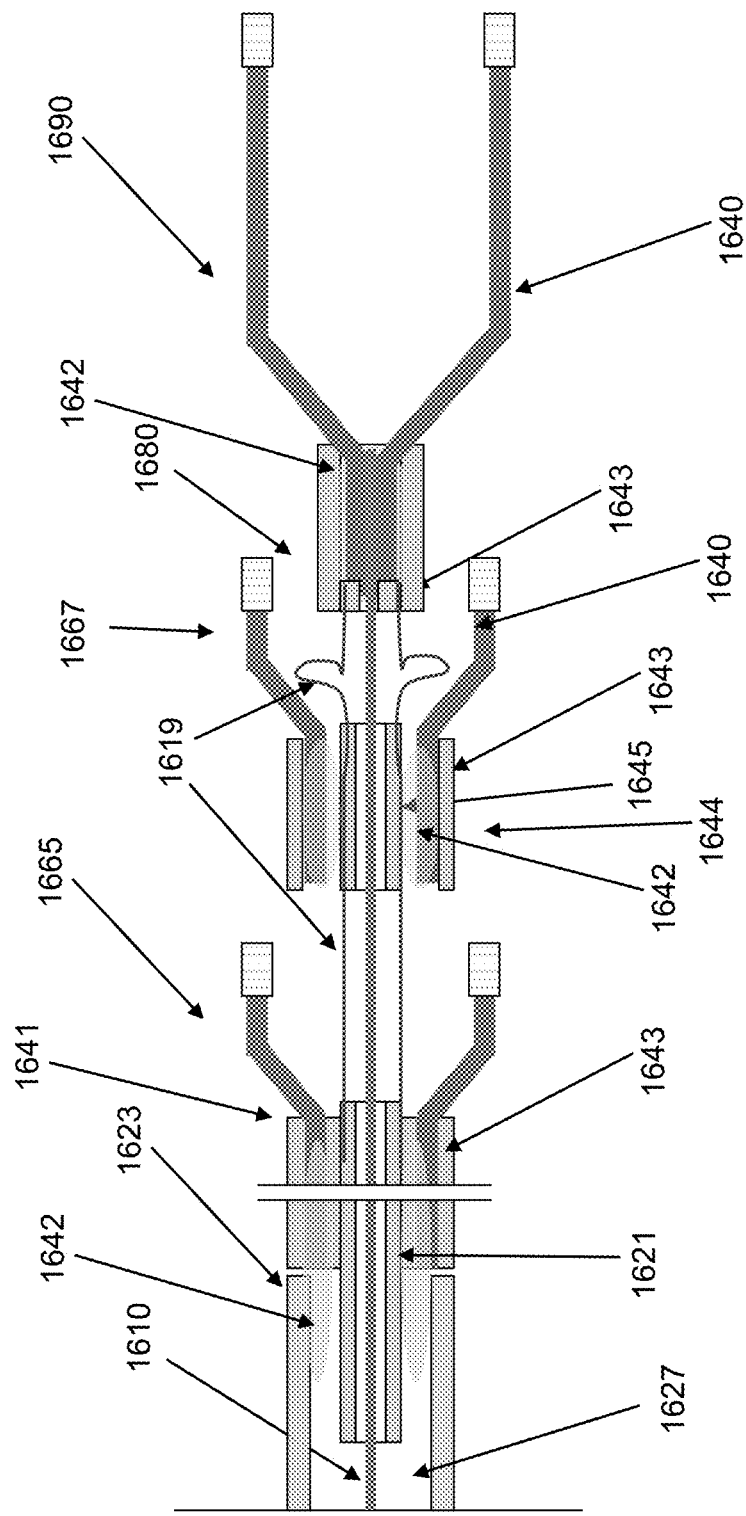
Figure 16G:
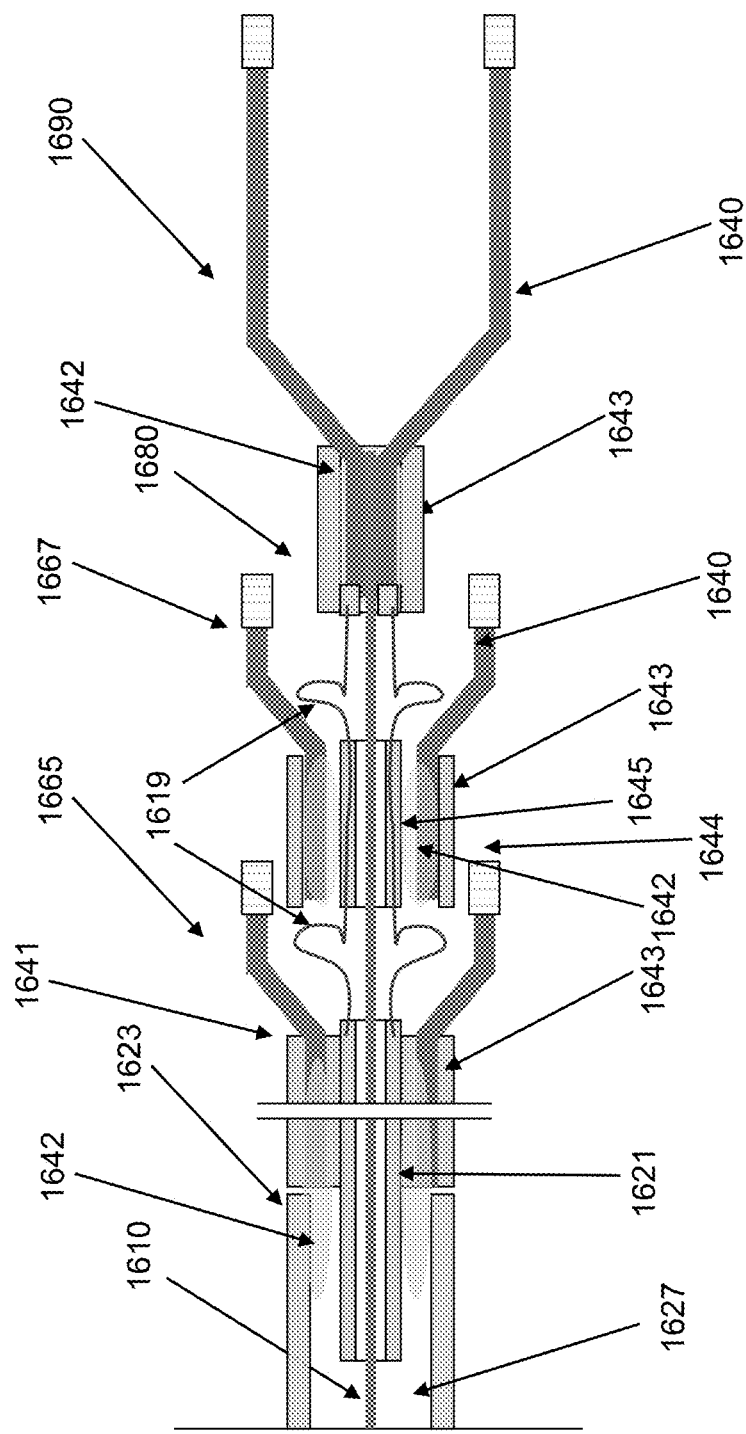

As shown in FIG. 16E, the linking structure can include a linking braid or tubular structure (1615). The braid (1615) can comprise or be made of metal (such as NiTi, stainless steels, and/or the like), plastic, and the like. In some embodiments, the braid (1615) comprises a plurality of wires or filaments woven into a tubular braid. In some embodiments, the tubular structure (1615) can be laser-cut from a hypotube or other types of tubing. The strut thickness, wire thickness, weave pattern, braid angle, density, shape set if applicable, and/or other properties of the braid or tubular structure (1615) can optionally vary so that the section of the tubing (1618, 1617, 1616) between the middle and distal engaging elements (1667, 1690) can withstand a lower axial compressive loading before collapsing (such as foreshortening) than the section of the tubing (1618, 1617, 1616) between the middle and proximal engaging elements (1665, 1667), or that the section of the tubing (1618, 1617, 1616) between the middle and proximal engaging elements (1665, 1667) can withstand a lower axial compressive loading before collapsing (such as foreshortening) than the section of the tubing (1618, 1617, 1616) between the middle and distal engaging elements (1667, 1690). In some embodiments, the braid 1615 allows simultaneous collapsing.

In some embodiments, the linking structure can comprise different linking structures. For example, the section between the middle and proximal engaging elements (1667, 1665) can comprise a wire, tubing including longitudinal slits, tubing including angled slits, tubing including helical slits, or a braid, and the section between the middle and distal engaging elements (1667, 1690) can comprise a different one of a wire, tubing including longitudinal slits, tubing including angled slits, tubing including helical slits, or a braid. The inherent characteristic of compression upon application of an axial load between the different types of linking structures may provide sequential compression without variation of one type of linking structure.

In some embodiments in which the device comprises more than three engaging elements, the stiffness of the linking structure can vary between each of the engaging elements. For example, a stiffness between a proximal engaging element and a second most proximal engaging element can be different than a stiffness between the second most proximal engaging element and a third most proximal engaging element, which can be different than a stiffness between the third most proximal engaging element and a distal engaging element. In some embodiments, the stiffness can continue in the same direction (e.g., stiffer, stiffer, stiffer or less stiff, less stiff, less stiff). In some embodiments, a change in stiffness can alternate (e.g., stiffer, less stiff, stiffer or less stiff, stiffer, less stiff). The principles disclosed herein can also be applicable to five or more engaging elements.

The principles herein can be applicable to two engaging elements. For example, an initial axial load between a proximal engaging element and a distal engaging element can cause a linking structure to collapse a first amount and a further axial load between the proximal engaging element and the distal engaging element can cause the linking structure to collapse a second amount different than the first amount. The linking structure may foreshorten, which can help entrain and/or hold the clot against the blood vessel wall, and/or hold the clot more forcibly during withdrawal of the device, which can improve capture and/or removal of the clot.

The linking structures disclosed herein can resist different axial loading along the length of the linking structures. For example, one section of the linking structures can resistant an axial loading of about 5 gram, or about 10 grams, or about 15 grams, or about 20 grams, or about 25 grams, or about 30 grams, or about 35 grams, or about 40 grams, or about 45 grams, or about 50 grams, or any ranges between such values.

FIGS. 17A-17F illustrate embodiments of a device comprising two engaging elements: a distal engaging element (1790) and a proximal engaging element (1765). The device can include features described, for example, in U.S. patent application Ser. No. 13/191,306 and U.S. patent application Ser. No. 13/543,657, which are incorporated herein by reference in their entirety for all purposes. In some embodiments, the device can include only one engaging element or multiple engaging elements (e.g., as described herein and/or in U.S. patent application Ser. No. 14/638,994, which is incorporated herein by reference in its entirety for all purposes). The legs (1740) of the proximal and/or distal engaging elements (1765, 1790) can include markers (1770), such as at a distal end of the leg 1740. Markers can also be located at other parts of the device. In some embodiments, the device can include a central wire (1710) and a microcatheter (1730). The device can optionally include a linking wire (1719) when the device includes more than one engaging element. The central wire (1710) can have a taper so that a distal portion of the central wire (1710) can have a smaller outer diameter than a remainder of the central wire (1710). The devices in FIGS. 17A-17F can advantageously omit or be devoid of or not have an outer pusher tubing. The lack of outer pusher tubing can allow the distal end of the device (including the proximal engaging element (1765) and the distal engaging element (1790)) to reach more distal portions of the blood vessel lumen, such as small branch arteries, that may be too small to be accessible by a device incorporating an outer pusher tubing.

Figure 17A:
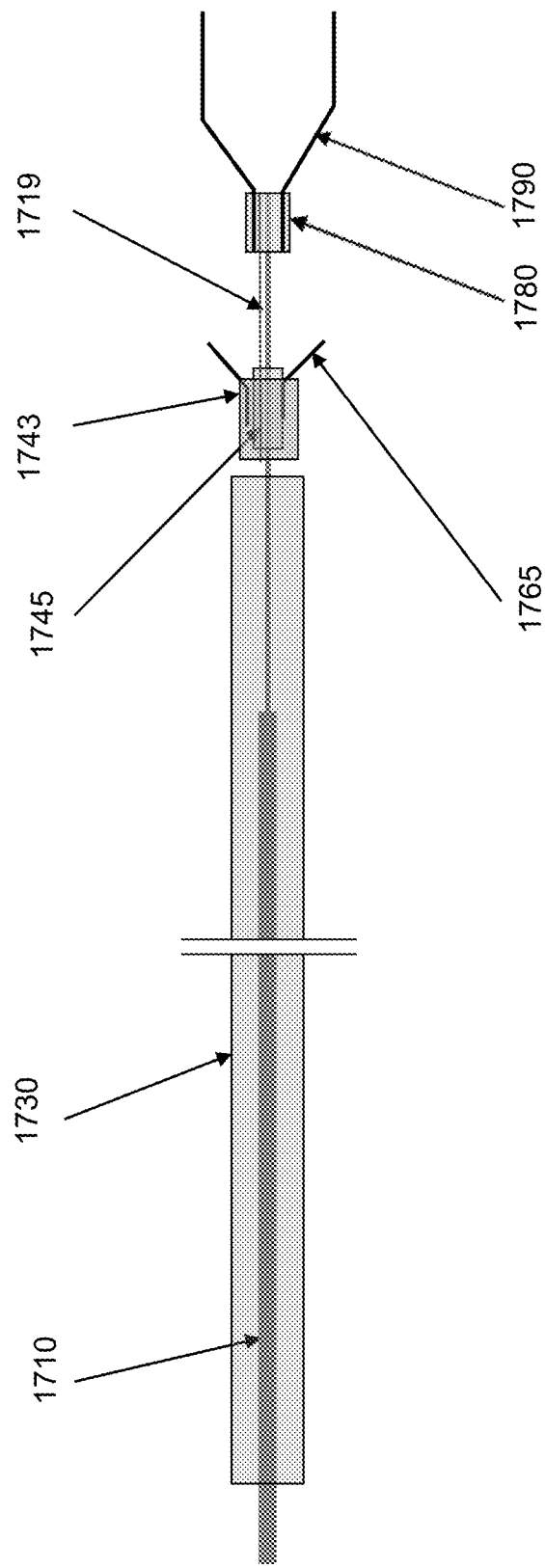
FIGS. 17A-17D show example two-part devices having a proximal engaging element and a distal engaging element.

The central wire (1710) can freely slide inside the microcatheter (1730). In some embodiments, the device can further include an operably link to a handle (such as the handle (110) in FIGS. 1A-1B) at the proximal end of the device. The handle can control (e.g., push or pull) the central wire (1710). As shown in FIG. 17A, the distal engaging element (1790) can be fixed to the distal tip of the central wire (1710). The proximal engaging element (1765) can be set a predetermined distance from the distal engaging element (1790). The two engaging elements can be linked with a linking wire or structure (1719) (such as the wire in FIGS. 17A-17C, suture, braid (1715) in FIG. 17D, tubings with slits such as disclosed herein, and/or the like).

Figure 17B:
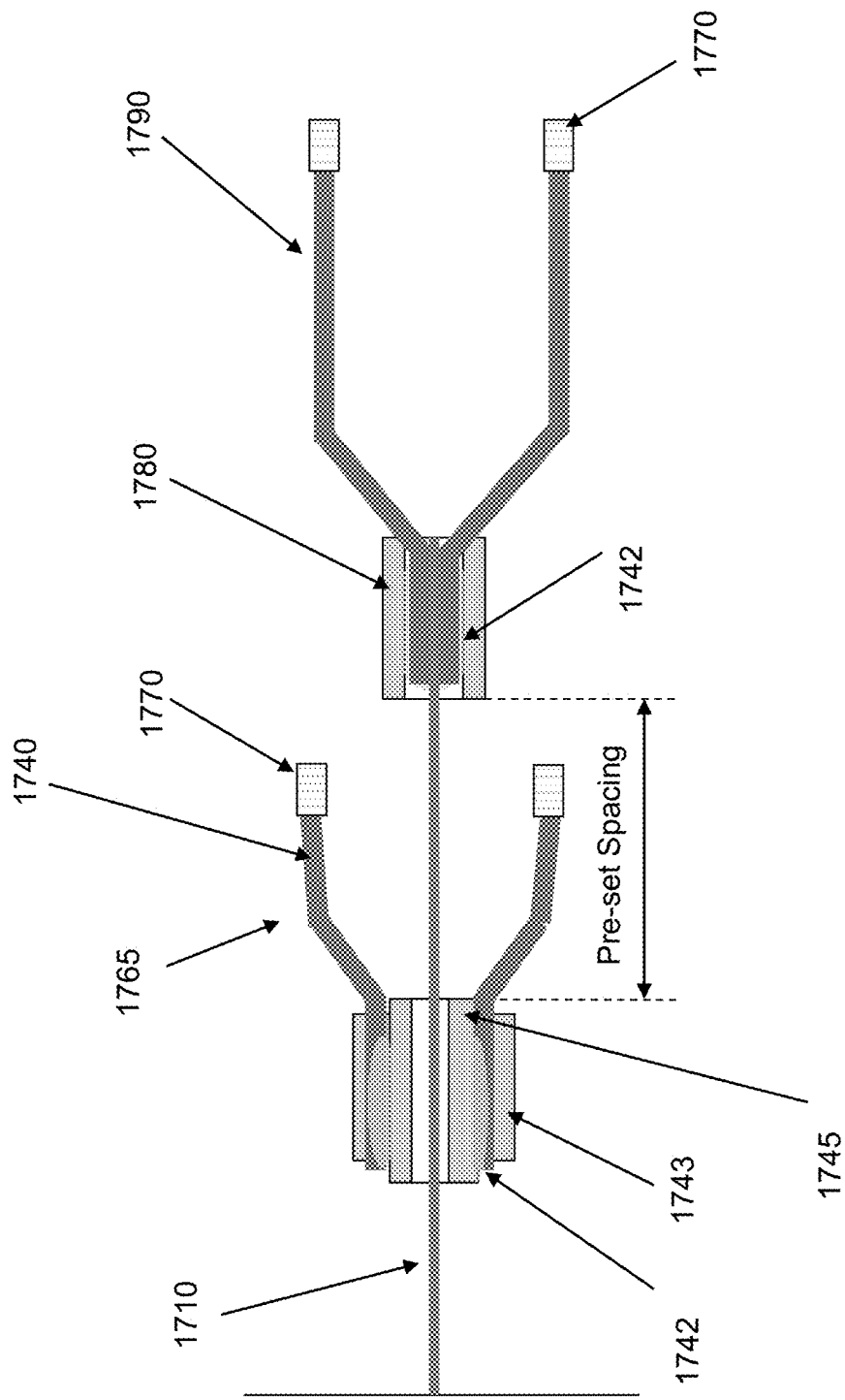

As shown in FIG. 17B, the proximal engaging element (1765) can be fixed to a proximal engaging element connector (1741). The proximal engaging element connector (1741) can include an outer connector tubing (1743) and/or an inner connector tubing (1745). The linking wire (1719) and legs (1740) of the proximal engaging element (1765) can be fixed (such as being bonded) in between an inner wall of the outer connector tubing (1743) and an outer wall of the inner connector tubing (1745), for example, with joining media, such as an adhesive, solder (1642), friction, welding, and/or the like. The proximal engaging element (1765) can freely slide over the central wire (1710). As shown in FIG. 17B, a proximal end of the distal engaging element (1790) can be fixed to a distal end (or tip) of the central wire (1710) via a distal engaging element connector (1780). The distal engaging element connector (1780) can join (such as by securing, bonding, and/or the like) the distal tip of the central wire (1710), the linking wire (1719), and the legs (1740) of the distal engaging element (1790) with an outer connector tubing (1743), such as using joining media, such as an adhesive, solder (1642), friction, welding, and/or the like.

To introduce the device into a body lumen inside the microcatheter (1730), the distal engaging element (1790) can be pushed distally along the microcatheter (1730). The linking wire (1719) can be under tension, which can pull the proximal engaging element (1765) through the microcatheter (1730). During a clot retrieval procedure, the proximal engaging element (1765) can be placed at a proximal end of the clot and the distal engaging element (1790) can be distal to the proximal end of the clot or distal to the clot (when device is still inside the distal end of the microcatheter (1730)). When the microcatheter (1730) is unsheathed while holding the central wire (1710), the proximal and distal engaging elements (1765, 1790) can expand or open. The clot can be at least partially between the proximal and distal engaging elements (1765, 1790). The unsheathing can stop when a proximal end of the proximal engaging element (1765) is just out of the distal end of the microcatheter (1730).

Figure 17C:
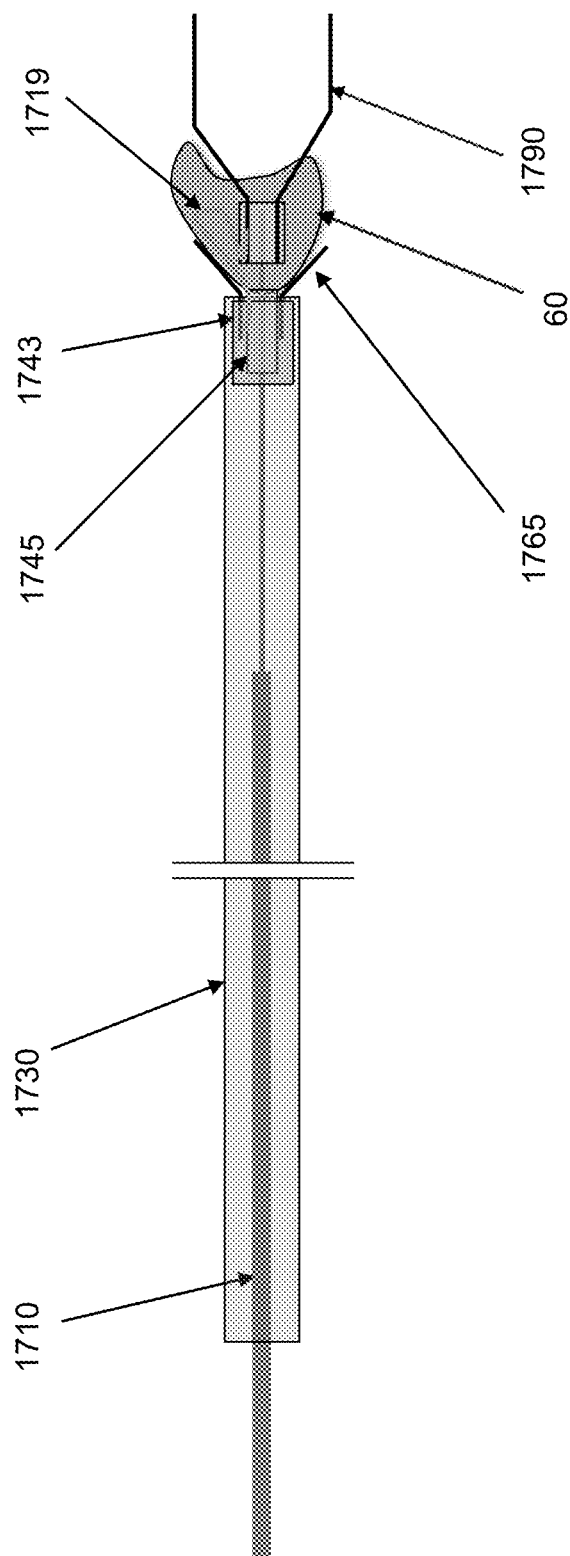
Figure 17D:
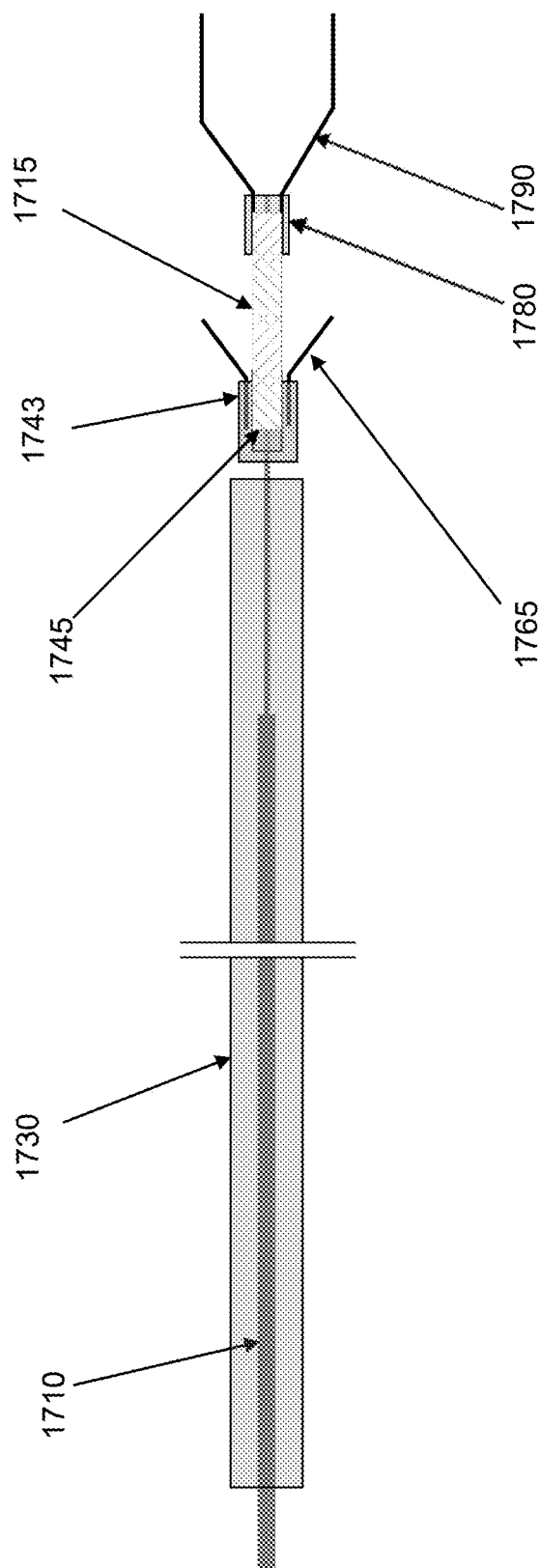

The spaces between the engaging elements can be reduced by a user pulling the central wire (1710) proximally, thereby bringing the engaging elements closer together to capture a clot there between, such as shown in FIG. 17C. The clot can be engaged by the distal engaging element (1790), dragged backward, and grabbed between the proximal and distal engaging elements (1765, 1790). The individual engaging element may vary from about 3 mm to about 25 mm in length when in an extended configuration. When the distal engaging element (1790) is pulled backward, the flexible linking wire (1719) can buckle. In a device that has only one engaging element, the clot can be engaged by the engaging element and removed proximally with the device. Alternatively or additionally, the space between the engaging elements (1765, 1790) can be reduced by pushing the microcatheter forward (1730). This can push the proximal engaging element (1765) toward the distal engaging element (1790). Pushing the microcatheter (1730) forward may be done while stabilizing or fixing the central wire (1710). The space between the engaging elements (1765, 1790) can also be reduced by pulling on the central wire (1710) while pushing on the microcatheter (1730) at the same time.

In some embodiments, the strut or feet design of the proximal engaging element (1765) can be configured to make it difficult to pull the proximal engaging element (1765) back into the microcatheter (1730). For example, the strut or feet of the proximal engaging element (1765) can be rigid and/or thick enough, and/or angulated enough (such as being between about 30° and about 90° (e.g., about 30°, about 35°, about 40°, about 45°, about 50°, about 55°, about 60°, about 65°, about 70°, about 75°, about 80°, about 85°, about 90°, and ranges between such values)) so that, when expanded, the struts can resist collapsing and being pulled back into the microcatheter (1730). In some embodiments, thicker struts of the proximal engaging element (1765) can allow lower angles. A proximal engaging element (1765) including a lower angle may be easier to push through the microcatheter (1730). In some embodiments, higher angles of the proximal engaging element (1765) can allow thinner struts. The angles disclosed herein can be with respect to a longitudinal axis of the central wire (1710), a longitudinal axis of the microcatheter (1730), and/or a longitudinal axis of the proximal engaging element (1765). The distal tip of the microcatheter (1730) can stop the expanded proximal engaging element (1765) from moving backward into the microcatheter (1730) and the device becomes "locked" at the distal tip of the microcatheter (1730). The "lock" can improve and/or make more secure the engagement of the clot between the proximal and distal engaging elements (1765, 1790). With the relative positions of the microcatheter tip and the distal and proximal engaging elements (1765, 1790) locked, the device can be removed from the artery with the engaged clot.

The device can additionally or alternatively include a stopper feature at a proximal end of the proximal engaging element (1765). The stopper feature can be of any shape (e.g., loops, clips, and/or the like) and/or size and can be configured to expand radially (such as automatically expending (e.g., due to shape setting)) upon unsheathing the microcatheter (1730). The stopper feature can promote the proximal engaging element (1765) being stopped by the tip of the microcatheter (1730) while pulling the distal engaging element (1790) backward to engage a clot. A clot removal procedure in which the proximal end of the proximal engaging (1765) rests on the distal tip of the microcatheter (1730) can allow the clot can be more tightly engaged in between the proximal and distal engaging elements (1765, 1790). Inhibiting or preventing the proximal engaging element (1765) that has captured a clot from reentering the microcatheter (1730) can reduce a risk of the captured clot being dislodged entirely or in smaller portions (e.g., releasing smaller emboli). Such a procedure can reduce or eliminate an outer pusher tubing so that the device can be advanced to smaller body lumens (such as small branch arteries) to remove occlusion in those lumens than when an outer pusher tubing is required. Such potential advantages may be achieved without significantly increasing trauma to the body lumen wall.

Figure 17E:
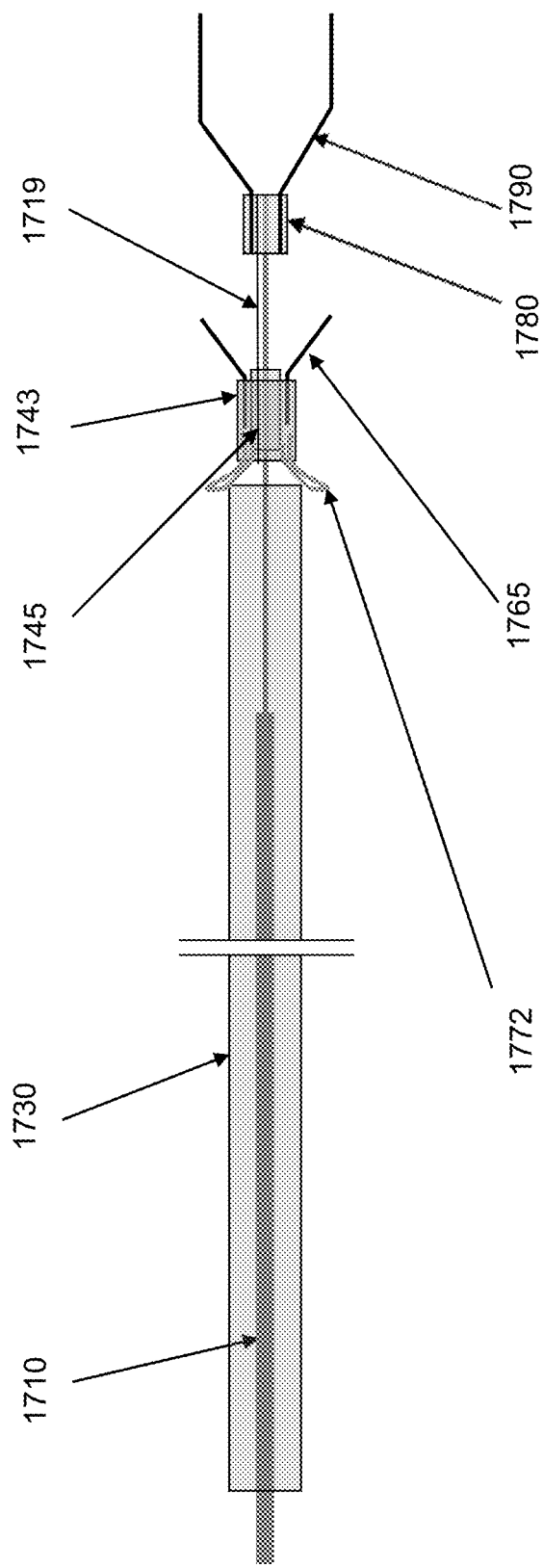
FIG. 17E shows an example device including a stopper feature.
Figure 17F:
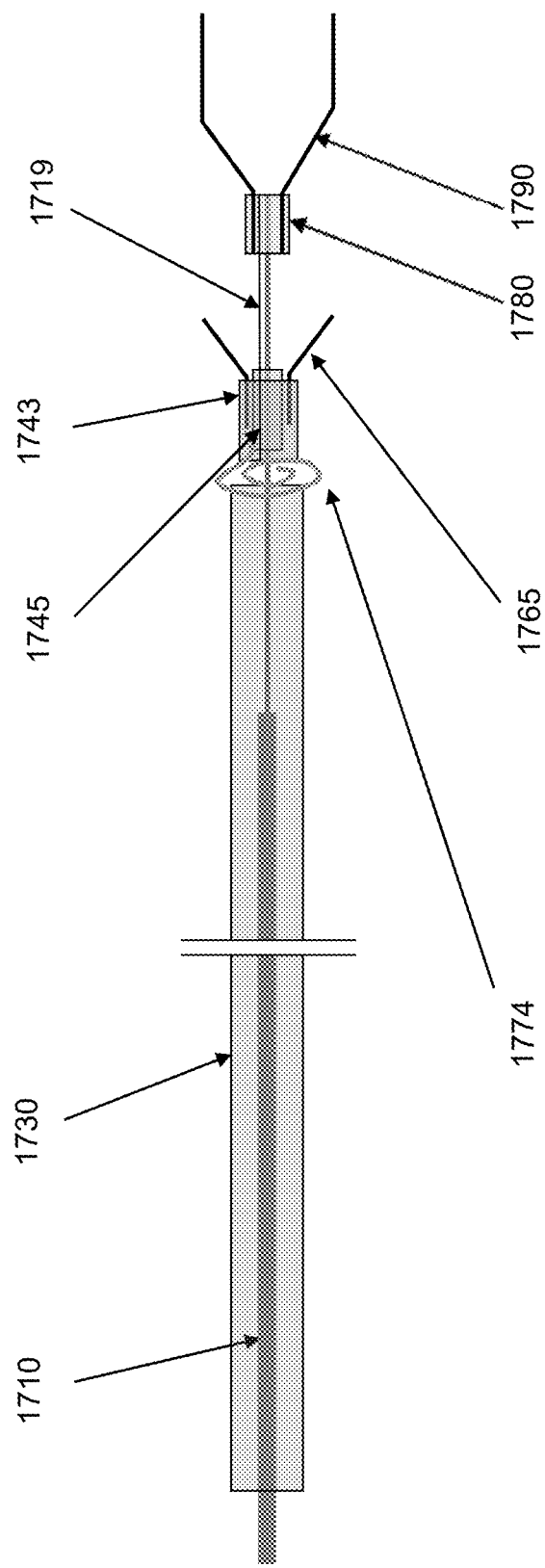
FIG. 17F shows another example device including a stopper feature.

As shown in FIG. 17E, the stopper feature can include loops (1772). The loops 1772 can bend radially outward when the proximal engaging element (1765) is outside the microcatheter (1730). In some embodiments, the loops can automatically open. The stopper feature can also be a spiral spring wire (1774), such as shown in FIG. 17F. Other examples of the stopper feature include any construct made of shape memory alloy (e.g., a Nitinol cage), a wire with a pre-set three-dimensional shape, and the like. In some embodiments, the stopper feature, when expanded, has a diameter greater than a diameter of a distal end of a microcatheter.

The strut design of the leg (1740) of the proximal engaging element (1765) and/or the other stopper features disclosed herein can resist a pull-out force of about 50 grams, about 100 grams, about 150 grams, about 200 grams, about 250 grams, about 300 grams, about 350 grams, about 400 grams, about 450 grams, or any ranges between such values.

In some embodiments in which a device has more than two engaging elements, the strut of the leg of the proximal engaging element or other stopper features at the proximal end of the proximal engaging element can be included to inhibit or prevent an expanded proximal engaging element from being pulled back into a microcatheter when the central wire is pulled to move the distal engaging element proximally and/or the microcatheter is pushed to capture a clot.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

Terminology

As used herein, the relative terms "proximal" and "distal" shall be defined from the perspective of the delivery system.

Thus, proximal refers to the direction of the handle portion of the delivery system and distal refers to the direction of the distal tip.

Although certain embodiments and examples have been described herein, it will be understood by those skilled in the art that many aspects of the delivery systems shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

Conditional language used herein, such as, among others, "can," "might," "may," "e.g.," and the like, unless specifically stated otherwise, or otherwise understood within the context as used, is generally intended to convey that some embodiments include, while other embodiments do not include, certain features, elements, and/or states. Thus, such conditional language is not generally intended to imply that features, elements, blocks, and/or states are in any way required for one or more embodiments or that one or more embodiments necessarily include logic for deciding, with or without author input or prompting, whether these features, elements and/or states are included or are to be performed in any particular embodiment.

The methods disclosed herein may include certain actions taken by a practitioner; however, the methods can also include any third-party instruction of those actions, either expressly or by implication. For example, actions such as "advancing the self-expanding stent" include "instructing advancing the self-expanding stent."

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±1%, ±5%, ±10%, ±15%, etc.). For example, "about 0.01 inches" includes "0.01 inches." Phrases preceded by a term such as "substantially" include the recited phrase and should be interpreted based on the circumstances (e.g., as much as reasonably possible under the circumstances). For example, "substantially linear" includes "linear."

What is claimed is:

1. A device for removing an obstruction from a body lumen, the device comprising:
   a central wire comprising a proximal end and a distal end;
   an engaging element at or near the distal end of the central wire; and
   a microcatheter at least partially containing the engaging element during introduction into the body lumen,
   wherein the engaging element is self-expandable upon unsheathing the microcatheter, and
   wherein the engaging element, when expanded upon unsheathing from the microcatheter, is configured to inhibit re-sheathing of the engaging element in the microcatheter upon application of at least one of a proximal force to the engaging element or a distal force to the microcatheter.

2. The device according to claim 1, wherein a proximal end of the engaging element comprises a stopper configured to expand radially upon unsheathing the engaging element from the microcatheter.

3. The device according to claim 2, wherein the stopper comprises loops configured to bend radially outward upon unsheathing the engaging element from the microcatheter.

4. The device according to claim 2, wherein the stopper comprises a spiral spring wire configured to expand radially outward upon unsheathing the engaging element from the microcatheter.

5. The device according to claim 1, the engaging element comprises legs having a thickness configured to inhibit re-sheathing of the engaging element in the microcatheter when the legs are expanded.

6. The device according to claim 1, wherein legs of the engaging element are at an angle of between 30° and 90° with respect to a longitudinal axis of the microcatheter when the legs are expanded.

7. The device according to claim 1, wherein the engaging element comprises wires or struts.

8. The device according to claim 1, wherein the engaging element is configured to inhibit re-sheathing of the microcatheter upon application of a proximal force of 50 grams to 450 grams.

9. The device according to claim 1, further comprising a second engaging element located distal to the engaging element.

10. The device according to claim 9, wherein the second engaging element is fixedly attached to the distal end of the central wire.

11. The device according to claim 10, wherein the engaging element is slidable on the central wire.

12. The device according to claim 9, comprising a linking connector coupled to the engaging element and the second engaging element, the linking connector spacing the engaging element and the second engaging element at a distance.

13. The device according to claim 12, wherein the linking connector is a wire, a hypotube with slits, or a braid.

14. The device according to claim 9, comprising a third engaging element located between the engaging element and the second engaging element.

15. The device according to claim 1, wherein the engaging element is configured to inhibit re-sheathing at least while the device is withdrawn from the body lumen.

16. The device according to claim 1, wherein the engaging element is configured to inhibit re-sheathing at least while a proximal end of the engaging element abuts a distal tip of the microcatheter.

17. A method of removing at least part of an occlusion from a body lumen, the method comprising:
   introducing into the body lumen the device according to claim 1, including the engaging element at least partially contained in the microcatheter, until the engaging element is proximate the occlusion;
   deploying the engaging element from the microcatheter so that a distal tip of the microcatheter is proximal to the engaging element;
   engaging at least part of the occlusion with the engaging element;
   abutting the distal tip of the microcatheter with the proximal end of the engaging element; and
   removing the engaged occlusion from the body lumen, wherein during the removing, the engaging element inhibits re-sheathing of the microcatheter over the engaging element.

18. The method according to claim 17, wherein the proximal end of the engaging element comprises a stopper configured to expand radially upon unsheathing the microcatheter.

19. The method according to claim 17, wherein legs of the engaging element have a thickness configured to inhibit re-sheathing of the microcatheter when the legs are expanded.

20. The method according to claim 17, wherein legs of the engaging element are at an angle of between 30° and 90° with respect to a longitudinal axis of the microcatheter when the legs are expanded.

21. The method according to claim 17, wherein abutting the distal tip of the microcatheter with the proximal end of the engaging element comprises proximally retracting the engaging element.

22. The method according to claim 17, wherein removing the engaged occlusion is with the engaging element.

23. A device for removing an obstruction from a body lumen, the device comprising:
   a central wire comprising a proximal end and a distal end;
   an engaging element at or near the distal end of the central wire, wherein the engaging element comprises wires or struts; and
   a microcatheter at least partially containing the engaging element during introduction into the body lumen,
   wherein the engaging element, when expanded upon unsheathing from the microcatheter, is configured to inhibit re-sheathing of the engaging element in the microcatheter upon application of at least one of a proximal force to the engaging element or a distal force to the microcatheter.

24. A device for removing an obstruction from a body lumen, the device comprising:
   a central wire comprising a proximal end and a distal end;
   an engaging element at or near the distal end of the central wire; and
   a microcatheter at least partially containing the engaging element during introduction into the body lumen,
   wherein the engaging element, when expanded upon unsheathing from the microcatheter, is configured to inhibit re-sheathing of the engaging element in the microcatheter upon application of at least one of a proximal force to the engaging element or a distal force to the microcatheter at least while a proximal end of the engaging element abuts a distal tip of the microcatheter.

* * * * *

UNITED STATES PATENT AND TRADEMARK OFFICE
CERTIFICATE OF CORRECTION

PATENT NO. : 11,504,150 B2
APPLICATION NO. : 16/810518
DATED : November 22, 2022
INVENTOR(S) : Marks et al.

Page 1 of 1

It is certified that error appears in the above-identified patent and that said Letters Patent is hereby corrected as shown below:

In the Specification

On Column 23, Line 51: Delete ""*"" and insert -- "**" --.

On Column 24, Lines 5-21: Below "wire." delete "FIG. 12 illustrates still another embodiment of a device where the device may comprise a plurality of engaging elements. In some embodiments, the device may comprise a central wire (10), a control wire (100), and a plurality of operation unit/pair, e.g. each unit/pair comprising two, or more pairs of clot engagement elements. In each of the engagement operation unit/pair, at least one receiving element and one capturing element may be present, and generally the receiving element may be located proximal to the capturing elements. In some embodiments, some or all of the (proximal and intermediate) receiving elements (68) may be fixed to the control wire (100). In some other embodiments, the (distal and middle) capturing elements (69), can be fixed to the central wire (10) via connector (47, 80). In certain embodiments, the proximal and middle receiving element (68) can be associated with (or connected to) the central wire (10) but freely slide on the central wire.".

Signed and Sealed this
Fourth Day of April, 2023

Katherine Kelly Vidal
*Director of the United States Patent and Trademark Office*